(12) United States Patent
Flygare et al.

(10) Patent No.: US 8,907,092 B2
(45) Date of Patent: Dec. 9, 2014

(54) INHIBITORS OF IAP

(75) Inventors: John A. Flygare, Burlingame, CA (US); Frederick Cohen, San Francisco, CA (US); Kurt Deshayes, San Francisco, CA (US); Michael F. T. Koehler, Palo Alto, CA (US); Lewis J. Gazzard, Belmont, CA (US); Lan Wang, Foster City, CA (US); Chudi Ndubaku, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1299 days.

(21) Appl. No.: 12/598,027

(22) PCT Filed: Apr. 29, 2008

(86) PCT No.: PCT/US2008/061891
§ 371 (c)(1),
(2), (4) Date: Nov. 22, 2010

(87) PCT Pub. No.: WO2008/134679
PCT Pub. Date: Nov. 6, 2008

(65) Prior Publication Data
US 2011/0077265 A1    Mar. 31, 2011

Related U.S. Application Data

(60) Provisional application No. 60/915,010, filed on Apr. 30, 2007.

(51) Int. Cl.
| | | |
|---|---|---|
| C07D 277/46 | (2006.01) | |
| C07D 513/04 | (2006.01) | |
| C07D 417/14 | (2006.01) | |
| A61K 31/4365 | (2006.01) | |
| A61K 31/4436 | (2006.01) | |
| A61K 31/427 | (2006.01) | |
| C07D 207/16 | (2006.01) | |
| C07D 519/00 | (2006.01) | |

(52) U.S. Cl.
CPC ............ C07D 417/14 (2013.01); C07D 207/16 (2013.01); C07D 519/00 (2013.01)
USPC ........... 546/114; 549/209; 548/192; 514/301; 514/326; 514/371

(58) Field of Classification Search
USPC .................. 546/114, 209; 514/301, 326, 371; 548/192
See application file for complete search history.

(56) References Cited

U.S. PATENT DOCUMENTS

| | | |
|---|---|---|
| 4,149,003 A | 4/1979 | Carlsson et al. |
| 4,278,793 A | 7/1981 | Dürckheimer et al. |
| 4,720,484 A | 1/1988 | Vincent et al. |
| 4,837,165 A | 6/1989 | Hawke |
| 4,935,494 A | 6/1990 | Miller |
| 5,278,148 A | 1/1994 | Branca et al. |
| 5,411,942 A | 5/1995 | Widmer et al. |
| 5,559,209 A | 9/1996 | Nishimoto |
| 5,998,470 A | 12/1999 | Halbert et al. |
| 6,472,172 B1 | 10/2002 | Deng et al. |
| 6,608,026 B1 | 8/2003 | Wang et al. |
| 6,992,063 B2 | 1/2006 | Shi |
| 7,041,784 B2 | 5/2006 | Wang et al. |
| 7,067,274 B2 | 6/2006 | Fairbrother et al. |
| 7,244,851 B2 | 7/2007 | Cohen et al. |
| 8,110,568 B2 | 2/2012 | Cohen et al. |
| 8,247,557 B2 | 8/2012 | Koehler et al. |
| 2002/0177557 A1 | 11/2002 | Shi |
| 2003/0157522 A1 | 8/2003 | Boudreault et al. |
| 2004/0171554 A1 | 9/2004 | Deshayes et al. |
| 2005/0197403 A1 | 9/2005 | Harran et al. |
| 2005/0214802 A1 | 9/2005 | Fairbrother et al. |
| 2005/0234042 A1 | 10/2005 | Palermo et al. |
| 2006/0014700 A1 | 1/2006 | Cohen et al. |
| 2006/0052311 A1 | 3/2006 | Sharma et al. |
| 2006/0194741 A1 | 8/2006 | Condon et al. |

(Continued)

FOREIGN PATENT DOCUMENTS

| | | |
|---|---|---|
| EP | 1 836201 B1 | 9/2007 |
| JP | 2006-501181 A | 1/2006 |

(Continued)

OTHER PUBLICATIONS

Extended European Search Report dated Dec. 20, 2010, received in corresponding EP Application No. 08747109.0. Anonymous. (Oct. 11, 2011). Compendium of Chemical Terminology Gold Book, Version 2.3, International Union of Pure and Applied Chemistry, four pages, pp. 57, 212, and 1052.
Arnt, C.R. et al. (Nov. 15, 2002). "Synthetic Smac/DIABLO Peptides Enhance the Effects of Chemotherapeutic Agents by Binding XIAP and cIAP1 in Situ," *Journal of Biological Chemistry* 277(46):44236-44243.

(Continued)

*Primary Examiner* — David K O Dell
(74) *Attorney, Agent, or Firm* — Morrison & Foerster LLP

(57) ABSTRACT

The invention provides novel inhibitors of IAP that are useful as therapeutic agents for treating malignancies where the compounds having the general formula U1-M-U2 wherein M is a linking group covalently joining R2, R3, R4 or R5 of U1 to an R2, R3, R4 or R5 group of U2; U1 and U2 have the general formula (I) and G, X1, X2, R2, R3, R3', R4, R4' and R5, are as described herein.

(I)

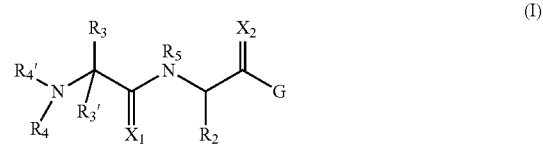

12 Claims, No Drawings

(56) References Cited

U.S. PATENT DOCUMENTS

| | | |
|---|---|---|
| 2007/0093428 A1 | 4/2007 | Laurent |
| 2007/0299052 A1 | 12/2007 | Cohen et al. |
| 2008/0050336 A1* | 2/2008 | Bachand et al. ............ 424/85.2 |
| 2009/0318409 A1 | 12/2009 | Cohen et al. |
| 2011/0046066 A1 | 2/2011 | Ndubaku et al. |
| 2011/0218211 A1 | 9/2011 | Bergeron et al. |
| 2011/0269696 A1 | 11/2011 | Dudley et al. |
| 2012/0015974 A1 | 1/2012 | Koehler |
| 2012/0202750 A1 | 8/2012 | Cohen et al. |
| 2012/0270886 A1 | 10/2012 | Koehler et al. |

FOREIGN PATENT DOCUMENTS

| | | |
|---|---|---|
| JP | 2009-545613 A | 12/2009 |
| JP | 2010-506847 A | 3/2010 |
| RU | 2291154 C2 | 1/2007 |
| WO | WO-92/01938 A1 | 2/1992 |
| WO | WO-94/11026 A2 | 5/1994 |
| WO | WO-94/11026 A3 | 5/1994 |
| WO | WO-94/11026 C1 | 5/1994 |
| WO | WO-98/46597 A1 | 10/1998 |
| WO | WO-00/00823 A1 | 1/2000 |
| WO | WO-00/39585 A1 | 7/2000 |
| WO | WO-02/16402 A2 | 2/2002 |
| WO | WO-02/16402 A3 | 2/2002 |
| WO | WO-02/16418 A2 | 2/2002 |
| WO | WO-02/16418 A3 | 2/2002 |
| WO | WO-02/26775 A2 | 4/2002 |
| WO | WO-02/26775 A3 | 4/2002 |
| WO | WO-02/30959 A2 | 4/2002 |
| WO | WO-02/30959 A3 | 4/2002 |
| WO | WO-02/085897 A1 | 10/2002 |
| WO | WO-02/096930 A2 | 12/2002 |
| WO | WO-02/096930 A3 | 12/2002 |
| WO | WO-03/010184 A2 | 2/2003 |
| WO | WO-03/010184 A3 | 2/2003 |
| WO | WO-03/086470 A2 | 10/2003 |
| WO | WO-03/086470 A3 | 10/2003 |
| WO | WO-2004/005248 A1 | 1/2004 |
| WO | WO-2004/007529 A2 | 1/2004 |
| WO | WO-2004/007529 A3 | 1/2004 |
| WO | WO-2004/017991 A1 | 3/2004 |
| WO | WO-2004/072641 A1 | 8/2004 |
| WO | WO-2005/069888 A3 | 8/2004 |
| WO | WO-2004/106371 A1 | 12/2004 |
| WO | WO-2005/049853 A2 | 6/2005 |
| WO | WO-2005/049853 A3 | 6/2005 |
| WO | WO-2005/069888 A2 | 8/2005 |
| WO | WO-2005/069894 A2 | 8/2005 |
| WO | WO-2005/069894 A3 | 8/2005 |
| WO | WO-2005/069894 C1 | 8/2005 |
| WO | WO-2005/094818 A1 | 10/2005 |
| WO | WO-2005/097791 A1 | 10/2005 |
| WO | WO-2006/014361 A1 | 2/2006 |
| WO | WO-2006/017295 A2 | 2/2006 |
| WO | WO-2006/017295 A3 | 2/2006 |
| WO | WO-2006/020060 A2 | 2/2006 |
| WO | WO-2006/020060 A3 | 2/2006 |
| WO | WO-2006/069063 A1 | 6/2006 |
| WO | 2006/091972 A2 | 8/2006 |
| WO | 2006/122408 | 11/2006 |
| WO | WO-2007/048224 A1 | 5/2007 |
| WO | 2007/104162 | 9/2007 |
| WO | WO-2007/106192 A2 | 9/2007 |
| WO | WO-2007/106192 A3 | 9/2007 |
| WO | WO-2007/136921 A2 | 11/2007 |
| WO | WO-2007/136921 A3 | 11/2007 |
| WO | WO-2007/136921 C1 | 11/2007 |
| WO | 2008/014238 | 1/2008 |
| WO | WO-2008/016893 A1 | 2/2008 |
| WO | WO-2008/045905 A1 | 4/2008 |

OTHER PUBLICATIONS

Bajaj, K. et al. (Dec. 2007). "Stereochemical Criteria for Prediction of the Effects of Proline Mutations on Protein Stability," *PLOS Computational Biology* 3(12)(e241):2465-2475.

Baktiar, C. et al. (Jan. 1994). "Transfer of Alkoxycarbonyl From Alkyl imidazolium-2-Carboxylates to Benzyl Alcohol, a Cyclohexanone Enamine and Diethylamine," *J. Chem. Soc. Perkin. Trans.* 1 3:329-243.

Blass, B.E. et al. (2000). "Parallel Synthesis and Evaluation of N-(1-Phenylethyl)-5-phenyl-imidazole-2-amines as Na+/K+ ATPase inhibitors" *Bioorganic & Medicinal Chemistry Letters* 10:1543-1545.

Boatright, K.M. et al. (Feb. 2003). "A Unified Model for Apical Caspase Activation," *Molecular Cell* 11:529-541.

Boden, C.D.J. et al. (Dec. 9, 1996). "Total Synthesis of the Thiazoline-Based Cyclopeptide Cyclodidemnamide," *Tetrahedron Letters* 37(50):9111-9114.

Chai, J. et al. (Aug. 24, 2000). "Structural and Biochemical Basis of Apoptotic Activation by SMAC/DIABLO;" *Nature* 406(6798):855-862.

Chari, R.V.J. et al. (Jan. 1, 1992). "Immunoconjugates Containing Novel Maytansinoids: Promising Anticancer Drugs," *Cancer Research* 52:127-131.

Chen, P. et al. (1996). "*grim*, a novel cell death gene in *Drosophila*," *Genes & Development* 10:1773-1782.

Christich, A. et al. (Jan. 22, 2002). "The Damage-Responsive *Drosophila* Gene *sickle* Encodes a Novel IAP Binding Protein Similar to but Distinct from *reaper, grim*, and *hid*," *Current Biology* 12:137-140.

Ciufolini, M.A. et al. (1997). "Studies Toward Thiostrepton Antibiotics: Assembly of the Central Pyridine-Thiazole Cluster of Micrococcins," *J. Org. Chem.* 62:3804-3805.

Eurasian Patent Office Search Report for Eurasian Patent Application No. 201170344, filed on Aug. 14, 2009, one page. (Russian Only.).

Corey, E.J. et al. (1989). "(+)-1(S), 5(R), 8(S)-8-Phenyl-2-Azabicyclo[3.3.0]Octan-8-ol N,O-Methylboronate (2) and Its Enantiomer, Chiral Chemzymes Which Serve As Catalysts for Their Own Enantioselective Synthesis," *Tetrahedron Letters* 30(41):5547-5550.

Crook, N.E. et al. (Apr. 1993). "An Apoptosis-Inhibiting Baculovirus Gene with a Zinc Finger-Like Motif," *Journal of Virology* 67(4):2168-2174.

Derossi, D. et al. (Feb. 1998). "Trojan Peptides: The Penetratin System for Intracellular Delivery," *Trends in Cell Biology* 8:84-87.

Deveraux, Q.L. et al. (1999). "Endogenous Inhibitors of Caspases," *Journal of Clinical Immunology* 19(6):388-398.

Deveraux, Q.L. et al. (1998). "IAPs Block Apoptotic Events Induced by Caspase-8 and Cytochrome *c* by Direct Inhibition of Distinct Caspases," *The EMBO Journal* 17(8):2215-2223.

Deveraux, Q.L. et al. (1999). "IAP Family Proteins-Suppressors of Apoptosis," *Genes & Development* 13:239-252.

Duckett, C.S. et al. (1996). "A Conserved Family of Cellular Genes Related to the Baculovirus IAP Gene and Encoding Apoptosis Inhibitors," *The EMBO Journal* 15(11):2685-2694.

Extended European Search Report mailed Dec. 28, 2010, for EP Application No. 08747109.0, filed on Apr. 29, 2008, nine pages.

Fojo, T. et al. (2003). "Strategies for Reversing Drug Resistance," *Oncogene* 22:7512-7523.

Fong, W.G. et al. (2000). "Expression and Genetic Analysis of XIAP-Associated Factor 1 (XAF1) in Cancer Cell Lines," *Genomics* 70:113-122.

Franklin, M.C. et al. (2003). "Structure and Function Analysis of Peptide Antagonists of Melanoma Inhibitor of Apoptosis (ML-IAP)," *Biochemistry* 42:8223-8231.

Freshney, R.I. (1983). *Culture of Animal Cells, A Manual of Basic Technique*, Alan R. Liss, Inc., New York, New York, p. 4.

Fulda, S. et al. (Aug. 2002). "Smac Agonists Sensitize for Apo2L/TRAIL—or Anticancer Drug-Induced Apoptosis and Induce Regression of Malignant Glioma in vivo," *Nature Medicine* 8(8):808-815.

Giménez-Bonafé, P. et al. (2009). "Overcoming Drug Resistance by Enhancing Apoptosis of Tumor Cells," *Current Cancer Drug Targets* 9:320-340.

(56) References Cited

OTHER PUBLICATIONS

Gordon, T. et al. (1993). "Peptide Azoles: A New Class of Biologically-Active Dipeptide Mimetics," *Bioorganic & Medicinal Chemistry Letters* 3(5):915-920.

Goyal, L. et al. (2000). "Induction of Apoptosis by *Drosophila reaper, hid* and *grim* through Inhibition of IAP Function," *The EMBO Journal* 19(4):589-597.

Grether, M.E. et al. (1995). "The Head Involution Defective Gene of *Drosophila melanogaster* Functions in Programmed Cell Death," *Genes & Developmment* 9:1694-1708.

Guo, F. et al. (2002). "Ectopic Overexpression of Second Mitochondria-Derived Activator of Caspases (Smac/DIABLO) or Cotreatment with N-Terminus of Smac/DIABLO Peptide Potentiates Epothilone B Derivative-(BMS 247550) and Apo-2L/TRAIL-Induced Apoptosis" *Blood* 99:3419-3426.

Hamada, Y. et al. (1985). "New Methods and Reagents in Organic Synthesis. 58. A Synthesis of Patellamide A, a Cytotoxic Cyclic Peptide from a Tunicate. Revision of its Proposed Structure," *Tetrahedron Letters* 26(52):6501-6504.

Hamada, Y. et al. (1985). "New Methods and Reagents in Organic Synthesis. 56. Total Syntheses of Patellamides B and C, Cytotoxic Cyclic Peptides From a Tunicate 2. Their Real Structures Have Been Determined by Their Syntheses," *Tetrahedron Letters* 26(42):5159-5162.

Hinds, M.G. et al. (Jul. 1999). "Solution Structure of a Baculoviral Inhibitor of Apoptosis (IAP) Repeat," *Nature Structural Biology* 6(7):648-651.

Holder, J.R. et al. (Dec. 19, 2002, e-pub. Nov. 23, 2002). "Structure-Activity Relationships of the Melanocortin Tetrapeptide Ac-His-D-Phe-Arg-Trp-NH$_2$ at the Mouse Melanocortin Receptors. 4. Modifications at the Trp Position," *Journal of Medicinal Chemistry* 45(26):5736-5744.

Hu, Y. et al. (Jul. 2003). "Antisense Oligonucleotides Targeting XIAP Induce Apoptosis and Enhance Chemotherapeutic Activity Against Human Lung Cancer Cells in Vitro and in Vivo," *Clinical Cancer Research* 9(7):2826-2836.

International Preliminary Report on Patentability mailed on Feb. 8, 2011, for PCT Patent Application No. PCT/US2009/051522, filed on Jul. 23, 2009, six pages.

International Search Report and Written Opinion mailed on Apr. 5, 2010, for PCT Patent Application No. PCT/US2009/053889, filed on Aug. 14, 2009, nine pages.

International Search Report and Written Opinion mailed on May 7, 2009, for PCT Patent Application No. PCT/US2009/030674, filed on Jan. 9, 2009, twenty-one pages.

Ireland, C.M. et al. (1982). "Antineoplastic Cyclic Peptides From the Marine Tunicate *Lissoclinum patella*," *J. Org. Chem.* 47(10):1807-1811.

Jones, T.A. et al. (1991). "Improved Methods for Building Protein Models in Electron Density Maps and the Location of Errors in These Models," *Acta Cryst.* A47:110-119.

Joyeau, R. et al. (2000). "Synthesis and Activity of Pyrrolidinyl- and Thiazolidinyl-Dipeptide Derivatives as Inhibitors of the Tc80 Prolyl Oligopeptidase from *Trypanosoma cruzi*," *Eur. J. Med. Chem.* 35(2):257-266.

Keating, S. et al. (2000). "Putting the Pieces Together: Contribution of Fluorescence Polarization Assays to Small Molecule Lead Optimization," *Proceedings of SPIE: In-Vitro Diagnostic Instrumentation*, Cohn, G.E. ed. 3913:128-137.

Kipp, R.A. et al. (2002). "Molecular Targeting of Inhibitor of Apoptosis Proteins Based on Small Molecule Mimics of Natural Binding Partners," *Biochemistry* 41(23):7344-7349.

Kolb, J.M. et al. (1996). "Use of a Novel Homogeneous Fluorescent Technology in High Throughput Screening," *Journal of Biomolecular Screening* 1(4):203-210.

Lacasse, E.C. et al. (1998). "The Inhibitors of Apoptosis (IAPs) and Their Emerging Role in Cancer," *Oncogene* 17(25):3247-3259.

Lawton, L.A. et al. (1999, e-pub. Jun. 24, 1999). "A Bioactive Modified Peptide, Aeruginosamide, Isolated from the Cyanobacterium *Microcystis aeruginosa*," *J. Org. Chem.* 64(14):5329-5332.

Li, L. et al. (Sep. 3, 2004). "A Small Molecule Smac Mimic Potentiates TRAIL- and TNF⊕-Mediated Cell Death," *Science* 305:1471-1474.

Lin, H. et al. (2001). "Resistance of Bone Marrow-Derived Macrophages to Apoptosis is Associated With the Expression of X-Linked Inhibitor of Apoptosis Protein in Primary Cultures of Bone Marrow Cells," *Biochemical Journal* 353:299-306.

Liston, P. et al. (Jan. 25, 1996). "Suppression of Apoptosis in Mammalian Cells by NAIP and a Related Family of IAP Genes," *Nature* 379:349-353.

Liu, C. et al. (Aug. 1996). "Eradication of Large Colon Tumor Xenografts by Targeted Delivery of Maytansinoids," *Proc. Natl. Acad. Sci. USA* 93:8618-8623.

Liu, Z. et al. (Dec. 2000). "Structural Basis for Binding of Smac/DIABLO to the XIAP BIR3 Domain," *Nature* 408:1004-1008.

MacArthur, M.W. et al. (Mar. 20, 1991). "Influence of Proline Residues on Protein Conformation," *J. Mol. Biol.* 218(2):397-412.

Masuda, K. et al. (1981). "Studies on Mesoionic Compounds. Part 11. Alkylation of 5-Acylamino-1,2,3-Thiadiazoles," *J. Chem. Soc. Perkin Trans. I* 5:1591-1595.

Maybridge Medchem. (Oct. 24, 2005). "Maybridge Medchem, Bioisosteres in Medicinal Chemistry and references cited therein," twenty-two pages.

Moody, C.J. et al. (1999, e-pub. Oct. 23, 1999). "Synthesis of Virenamide B, a Cytotoxic Thiazole-Containing Peptide," *J. Org. Chem.* 64:8715-8717.

Murray, E.D. et al. (Sep. 10, 1984). "Synthetic Peptide Substrates for the Erythrocyte Protein Carboxyl Methyltransferase," *The Journal of Biological Chemistry* 259(17):10722-10732.

Murshudov, G.N. et al. (1997). "Refinement of Macromolecular Structures by the Maximum-Likelihood Method," *Acta Cryst.* D53:240-255.

Nakamura et al. (Jul. 10, 1995). "Stereochemistry and Total Synthesis of Dolastatin E," *Tetrahedron Letters* 36(28):5059-5062.

Ndubaku, C. et al. (2009, e-pub. Jun. 3, 2009). "Antagonism of c-IAP and XIAP Proteins Is Required for Efficient Induction of Cell Death by Small-Molecule IAP Antagonists," *ACS Chemical Biology* 4(7):557-566.

Ng, C-P. et al. (Oct. 2002). "X-Linked Inhibition of Apoptosis (XIAP) Blocks Apo2 Ligand/Tumor Necrosis Factor-Related Apoptosis-Inducing Ligand-Mediated Apoptosis of Prostate Cancer Cells in the Presence of Mitochondrial Activation: Sensitization by Overexpression of Second Mitochondria-Derived Activator of Caspase/Direct IAP-Binding Protein With Low pI (Smac/DIABLO)," *Molecular Cancer Therapeutics* 1:1051-1058.

Norley, M.C. et al. (1998). "Total Synthesis and Revision of Stereochemistry of Cyclodidemnamide, a Novel Cyclopeptide from the Marine Ascidian *Didemnum molle*," *Tetrahedron Letters* 39:3087-3090.

Ösz, K. et al. (2003, e-pub. Apr. 23, 2003). "Transition Metal Complexes of Bis(imidazol-2-yl) Derivatives of Dipeptides," *Dalton Transactions* pp. 2009-2016.

Pan, G. et al. (Aug. 8, 1997). "An Antagonist Decoy Receptor and a Death-Domain Containing Receptor for TRAIL," *Science* 277:815-818.

Perrakis, A. et al. (2001). "*ARP/wARP* and Molecular Replacement," *Acta Crystallographica* D57:1445-1450.

Pichon-Pesme, V. et al. (1995). "On Building a Data Bank of Transferable Experimental Electron: Density Parameters: Application to Polypeptides," *J. Phys. Chem.* 99(16):6242-6250.

Prochiantz, A. (1996). "Getting Hydrophilic Compounds into Cells: Lessons from Homeopeptides," *Current Opinion in Neurobiology* 6(5):629-634.

Riedl, S.J. et al. (Mar. 9, 2001). "Structural Basis for the Inhibition of Caspase-3 by XIAP," *Cell* 104:791-800.

Salvesen et al. (1989). "Determination of Protease Mechanism," in *Proteolytic Enzymes: A Practical Approach*, R.J. Beynon and J.S. Bond, Oxford, IRL Press, pp. 83-104.

Sanna, M.G. et al. (Mar. 2002). "IAP Suppression of Apoptosis Involves Distinct Mechanisms: the TAK1/JNK1 Signaling Cascade and Caspase Inhibition," *Molecular and Cell Biology* 22(6):1754-1766.

(56) References Cited

OTHER PUBLICATIONS

Sasaki, H. et al. (Oct. 15, 2000). "Down-Regulation of X-Linked Inhibitor of Apoptosis Protein Induces Apoptosis in Chemoresistant Human Ovarian Cancer Cells," *Cancer Research* 60(20):5659-5666.
Schimmer, A.D. et al. (2005). "Targeting the IAP Family of Caspase Inhibitors as an Emerging Therapeutic Strategy," *Hematology* pp. 215-219.
Shiozaki, E.N. et al. (Feb. 2003). "Mechanism of XIAP-Mediated Inhibition of Caspase-9," *Molecular Cell* 11:519-527.
Shuker, S.B. et al. (Nov. 29, 1996). "Discovering High-Affinity Ligands for Proteins: SAR by NMR," *Science* 274:1531-1534.
Sidhu, S.S. et al (2000). "Phage Display for Selection of Novel Binding Peptides," *Methods in Enzymology* 328:333-363.
Srinivasula, S.M. et al. (Mar. 1, 2001). "A Conserved XIAP-Interaction Motif in Caspase-9 and Smac/DIABLO Regulates Caspase Activity and Apoptosis," *Nature* 410:112-116.
Srinivasula, S.M. et al. (Jan. 22, 2002). "Sickle, A Novel *Drosophila* Death Gene in the *Reaper/Hid/Grim* Region, Encodes an IAP-Inhibitory Protein," *Current Biology* 12:125-130.
STN International. (Apr. 15, 2009). "STN-11739030A," last visited on Sep. 15, 2009, thirty-seven pages.
Stark, G.R. (May 1968). "Sequential Degradation of Peptides From Their Carboxyl Termini With Ammonium Thiocyanate and Acetic Anhydride," *Biochemistry* 7(5):1796-1807.
Sun, C. et al. (Oct. 21, 1999). "NMR Structure and Mutagenesis of the Inhibitor-of-Apoptosis Protein XIAP," *Nature* 401:818-822.
Sun, C. et al. (Oct. 27, 2000). "NMR Structure and Mutagenesis of the Third Bir Domain of the Inhibitor of Apoptosis Protein XIAP," *The Journal of Biological Chemistry* 275(43):33777-33781.
Supplementary European Search Report mailed Sep. 23, 2011, for EP Application No. 09805348.1, filed on Jul. 23, 2009, eight pages.
Supplementary European Search Report mailed Sep. 20, 2010, for EP Application No. 06850324.2, six pages.
Takahashi, R. et al. (Apr. 3, 1998). "A Single BIR Domain of XIAP Sufficient for Inhibiting Caspases," *The Journal of Biological Chemistry* 273(14):7787-7790.
Tamm, I. et al. (May 2000). "Expression and Prognostic Significance of IAP-Family Genes in Human Cancers and Myeloid Leukemias," *Clinical Cancer Research* 6(5):1796-1803.
Tenev, T. et al. (2002). "Jafrac2 is an IAP Antagonist that Promotes Cell Death by Liberating Dronc From DIAP1," *The EMBO Journal* 21(19):5118-5129.
Thompson, C.B. (Mar. 10, 1995). "Apoptosis in the Pathogenesis and Treatment of Disease," *Science* 267:1456-1462.
Thompson, S.K. et al. (Dec. 1997). "Design of Potent and Selective Human Cathepsin K Inhibitors that Span the Active Site," *Proc. Natl. Acad. Sci. USA* 94:14249-14254.
Thompson, S.K. et al. (1994, e-pub. Aug. 1, 1994). "Rational Design, Synthesis, and Crystallographic Analysis of a Hydroxyethylene-Based HIV-1 Protease Inhibitor Containing a Heterocyclic $P_1$-$P_2$ Amide Bond Isostere," *J. Med. Chem.* 37(19):3100-3107.
Thompson, S.K. et al. (1994). "Synthesis and Antiviral Activity of a Novel Class of HIV-1 Protease Inhibitors Containing a Heterocyclic P1-P2 Amide Bond Isostere," *Bioorganic and Medicinal Chemistry Letters* 4(20):2441-2446.
U.S. Appl. No. 60/560,186, filed Apr. 7, 2004, by Palermo et al. seventy-four pages.
Vippagunta, S.R. et al. (2001). "Crystalline Solids," *Advanced Drug Delivery Reviews* 48:3-26.
Vucic, D. et al. (Oct. 17, 2000). "ML-IAP, A Novel Inhibitor of Apoptosis that is Preferentially Expressed in Human Melanomas," *Current Biology* 10:1359-1366.
Vucic, D. et al. (Apr. 5, 2002). "SMAC Negatively Regulates the Anti-Apoptotic Activity of Melanoma Inhibitor of Apoptosis (ML-IAP)," *The Journal of Biological Chemistry* 277(14):12275-12279.
Vucic, D. et al. (Jan. 2005). "Engineering ML-IAP to Produce an Extraordinarily Potent Caspase 9 Inhibitor: Implications for Smac-Dependent Anti-Apoptotic Activity of ML-IAP," *Biochemical Journal* 385(Part 1):11-20.
West, A.R. (1984). "Solid Solutions," Chapter 10 in *Solid State Chemistry and Its Applications*, John Wiley and Sons, New York, pp. 358 and 365.
White, K. et al. (Apr. 29, 1994). "Genetic Control of Programmed Cell Death in *Drosophila*," *Science* 264:677-683.
Wing, J.P. et al. (Jan. 22, 2002). "*Drosophila sickle* is a Novel *grim-reaper* Cell Death Activator," *Current Biology* 12:131-135.
Wu, G. et al. (Dec. 2000). "Structural Basis of IAP Recognition by Smac/DIABLO," *Nature* 408:1008-1012.
Wu, J-W. et al (Jul. 2001). "Structural Analysis of a Functional DIAP1 Fragment Bound to Grim and Hid Peptides," *Molecular Cell* 8:95-104.
Yang, L. et al. (Feb. 15, 2003). "Predominant Suppression of Apoptosome by Inhibitor of Apoptosis Protein in Non-Small Cell Lung Cancer H460 Cells: Therapeutic Effect of a Novel Polyarginine-Conjugated Smac Peptide," *Cancer Research* 63(4):831-837.
Yokokawa, F. et al. (2001). "Total Synthesis of *cis,cis*-Ceratospongamide, a Bioactive Thiazole-Containing Cyclic Peptide from Marine Origin," *Synlett* SI:986-988.
Yokokawa, F. et al. (2002). "Total Synthesis and Conformational Studies of Ceratospongamide, a Bioactive Cyclic Heptapeptide From Marine Origin," *Tetrahedron* 58:8127-8143.

\* cited by examiner

SEQUENCE LISTING

<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

Met Gly Ser Ser His His His His His His Ser Ser Gly Leu Val
 1               5                  10                  15

Pro Arg Gly Ser His Met Leu Glu Thr Glu Glu Glu Glu Glu
                20                  25                  30

Gly Ala Gly Ala Thr Leu Ser Arg Gly Pro Ala Phe Pro Gly Met
                35                  40                  45

Gly Ser Glu Glu Leu Arg Leu Ala Ser Phe Tyr Asp Trp Pro Leu
                50                  55                  60

Thr Ala Glu Val Pro Pro Glu Leu Leu Ala Ala Ala Gly Phe Phe
                65                  70                  75

His Thr Gly His Gln Asp Lys Val Arg Cys Phe Phe Cys Tyr Gly
                80                  85                  90

```
Gly Leu Gln Ser Trp Lys Arg Gly Asp Asp Pro Trp Thr Glu His
                95                  100                 105

Ala Lys Trp Phe Pro Gly Cys Gln Phe Leu Leu Arg Ser Lys Gly
                110                 115                 120

Gln Glu Tyr Ile Asn Asn Ile His Leu Thr His Ser Leu
                125                 130
```

INHIBITORS OF IAP

RELATED APPLICATION

This application claims priority to and the benefit of U.S. Provisional Patent Application No. 60/915,010, filed Apr. 30, 2007, which is incorporated by reference in its entirety herein.

FIELD OF THE INVENTION

The present invention relates to organic compounds useful for therapy and/or prophylaxis in a mammal, and in particular to inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563): 349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406: 855-862, Liu et al., (2000) Nature 408:1004-1008, Wu et al., (2000) Nature 408 1008-1012).

SUMMARY OF THE INVENTION

In one aspect of the present invention there is provided novel inhibitors of IAP proteins having the general formula (I)

$$U_1\text{-}M\text{-}U_2$$

wherein $U_1$ and $U_2$ have the general formula (I)

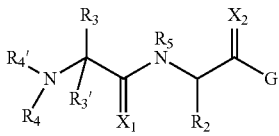

wherein $X_1$ and $X_2$ are each independently O or S;

$R_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, alkoxy, alkylthio, sulfonyl, amino and nitro;

$R_3$ is H or alkyl optionally substituted with halogen or hydroxyl; or $R_3$ and $R_4$ together form a 3-6 heterocycle;

$R_3'$ is H, or $R_3$ and $R_3'$ together form a 3-6 carbocycle;

$R_4$ and $R_4'$ are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or $R_4$ and $R_4'$ together form a heterocycle;

$R_5$ is H or alkyl;

G is selected from the group consisting of IVa to IVe

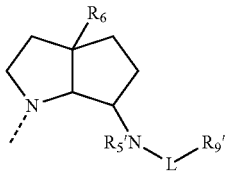

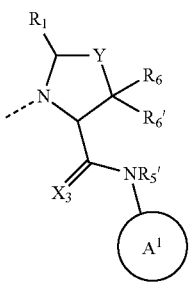

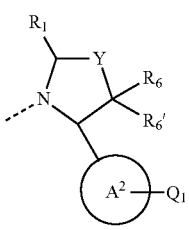

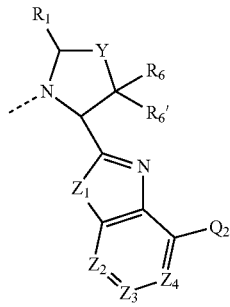

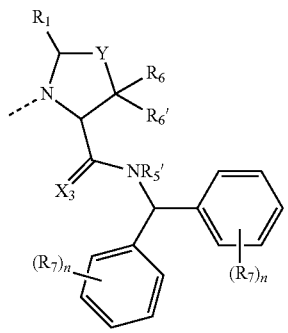

wherein $R_1$ is H, OH or alkyl; or $R_1$ and $R_2$ together form a 5-8 member heterocycle;

$R_5'$ is H or alkyl;

$R_6$, and $R_6'$ are each independently H, alkyl, aryl or aralkyl;

$R_7$ is in each occurrence is independently H, cyano, hydroxyl, mercapto, halogen, nitro, carboxyl, amidino, guanidino, alkyl, a carbocycle, a heterocycle or —U—V; wherein U is —O—, —S—, —S(O)—, S(O)$_2$, —N($R_8$)—, —C(O)—, —C(O)—N$R_8$—, —N$R_8$—C(O)—, —SO$_2$—N$R_8$—, —N$R_8$—SO$_2$—, —N$R_8$—C(O)—N$R_8$—, —N$R_8$—C(NH)—N$R_8$—, —N$R_8$—C(NH)—, —C(O)—O— or —O—C(O)— and V is alkyl, a carbocycle or a heterocycle; and wherein one or more CH$_2$ or CH groups of an alkyl is optionally replaced with —O—, —S—, —S(O)—, S(O)$_2$, —N($R_8$)—, —C(O)—, —C(O)—N$R_8$—, —N$R_8$—C(O)—, —SO$_2$—N$R_8$—, —N$R_8$—SO$_2$—, —N$R_8$—C(O)—N$R_8$—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle;

$R_9'$ is $Q_1$ or $Q_2$;

$A^1$ is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle;

$A^2$ is a 5-member aromatic heterocycle incorporating 1 to 4 heteroatoms N, O or S and is optionally substituted with one or more $R_7$ and $R_8$ groups;

L is a bond, —C($X_3$)—, —C($X_3$)$NR_{12}$ or —C($X_3$)O— wherein $X_3$ is O or S and $R_{12}$ is H or $R_1$;

$Q_1$ and $Q_2$ are independently H, alkyl, a carbocycle, a heterocycle; wherein one or more $CH_2$ or CH groups of an alkyl is optionally replaced with —O—, —S—, —S(O)—, S(O)$_2$, —N($R_8$)—, —C(O)—, —C(O)—$NR_8$—, —$NR_8$—C(O)—, —SO$_2$—$NR_8$—, —$NR_8$—SO$_2$—, —$NR_8$—C(O)—$NR_8$—, —$NR_8$—C(NH)—$NR_8$—, —$NR_8$—C(NH)—, —C(O)—O— or —O—C(O)—; and wherein any of the foregoing alkyl, carbocycle and heterocycle is optionally substituted with one or more hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle.

$X_3$ is O or S;

Y is a bond, (CR$_7$R$_7$)$_{n'}$, O or S; wherein n' is 1 or 2 and $R_7$ is H, halogen, alkyl, aryl, aralkyl, amino, arylamino, alkylamino, aralkylamino, alkoxy, aryloxy or aralkyloxy;

$Z_1$ is $NR_8$, O, S, SO or $SO_2$;

$Z_2$, $Z_3$ and $Z_4$ are independently $CQ_2$ or N; and

M is a linking group covalently joining $U_1$ and $U_2$; and n in each occurrence is independently 0 to 4.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion may be a saturated hydrocarbon chain, however also includes unsaturated hydrocarbon carbon chains such as "alkenylamino" and "alkynylamino. Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one, for example two, three or four substituents which may be the same or different. Examples of substituents are, unless otherwise defined, halogen, amino, hydroxyl, protected hydroxyl, mercapto, carboxy, alkoxy, nitro, cyano, amidino, guanidino, urea, sulfonyl, sulfinyl, aminosulfonyl, alkylsulfonylamino, arylsulfonylamino, aminocarbonyl, acylamino, alkoxy, acyl, acyloxy, a carbocycle, a heterocycle. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Substituted alkyls include substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" means the group —C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular amidine is the group —NH—C(NH)—$NH_2$.

"Amino" means primary (i.e. —$NH_2$), secondary (i.e. —NRH) and tertiary (i.e. —NRR) amines in which R is H, alkyl, a carbocycle, a heterocycle, carbocycle-substituted alkyl or heterocycle-substituted alkyl wherein the alkyl, alkoxy, carbocycle and heterocycle are as defined herein. Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", $2^{nd}$ ed., a John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene dioxybenzyl, benzhydryl, 4,4'-dimethoxybenzhydrol, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Particular carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

"Compounds" include salts and solvates (e.g. hydrates) thereof.

"Guanidine" means the group —NH—C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2$^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-astriazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5, 6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the binding of IAP proteins to caspase proteins or which reduces or prevents the inhibition of apoptosis by an IAP protein. Alternatively, "inhibitor" means a compound which prevents the binding interaction of X-IAP with caspases or the binding interaction of ML-IAP with SMAC.

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfonyl" means a —$SO_2$—R group in which R is H, alkyl, a carbocycle, a heterocycle, carbocycle-substituted alkyl or heterocycle-substituted alkyl wherein the alkyl, alkoxy, carbocycle and heterocycle are as defined herein. Particular sulfonyl groups are alkylsulfonyl (i.e. —$SO_2$-alkyl), for example methylsulfonyl; arylsulfonyl, for example phenylsulfonyl; aralkylsulfonyl, for example benzylsulfonyl.

The present invention provides novel compounds having the general formula $U_1$-M-$U_2$ wherein M is a linking group covalently joining $U_1$ and $U_2$.

$U_1$ and $U_2$ have the general formula (I)

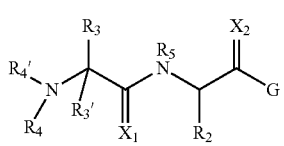

I

M is a linking group covalently joining $U_1$ and $U_2$. In a particular embodiment M is a linking group covalently joining $R_2$, $R_3$, $R_4$, $R_5$ or G of $U_1$ to $R_2$, $R_3$, $R_4$, $R_5$ or G of $U_2$. In a particular embodiment M covalently joins G of $U_1$ to G of $U_2$. In a particular embodiment M is a linking group covalently joining $R_2$ of $U_1$ to $R_2$ of $U_2$.

In a particular embodiment M is alkylene optionally substituted with alkyl and hydroxyl and wherein one or more non-adjacent methylene groups is optionally replaced with —O— or —NH—. In a particular embodiment said alkylene is unsaturated or partially unsaturated. In a particular embodiment M is —$CH_2$— [C≡C]$_{0-4}$—$CH_2$—. In a particular embodiment M is —$CH_2$—C≡C—$CH_2$—.

In a particular embodiment M is —$(CR_{10}R_{11})_{1-14}$— wherein $R_{10}$ and $R_{11}$ are independently alkyl or hydroxyl. In a particular embodiment $R_{10}$ and $R_{11}$ are both methyl. In a particular embodiment one of $R_{10}$ and $R_{11}$ is hydroxyl. In a particular embodiment M is —$(CH_2)_{1-6}$—(CHOH)—$(CH_2)_{1-6}$—. In a particular embodiment M is —$(CH_2)_{1-6}$—$(C(CH_3)_2)$—$(CH_2)_{1-6}$—. In a particular embodiment M is —$(CH_2)_{1-14}$—, for example —$(CH_2)_{2-12}$—, —$(CH_2)_{4-8}$—, —$(CH_2)_{4-6}$—, —$(CH_2)_{1}$—, —$(CH_2)_{2}$—, —$(CH_2)_{3}$—, —$(CH_2)_{4}$—, —$(CH_2)_{5}$—, —$(CH_2)_{6}$—, —$(CH_2)_{7}$—, —$(CH_2)_{8}$—, —$(CH_2)_{9}$—, —$(CH_2)_{10}$—, —$(CH_2)_{11}$— and —$(CH_2)_{12}$—.

In a particular embodiment M is —$(CH_2)_q[(CH_2)_r$—O—$]_s$—$(CH_2)_t$— wherein q is 1-2, r is 1-4, s is 0-8 and t is 1-4. In a particular embodiment M is —$(CH_2)_{1-4}$—[O—$(CH_2)_{1-4}]_{1-8}$—$(CH_2)_{0-4}$—. In a particular embodiment M is —$(CH_2)_3$—[O—$(CH_2)_2]_3$—$CH_2$—. In a particular embodiment M is —$(CH_2)_2$—[O—$(CH_2)_2]_2$—. In a particular embodiment M is —(—$CH_2$)$_{1-4}$—[NH—$(CH_2)_{1-4}]_{1-8}$—$(CH_2)_{0-4}$—. In a particular embodiment M is —$(CH_2)_3$[NH—$(CH_2)_2$]—$CH_2$—.

G is selected from the group consisting of IVa to IVe:

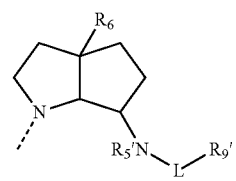

IVa

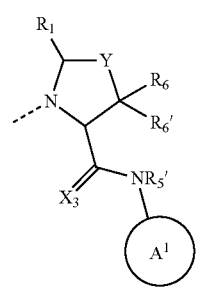

IVb

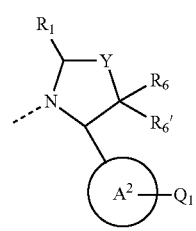

IVc

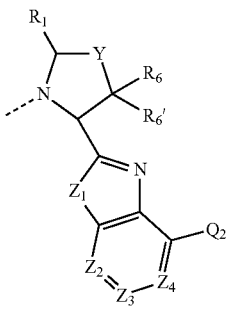

IVd

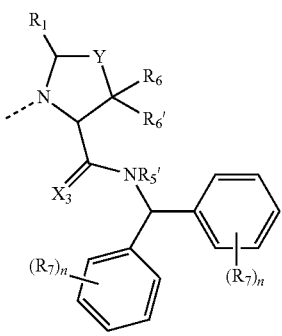

IVe and $A^1$, $A^2$, L, $Q_1$, $Q_2$, $X_3$, Y, $Z_1$, $Z_2$, $Z_3$, $Z_4$, $R_1$, $R_5'$, $R_6$, $R_6'$, $R_7$, $R_9'$ and n are as described herein. In a particular embodiment G is IVa. In a particular embodiment G is IVb. In a particular embodiment G is IVc. In a particular embodiment G is IVd. In a particular embodiment G is We.

$A^1$ is a 5-member heterocycle comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle. In an embodiment, the 5-member heterocycle ring $A^1$ groups are optionally substituted with amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, haloalkyl, amino, nitro, cycloalkyl, aryl or a heterocycle. In a particular embodiment ring $A^1$ is aromatic. In a particular embodiment ring $A^1$ has the formula IIa or IIb:

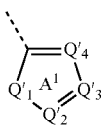

IIa

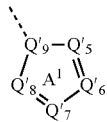

IIb wherein $Q'_1$ is $NR_8$, O or S; $Q'_2$, $Q'_3$, $Q'_4$, $Q'_5$, $Q'_6$, $Q'_7$, and $Q'_8$ are independently $CR_9$ or N; wherein $R_9$ is H, amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, haloalkyl, amino, nitro, cycloalkyl, aryl or a heterocycle; $R_8$ is H, alkyl, acyl, aryl, cycloalkyl or a heterocycle; wherein each alkyl, aryl, cycloalkyl and heterocycle is optionally substituted with hydroxyl, halogen, mercapto, carboxyl, alkyl, haloalkyl, amino, nitro, cycloalkyl, aryl or a heterocycle; and $Q'_9$ is CH or N. In a particular embodiment, ring $A^1$ is a group of formula IIa. In a particular embodiment ring $A^1$ is a group of formula IIa wherein $Q'_4$ is $CR_9$ wherein $R_9$ is aryl or heteroaryl optionally substituted as described above. In a particular embodiment ring $A^1$ is a group of formula IIa wherein $Q'_4$ is $CR_9$ and $R_9$ is phenyl. In a particular embodiment, ring $A^1$ is a group of formula IIa wherein $Q'_4$ is $CR_9$ and $R_9$ is phenyl and $Q'_3$ is CH or CF. In another embodiment, ring $A^1$ is a group of formula IIa wherein $Q'_4$ is $CR_9$ and $R_9$ is pyridin-2-yl. In another embodiment, ring $A^1$ is a group of formula IIa wherein $Q'_4$ is $CR_9$, $R_9$ is pyridin-2-yl and $Q'_3$ is C-Me.

In another embodiment, ring $A^1$ according to IIa or IIb is a pyrrole ring optionally substituted with alkyl, aryl, aralkyl, cycloalkyl, cycloalkylalkyl, a heterocycle or a heterocyclealkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

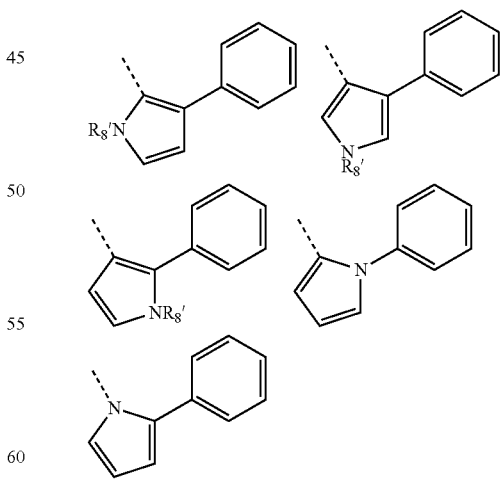

wherein $R_8'$ is H, alkyl (for example methyl, ethyl or propyl) or acyl (for example acetyl). In a particular embodiment $R_8'$ is H.

In another embodiment ring $A^1$ is furan optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

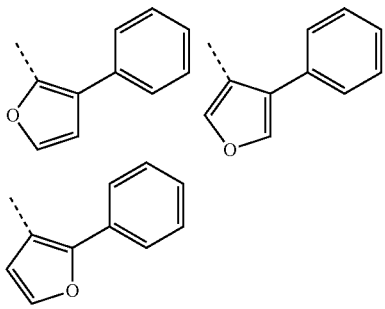

In another embodiment ring $A^1$ is thiophene optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

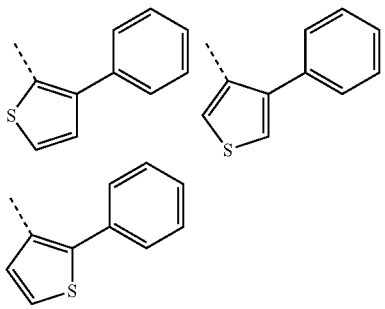

In another embodiment ring $A^1$ is pyrazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

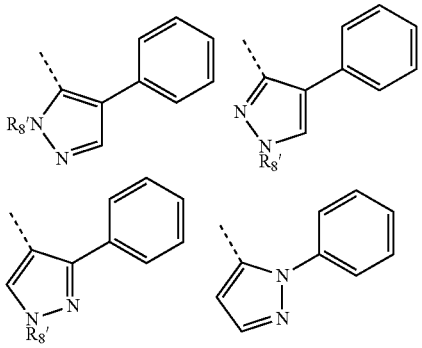

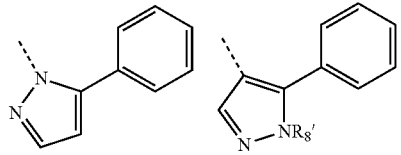

wherein $R_8'$ is H, alkyl (for example methyl, ethyl or propyl) or acyl (for example acetyl). In a particular embodiment $R_8'$ is H.

In another embodiment ring $A^1$ is imidazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring A is selected from the group consisting of:

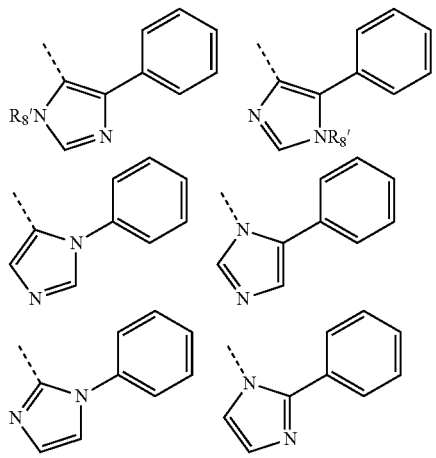

wherein $R_8'$ is H, alkyl (for example methyl, ethyl or propyl) or acyl (for example acetyl). In a particular embodiment $R_8'$ is H.

In another embodiment ring $A^1$ is oxazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

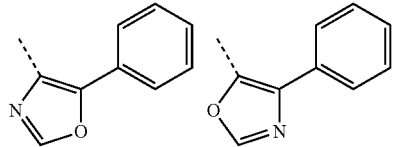

In another embodiment ring $A^1$ is isoxazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

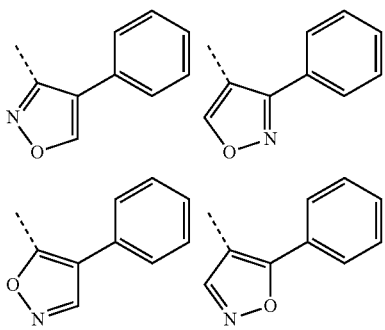

In another embodiment ring $A^1$ is thiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

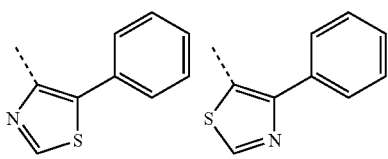

In another embodiment ring $A^1$ is isothiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

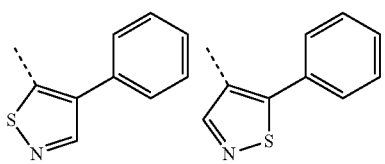

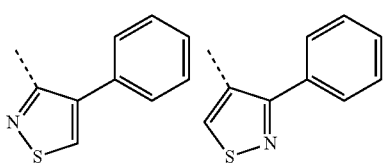

In another embodiment ring $A^1$ is 1,2,3-triazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

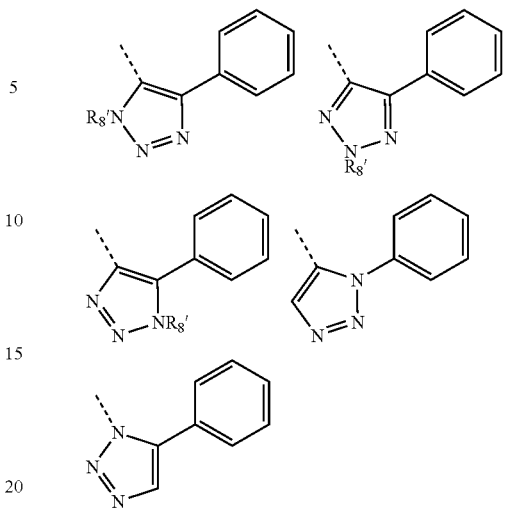

wherein $R_8'$ is H, alkyl (for example methyl, ethyl or propyl) or acyl (for example acetyl). In a particular embodiment $R_8'$ is H.

In another embodiment ring $A^1$ is 1,2,4-triazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

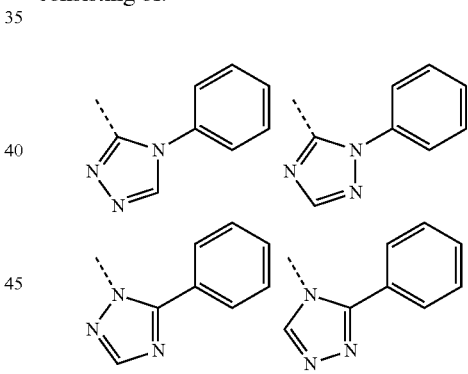

In another embodiment ring $A^1$ is oxadiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

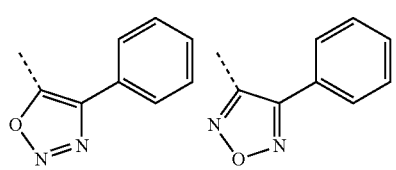

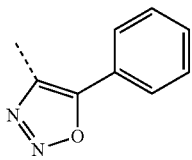

In another embodiment ring $A^1$ is thiadiazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

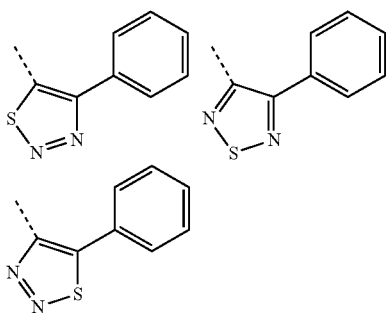

In another embodiment ring $A^1$ is tetrazole optionally substituted with alkyl, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring $A^1$ is substituted with an aryl or heteroaryl group. In a particular embodiment, ring $A^1$ is selected from the group consisting of:

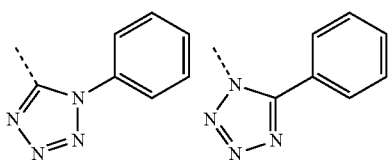

In a particular embodiment ring $A^1$ is:

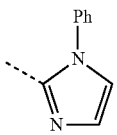

In a particular embodiment ring $A^1$ is:

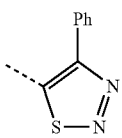

$A^2$ is a 5-member aromatic heterocycle incorporating 1 to 4 heteroatoms N, O or S which is substituted with group $Q_1$ and is optionally further substituted with one or more $R_7$ (for substitutions at a ring carbon atom) and one or more $R_8$ (for substitutions at a ring nitrogen). In a particular embodiment ring $A^2$ has the general formula II:

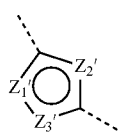

II

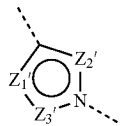

II' wherein $Z_{1'}$ is $NR_8$, O or S; and $Z_{2'}$, $Z_{3'}$ and $Z_{4'}$ are each independently N or $CR_7$. Group $Q_1$ is attached to ring $A^2$ of formula II and II' at the ring member between $Z_{2'}$ and $Z_{3'}$. In a particular embodiment $Z_{1'}$ is S. In a particular embodiment $Z_{1'}$ is O. In another particular embodiment $Z_{1'}$ is $NR_8$, wherein $R_8$ is as defined herein. In a particular embodiment $Z_{1'}$ is $NR_8$ wherein $R_8$ is H. In another particular embodiment $Z_{1'}$ is $NR_8$ wherein $R_8$ is Me. In another embodiment $Z_{1'}$ is O or S while $Z_{2'}$ is N and $Z_{3'}$ is N or $CR_7$. In a particular embodiment $Z_{1'}$ is S while $Z_{2'}$ is N and $Z_{3'}$ is $CR_7$. In a particular embodiment $Z_{1'}$ is S while $Z_{2'}$ is N and $Z_{3'}$ is CH.

In a particular embodiment, ring $A^2$ (shown together with $Q_1$) is an aromatic heterocycle selected from the group consisting of IIa¹-IIcc¹:

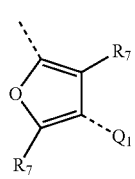

IIa¹

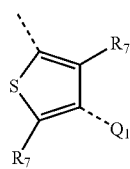

IIb¹

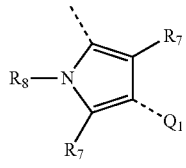

IIc¹

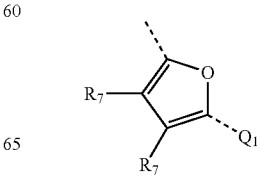

IIc¹·¹

-continued
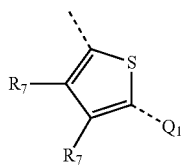                IId¹
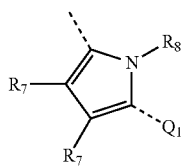                IIe¹
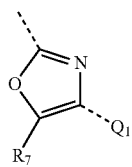                IIf¹
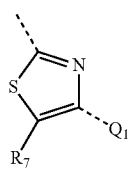                IIg¹
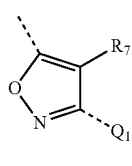                IIh¹
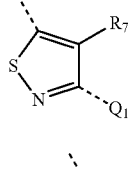                IIi¹
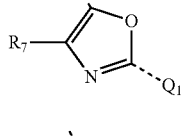                IIj¹
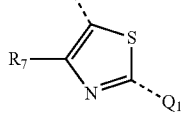                IIk¹
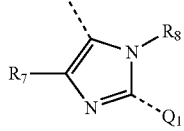                IIl¹
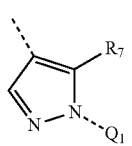               IIm¹
-continued
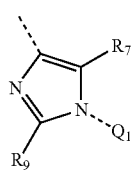               IIn¹
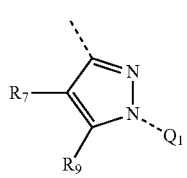               IIo¹
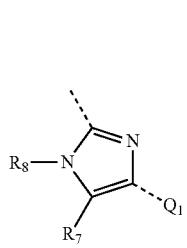               IIp¹
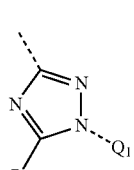               IIq¹
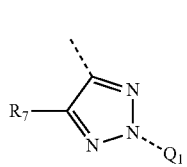               IIr¹
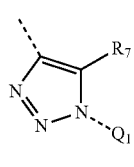               IIs¹
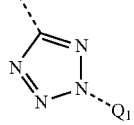               IIt¹
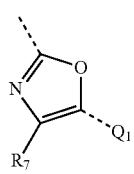               IIu¹
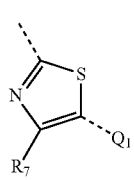               IIv¹

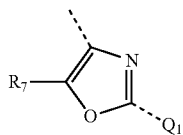

IIx¹

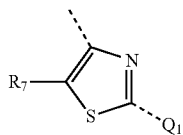

IIy¹

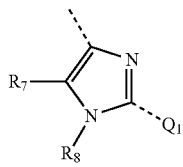

IIz¹

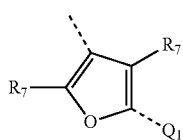

IIaa¹

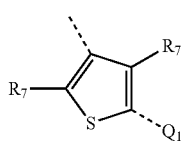

IIbb¹

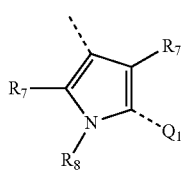

IIcc¹

$X_1$ and $X_2$ are each independently O or S. In a particular embodiment, $X_1$ and $X_2$ are both O. In another particular embodiment $X_1$ and $X_2$ are both S. In another particular embodiment, $X_1$ is S while $X_2$ is O. In another particular embodiment, $X_1$ is O while $X_2$ is S.

Y is a bond, $(CR_7R_7)_{n'}$, O or S. In an embodiment Y is a bond, $(CR_7R_7)_{n'}$, O or S; wherein n' is 1 or 2 and $R_7$ is as defined herein or is H, halogen, alkyl, aryl, aralkyl, amino, arylamino, alkylamino, aralkylamino, alkoxy, aryloxy or aralkyloxy. In a particular embodiment, Y is $(CHR_7)_{n'}$, O or S; wherein n' is 1 or 2 and $R_7$ is H, halogen, alkyl, aryl, aralkyl, amino, arylamino, alkylamino, aralkylamino, alkoxy, aryloxy or aralkyloxy. In a particular embodiment, Y is $CH_2$. In a particular embodiment n' is 1. In a particular embodiment Y is a bond. In a particular embodiment n' is 1 and Y is $CHR_7$ wherein $R_7$ is aralkyloxy, for example benzyloxy. In a particular embodiment n' is 1 and Y is $CHR_7$ wherein $R_7$ is F. In a particular embodiment n' is 1 and Y is $CHR_7$ wherein $R_7$ is aralkylamino, for example benzylamino. In another particular embodiment Y is O. In another particular embodiment Y is S.

$Z_1$ is $NR_8$, O, S, SO or $SO_2$; wherein $R_8$ is defined herein. In an embodiment, $Z_1$ is $NR_8$, O or S. In an embodiment, $Z_1$ is $NR_8$ wherein $R_8$ is H, alkyl, aryl or aralkyl. In a particular embodiment $Z_1$ is $NR_8$ wherein $R_8$ is benzyl. In a particular embodiment, $Z_1$ is $NR_8$ wherein $R_8$ is Me. In a particular embodiment, $Z_1$ is $NR_8$ wherein $R_8$ is H. In a particular embodiment, $Z_1$ is O. In a particular embodiment, $Z_1$ is S.

$Z_2$, $Z_3$ and $Z_4$ are independently $CQ_2$ or N. In a particular embodiment, $Z_2$ is N. In a particular embodiment, $Z_3$ is N. In a particular embodiment, $Z_4$ is N. In an embodiment, $Z_2$, $Z_3$ and $Z_4$ are $CQ_2$. In an embodiment, $Z_2$ is N, $Z_3$ is $CQ_2$ and $Z_4$ is $CQ_2$. In an embodiment, $Z_2$ is $CQ_2$, $Z_3$ is N and $Z_4$ is $CQ_2$. In an embodiment, $Z_2$ is $CQ_2$, $Z_3$ is $CQ_2$ and $Z_4$ is N. In an embodiment, $Z_2$ is N, $Z_3$ is $CQ_2$ and $Z_4$ is N.

$Q_1$ and $Q_2$ are independently H, alkyl, a carbocycle, a heterocycle; wherein one or more $CH_2$ or CH groups of an alkyl is optionally replaced with —O—, —S—, —S(O)—, $S(O)_2$, —$N(R_8)$—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—; and wherein any of the foregoing alkyl, carbocycle and heterocycle is optionally substituted with one or more hydroxyl, alkoxy, acyl, halogen, mercapto, oxo, carboxyl, acyl, halo-substituted alkyl, amino, cyano nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment $Q_1$ and $Q_2$ are independently is a carbocycle or heterocycle optionally substituted with halogen, amino, oxo, alkyl, a carbocycle or a heterocycle; wherein one or more $CH_2$ or CH groups of an alkyl is optionally replaced with —O—, —S—, —S(O)—, $S(O)_2$, —$N(R_8)$—, —C(O)—, —C(O)—$NR_8$—, —$NR_8$—C(O)—, —$SO_2$—$NR_8$—, —$NR_8$—$SO_2$—, —$NR_8$—C(O)—$NR_8$—, —$NR_8$—C(NH)—$NR_8$—, —$NR_8$—C(NH)—, —C(O)—O— or —O—C(O)—; and wherein said alkyl, carbocycle or heterocycle is optionally substituted with halogen, amino, hydroxyl, mercapto, carboxyl, alkoxy, alkoxyalkoxy, hydroxyalkoxy, alkylthio, acyloxy, acyloxyalkoxy, alkylsulfonyl, alkylsulfonylalkyl, alkylsulfinyl, and alkylsulfinylalkyl.

In a particular embodiment, $Q_1$ and $Q_2$ are independently a carbocycle or heterocycle selected from the group consisting of III-1 to III-16

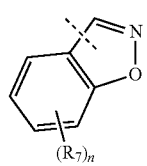

III-1

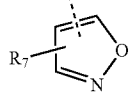

III-2

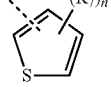

III-3

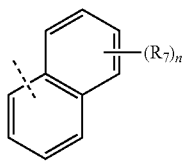
III-4
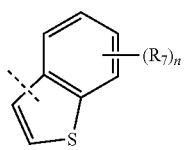
III-5
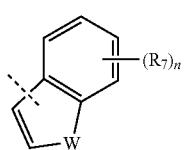
III-6
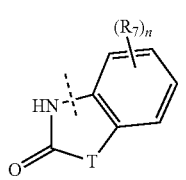
III-7
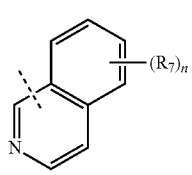
III-8
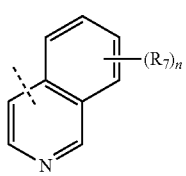
III-9
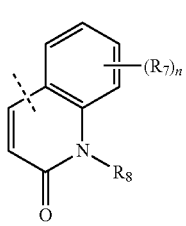
III-10
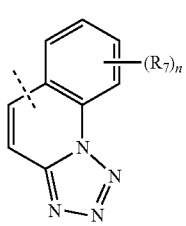
III-11
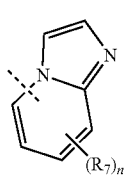
III-12
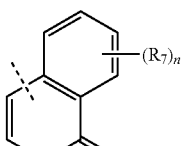
III-13
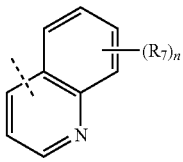
III-14
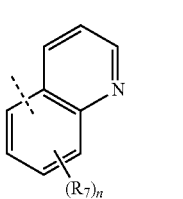
III-15
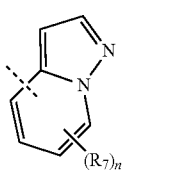
III-16
wherein n is 1-4, for example 1-3, for example 1-2, for example 1; T is O, S, $NR_8$ or $CR_7R_7$; W is O, $NR_8$ or $CR_7R_7$; and $R_7$ and $R_8$ are as defined herein.
In a particular embodiment, $Q_1$ and $Q_2$ are independently a carbocycle or heterocycle selected from the group consisting of IIIa to IIIs:
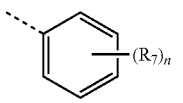
IIIa
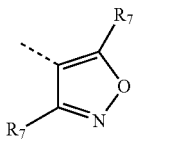
IIIb
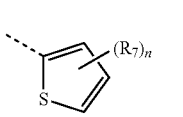
IIIc
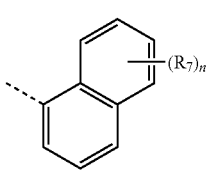
IIId

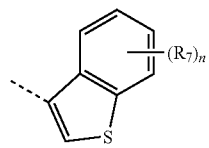
IIIe

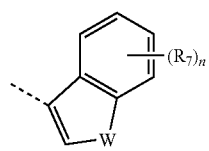
IIIf

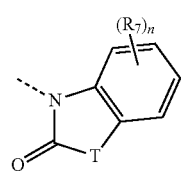
IIIg

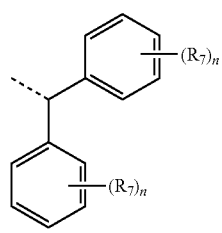
IIIh

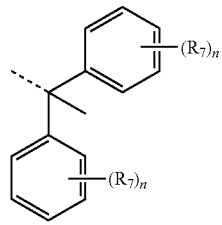
IIIi

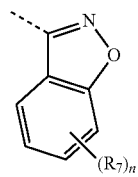
IIIj

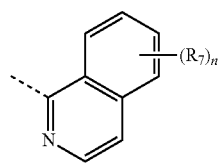
IIIk

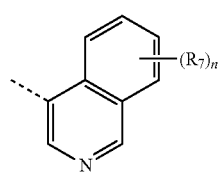
IIIl

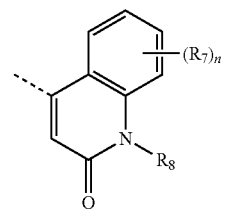
IIIm

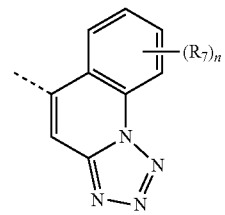
IIIn

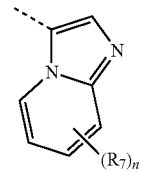
IIIo

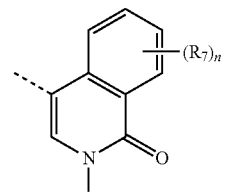
IIIp

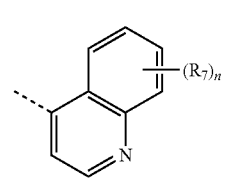
IIIq

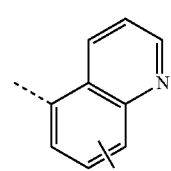
IIIr

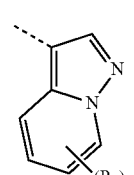
IIIs wherein n is 1-4, for example 1-3, for example 1-2, for example 1; T is O, S, $NR_8$ or $CR_7R_7$; W is O, $NR_8$ or $CR_7R_7$; and $R_7$ and $R_8$ are as defined herein. In a particular embodiment $Q_1$ and $Q_2$ are independently any one of IIIa-IIIi wherein $R_8$ is H and $R_7$ is selected from the group consisting of H, F, Cl, Me, methoxy, hydroxyethoxy, methoxyethoxy, acetoxyethoxy, methylsulfonyl methylsulfonylmethyl, phenyl and morpholin-4-yl. In another embodiment $Q_1$ and $Q_2$ are independently IIId. In a particular embodiment $Q_1$ and $Q_2$ are independently IIId which is substituted at the 4-position with R$_7$. In another particular embodiment Q$_1$ and Q$_2$ are independently IIId which is substituted at the 5-position with R$_7$. In a particular embodiment Q$_1$ and Q$_2$ are independently F, Me, iPr, phenyl, phenyl substituted as follows: 2-Cl, 3-Cl, 4-Cl, 2-F, 3-F or 4-F substituted, benzyl, pyrid-3-yl or pyrid-4-yl.

R$_1$ is H, OH or alkyl; or R$_1$ and R$_2$ together form a 5-8 member heterocycle. In a particular embodiment, R$_1$ is H. In a particular embodiment, R$_1$ and R$_2$ together form a 6-member ring. In a particular embodiment, R$_1$ and R$_2$ together form a 7-member ring. In another particular embodiment, R$_1$ and R$_2$ together form an 8-member ring. In another particular embodiment, R$_1$ and R$_2$ together form a 7-member ring while Y is S. In another particular embodiment, R$_1$ is H, while Y is CH$_2$. In another particular embodiment, R$_1$ is H, while Y is S. In another particular embodiment, R$_1$ is H, while Y is O.

R$_2$ is alkyl, a carbocycle, carbocyclylalkyl, a heterocycle or heterocyclylalkyl each optionally substituted with halogen, hydroxyl, oxo, thione, mercapto, carboxyl, alkyl, haloalkyl, alkoxy, alkylthio, acyl, hydroxyacyl, alkoxyacyl, sulfonyl, amino and nitro. In a particular embodiment R$_2$ is alkyl, a carbocycle, carbocyclylalkyl, a heterocycle or heterocyclylalkyl each optionally substituted with halogen, hydroxyl, oxo, mercapto, thione, carboxyl, alkyl, haloalkyl, alkoxy, alkylthio, acyl, hydroxyacyl, methoxyacyl, sulfonyl, amino and nitro. In an embodiment R$_2$ is alkyl, a carbocycle, carbocyclylalkyl, a heterocycle or heterocyclylalkyl each optionally substituted with halogen, hydroxyl, mercapto, carboxyl, alkyl, alkoxy, amino and nitro. In a particular embodiment R$_2$ is alkyl, cycloalkyl, cycloalkylalkyl, aryl, aralkyl, a heterocycle or heterocyclylalkyl. In a particular embodiment R$_2$ is alkyl, cycloalkyl or a heterocycle. In a particular embodiment R$_2$ is selected from the group consisting of t-butyl, isopropyl, cyclohexyl, tetrahydropyran-4-yl, N-methylsulfonylpiperidin-4-yl, tetrahydrothiopyran-4-yl, tetrahydrothiopyran-4-yl (in which the S is in oxidized form SO or SO$_2$), cyclohexan-4-one, 4-hydroxycyclohexane, 4-hydroxy-4-methylcyclohexane, 1-methyl-tetrahydropyran-4-yl, 2-hydroxyprop-2-yl, but-2-yl, thiophen-3-yl, piperidin-4-yl, N-acetylpiperidin-4-yl, N-hydroxyethylpiperidin-4-yl, N-(2-hydroxyacetyl) piperidin-4-yl, N-(2-methoxyacetyl)piperidin-4-yl, pyridin-3-yl, phenyl and 1-hydroxyeth-1-yl. In an embodiment of the invention R$_2$ is t-butyl, isopropyl, cyclohexyl, cyclopentyl, phenyl or tetrahydropyran-4-yl. In a particular embodiment, R$_2$ is phenyl. In a particular embodiment, R$_2$ is cyclohexyl. In another embodiment R$_2$ is tetrahydropyran-4-yl. In another particular embodiment, R$_2$ is isopropyl (i.e. the valine amino acid side chain). In another particular embodiment, R$_2$ is t-butyl. In a particular embodiment R$_2$ is oriented such that the amino acid, or amino acid analogue, which it comprises is in the L-configuration.

R$_3$ is H or alkyl optionally substituted with halogen or hydroxyl; or R$_3$ and R$_4$ together form a 3-6 heterocycle. In an embodiment R$_3$ is H or alkyl; or R$_3$ and R$_4$ together form a 3-6 heterocycle. In an embodiment R$_3$ is H or methyl, ethyl, propyl or isopropyl. In a particularly particular embodiment R$_3$ is H or methyl. In another particular embodiment R$_3$ is methyl. In another particular embodiment R$_3$ is fluoromethyl. In another particular embodiment, R$_3$ is ethyl. In another particular embodiment R$_3$ is hydroxyethyl. In a particular embodiment R$_3$ is fluoromethyl. In a particular embodiment R$_3$ is hydroxyethyl. In another embodiment R$_3$ is oriented such that the amino acid, or amino acid analogue, which it comprises is in the L-configuration. In a particular embodiment R$_3$ and R$_4$ together with the atoms from which they depend form a 3-6 heterocycle. In a particular embodiment R$_3$ and R$_4$ together form an azetidine ring. In a particular embodiment R$_3$ and R$_4$ together form a pyrrolidine.

R$_3$' is H, or R$_3$ and R$_3$' together form a 3-6 carbocycle. In an embodiment, R$_3$' is H. In another embodiment R$_3$ and R$_3$' together form a 3-6 carbocycle, for example a cyclopropyl ring. In a particular embodiment R$_3$ and R$_3$' are both methyl.

R$_4$ and R$_4$' are independently H, hydroxyl, amino, alkyl, carbocycle, carbocycloalkyl, carbocycloalkyloxy, carbocycloalkyloxycarbonyl, heterocycle, heterocycloalkyl, heterocycloalkyloxy or heterocycloalkyloxycarbonyl; wherein each alkyl, carbocycloalkyl, carbocycloalkyloxy, carbocycloalkyloxycarbonyl, heterocycle, heterocycloalkyl, heterocycloalkyloxy and heterocycloalkyloxycarbonyl is optionally substituted with halogen, hydroxyl, mercapto, carboxyl, alkyl, alkoxy, amino, imino and nitro; or R$_4$ and R$_4$' together form a heterocycle. In an embodiment R$_4$ and R$_4$' are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro; or R$_4$ and R$_4$' together form a heterocycle. In a particular embodiment R$_4$ and R$_4$' together form a heterocycle, for example an azetidine ring, or a pyrrolidine ring. In a particular embodiment R$_4$ and R$_4$' are both H. In another particular embodiment R$_4$ is methyl and R$_4$' is H. In a particular embodiment one of R$_4$ and R$_4$' is hydroxyl (OH) while the other is H. In another embodiment, one of R$_4$ and R$_4$' is amino, such as NH$_2$, NHMe and NHEt, while the other is H. In a particular embodiment, R$_4$' is H and R$_4$ is H, alkyl, aryl, aralkyl, cycloalkyl, cycloalkylalkyl, heteroaryl or heteroarylalkyl. In a particular embodiment R$_4$ is a group selected from the group consisting of:

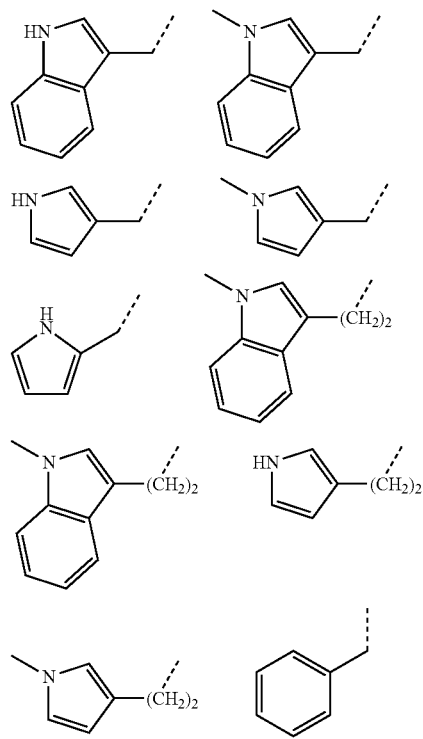

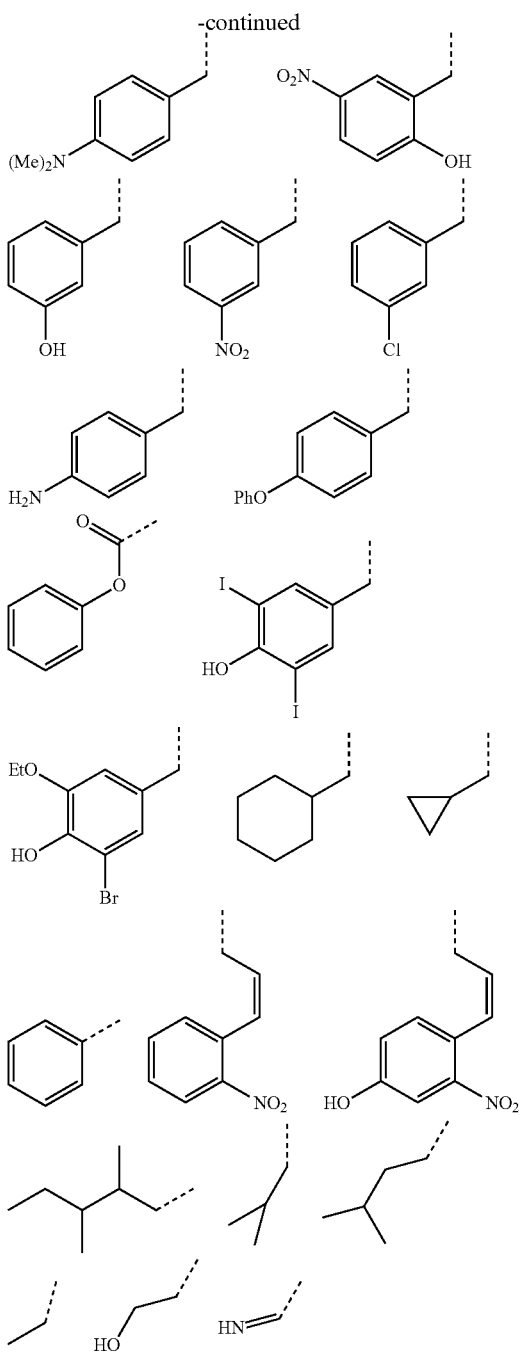

$R_5$ is H or alkyl. In a particular embodiment, $R_5$ is H or methyl. In a particular embodiment, $R_5$ is H. In another particular embodiment, $R_5$ is methyl.

$R_6$ and $R_6'$ are each independently H, alkyl, aryl or aralkyl. In a particular embodiment, $R_6$ is alkyl, for example methyl. In another particular embodiment, $R_6$ is aryl, for example phenyl. In another particular embodiment, $R_6$ is aralkyl, for example benzyl. In a particular embodiment $R_6$ and $R_6'$ are the same, for example both alkyl, e.g. both methyl. In another particular embodiment $R_6$ is methyl and $R_6'$ is H.

$R_7$ in each occurrence is independently H, cyano, hydroxyl, mercapto, halogen, nitro, carboxyl, amidino, guanidino, alkyl, a carbocycle, a heterocycle or —U—V; wherein U is —O—, —S—, —S(O)—, $S(O)_2$, —N($R_8$)—, —C(O)—, —C(O)—N$R_8$—, —N$R_8$—C(O)—, —SO$_2$—N$R_8$—, —N$R_8$—SO$_2$—, —N$R_8$—C(O)—N$R_8$—, —N$R_8$—C(NH)—N$R_8$—, —N$R_8$—C(NH)—, —C(O)—O— or —O—C(O)— and V is alkyl, a carbocycle or a heterocycle; and wherein one or more $CH_2$ or CH groups of an alkyl is optionally replaced with —O—, —S—, —S(O)—, $S(O)_2$, —N($R_8$)—, —C(O)—, —C(O)—N$R_8$—, —N$R_8$—C(O)—, —SO$_2$—N$R_8$—, —N$R_8$—SO$_2$—, —N$R_8$—C(O)—N$R_8$—, —N$R_8$—C(NH)—N$R_8$—, —N$R_8$—C(NH)—, —C(O)—O— or —O—C(O)—; and an alkyl, carbocycle and heterocycle is optionally substituted with hydroxyl, alkoxy, acyl, halogen, mercapto, oxo, carboxyl, acyl, halo-substituted alkyl, amino, cyano, nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In an embodiment $R_7$ is H, halogen, alkyl, aryl, aralkyl, amino, arylamino, alkylamino, aralkylamino, alkoxy, aryloxy or aralkyloxy.

$R_8$ is H, alkyl, a carbocycle or a heterocycle wherein one or more $CH_2$ or CH groups of said alkyl is optionally replaced with —O—, —S—, —S(O)—, $S(O)_2$, —N($R_8$), or —C(O)—; and said alkyl, carbocycle and heterocycle is optionally substituted with hydroxyl, alkoxy, acyl, halogen, mercapto, oxo (=O), carboxyl, acyl, halo-substituted alkyl, amino, cyano nitro, amidino, guanidino an optionally substituted carbocycle or an optionally substituted heterocycle. Substituents of the "optionally substituted carbocycle" and "optionally substituted heterocycle" are as defined herein. In a particular embodiment such carbocycle and heterocycle groups are substituted with hydroxyl, alkyl, alkoxy, acyl, halogen, mercapto, oxo, carboxyl, acyl, halo-substituted alkyl, amino, cyano, nitro, amidino and guanidino. In a particular embodiment $R_8$ is H, alkyl, or acyl. In an embodiment $R_8$ is methyl. In another embodiment $R_8$ is acetyl. In a particular embodiment $R_8$ is H. In an embodiment $R_7$ is H, halogen, amino, hydroxyl, carboxyl, alkyl, haloalkyl or aralkyl. In a particular embodiment $R_7$ is halogen, for example Cl or F. In a particular embodiment $R_7$ is H. It is understood that substitutions defined for $R_7$ and $R_8$ as well as all other variable groups herein are subject to permissible valency.

$R_9'$ is $Q_1$ or $Q_2$ as defined herein. In an embodiment, $R_9'$ is alkyl, a carbocycle, carbocycle-substituted alkyl, a heterocycle or heterocycle-substituted alkyl, wherein each is optionally substituted with halogen, hydroxyl, mercapto, carboxyl, alkyl, haloalkyl, alkoxy, alkylsulfonyl, amino, nitro, aryl and heteroaryl. In a particular embodiment $R_9'$ is alkyl, aryl, aralkyl, cycloalkyl, cycloalkylalkyl, heteroaryl or heteroaralkyl wherein each is optionally substituted with halogen, hydroxyl, mercapto, carboxyl, alkyl, haloalkyl amino, nitro, aryl and heteroaryl.

n is 1 to 4. In an embodiment n is 1. In an embodiment n is 2. In an embodiment n is 3. In an embodiment n is 4.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention. In a particular embodiment, compounds of the invention have the following stereochemical configuration of formula I' in which the monomer have the same stereochemistry orientation:

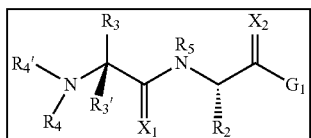
I' wherein $X_1$, $X_2$, Y, $Z_1$, $Z_2$, $Z_3$, Q $R_1$, $R_2$, $R_3$, $R_3'$, $R_4$, $R_4'$, $R_5$, $R_6$ and $R_6'$ are as described herein and $G_1$ and $G_2$ are independently IVa', IVb', IVc', IVd' or IVe':

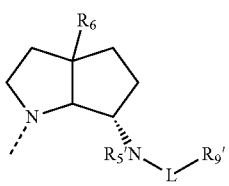
IVa'

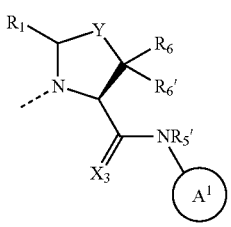
IVb'

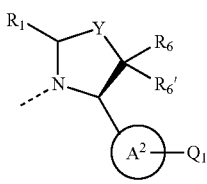
IVc'

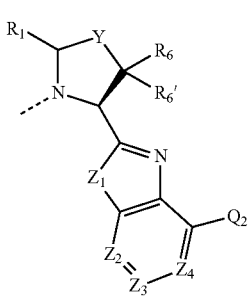
IVd'

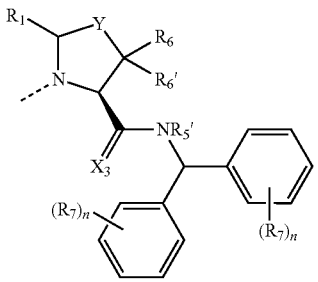
IVe' wherein $A^1$, $A^2$, L, $Q_1$, $Q_2$, $X_3$, Y, $Z_1$, $Z_2$, $Z_3$, $Z_4$, $R_1$, $R_5'$, $R_6$, $R_6'$, $R_7$, $R_9'$ and n are as described herein. In a particular embodiment $G_1$ and $G_2$ are IVa'. In a particular embodiment $G_1$ and $G_2$ are IVb'. In a particular embodiment $G_1$ and $G_2$ are IVc'. In a particular embodiment $G_1$ and $G_2$ are IVd'. In a particular embodiment $G_1$ and $G_2$ are IVe'.

In particular embodiments, $G_1$ and $G_2$ are independently II'a-II'e

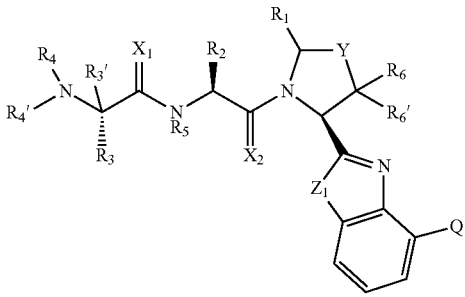
II'a

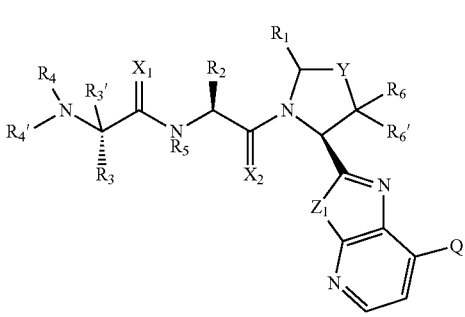
II'b

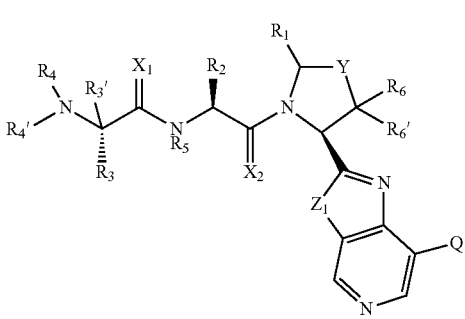
II'c

II'd
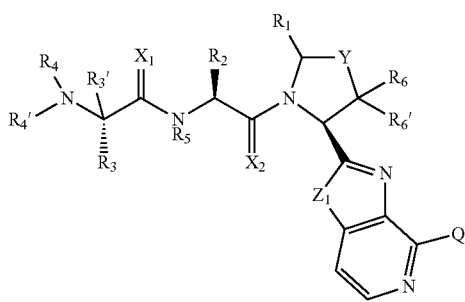
II'e
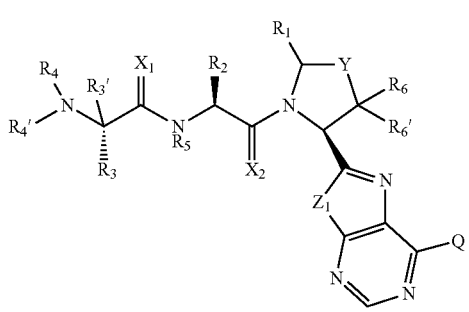
wherein $X_1$, $X_2$, Y, $Z_1$, Q, $R_1$, $R_2$, $R_3$, $R_4$, $R_4'$, $R_5$, $R_6$ and $R_6'$ are as described herein.
In a particular embodiment compounds of the invention have the formula V or Va
V
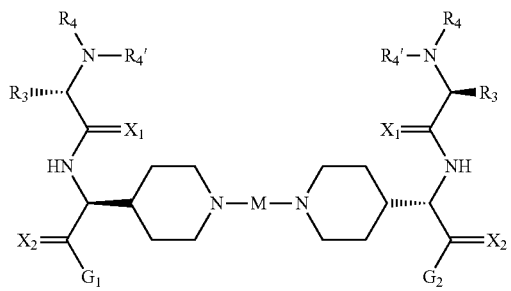
Va
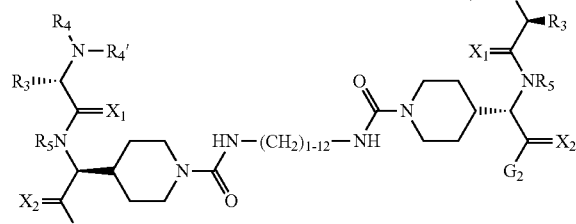
In a particular embodiment compounds of the invention have the formula VI or VIa
VI
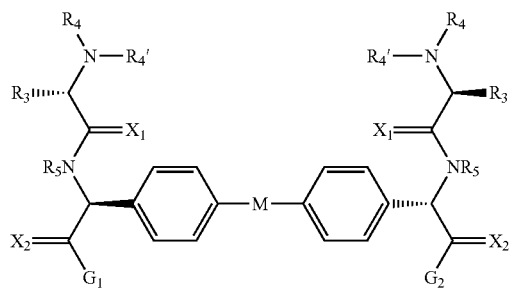
VIa
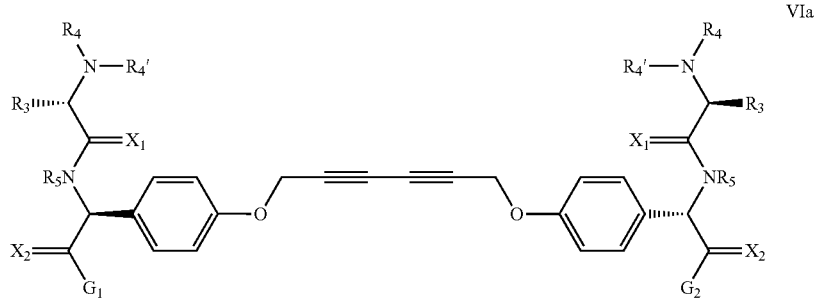

In a particular embodiment compounds of the invention have the formula VII or VIIa
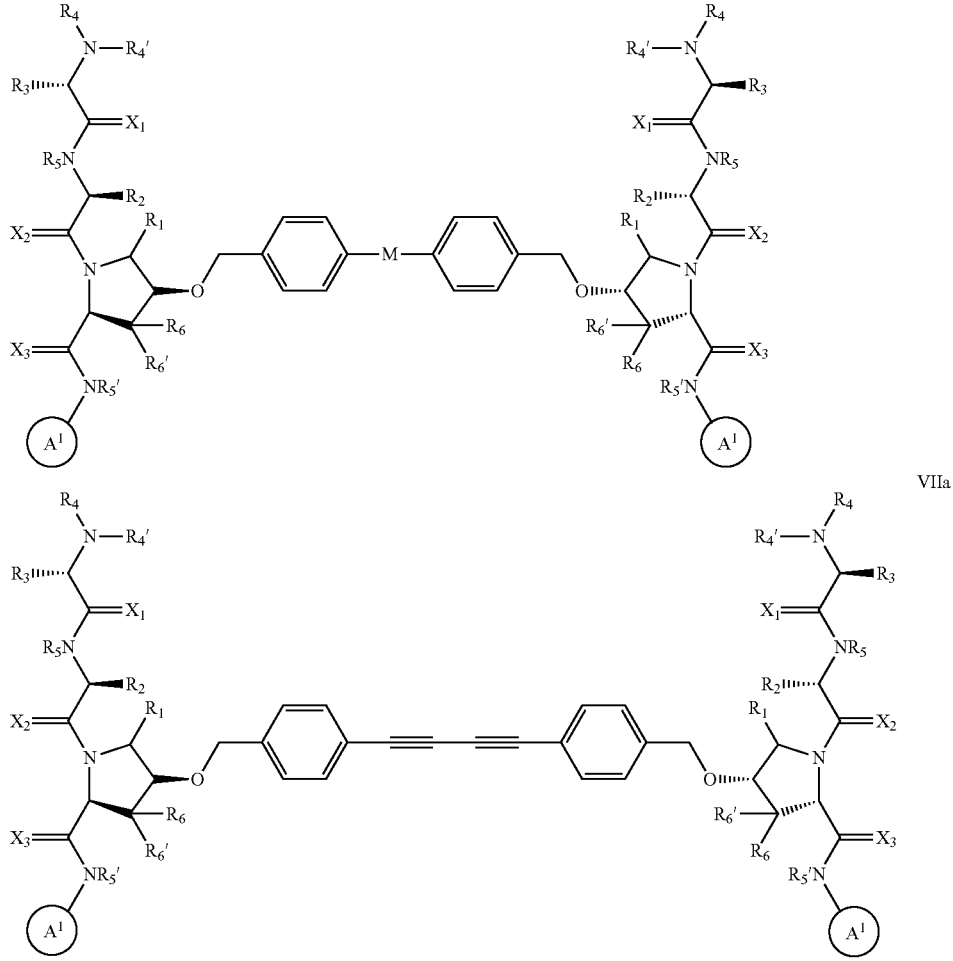
In a particular embodiment compounds of the invention have the formula VIII or VIIIa
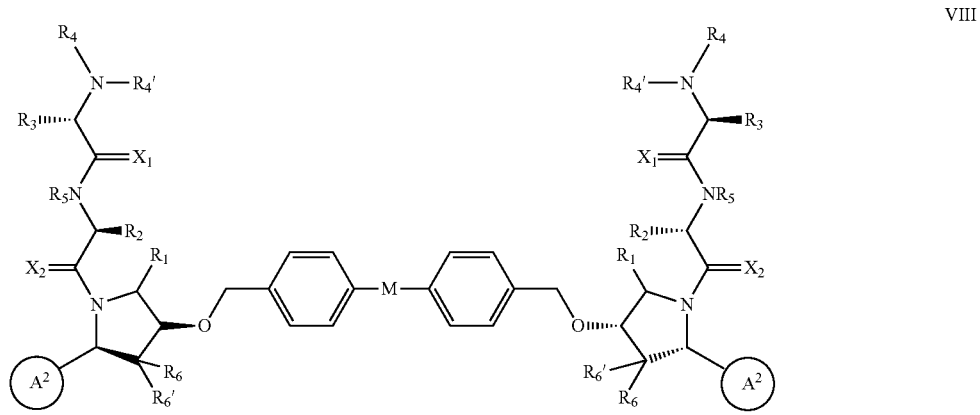

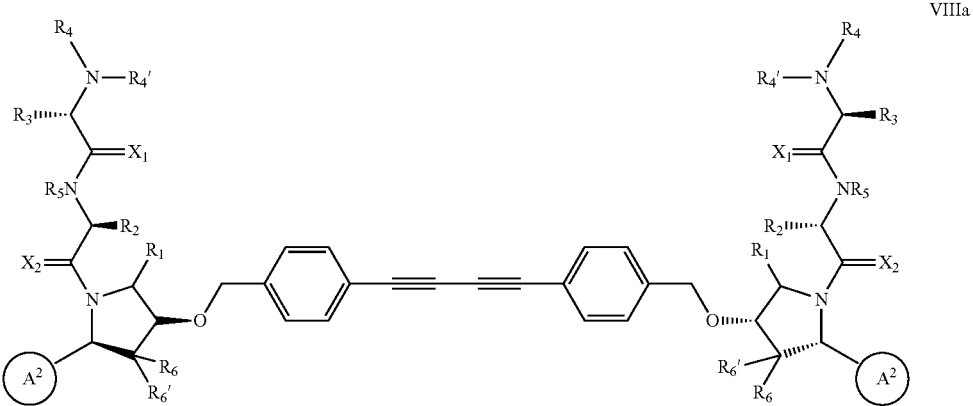
In a particular embodiment compounds of the invention have the formula IX or IXa
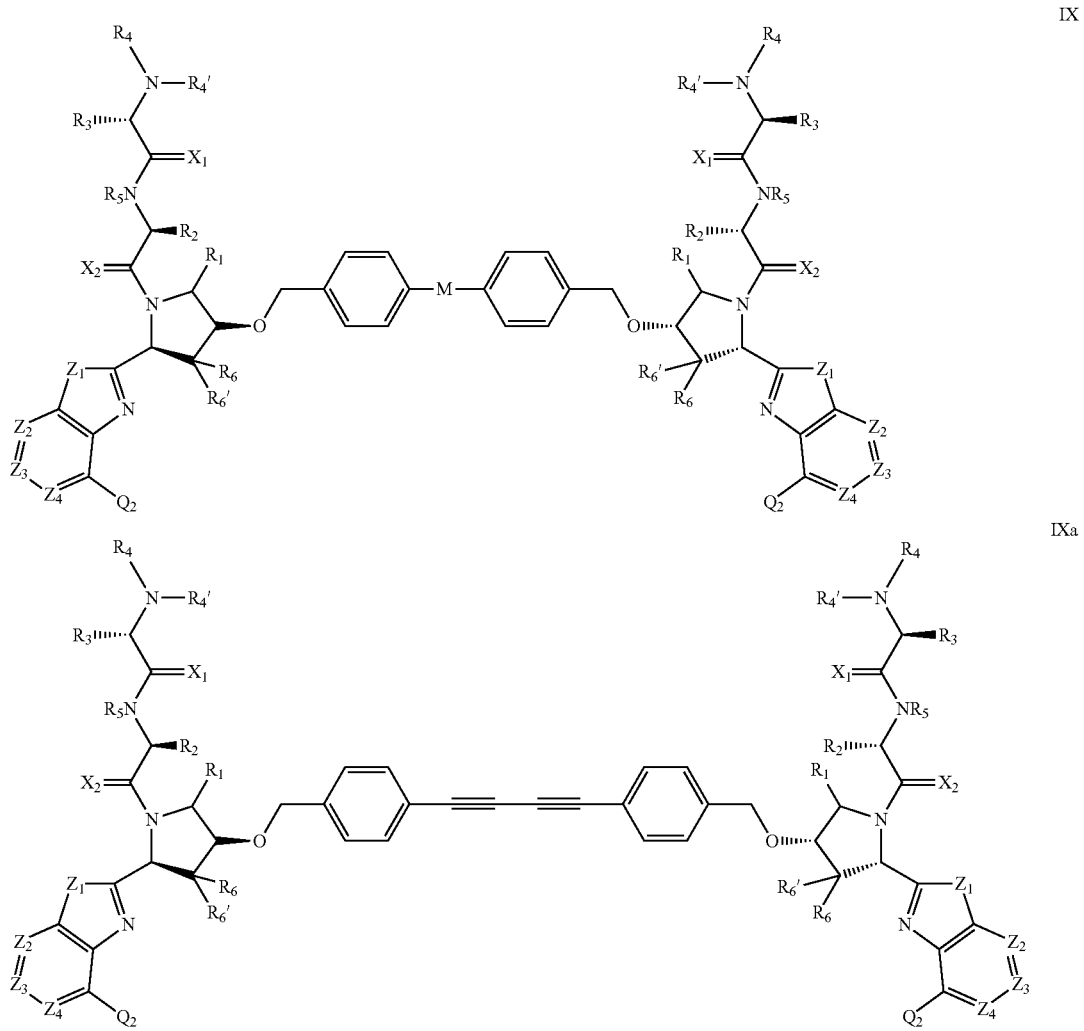
In a particular embodiment compounds of the invention have the formula X, Xa or Xb

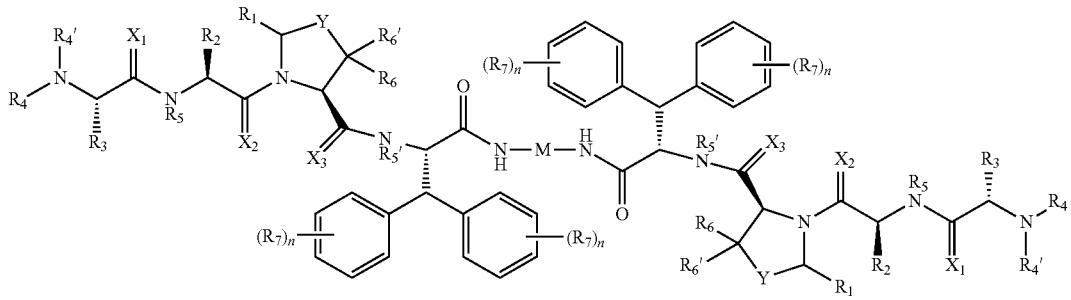

X

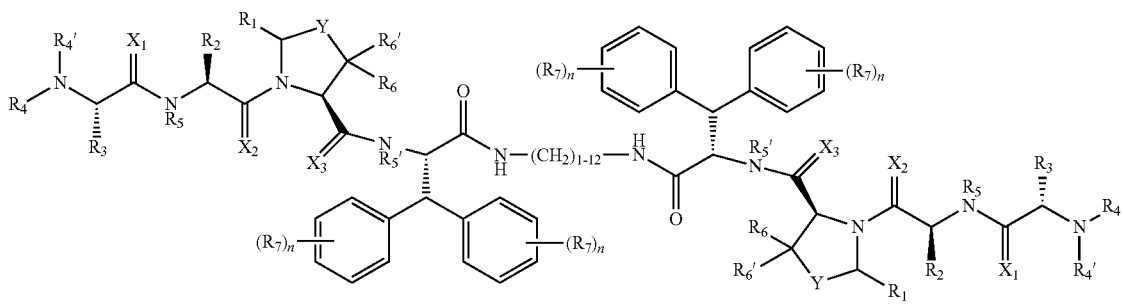

Xa

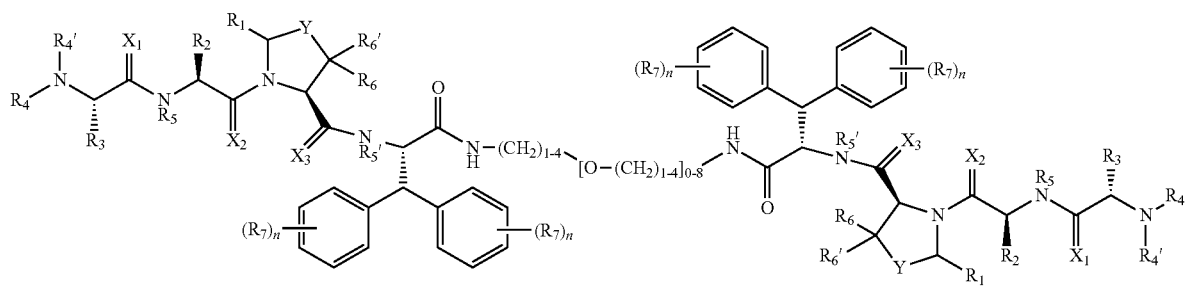

Xb

The invention also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:

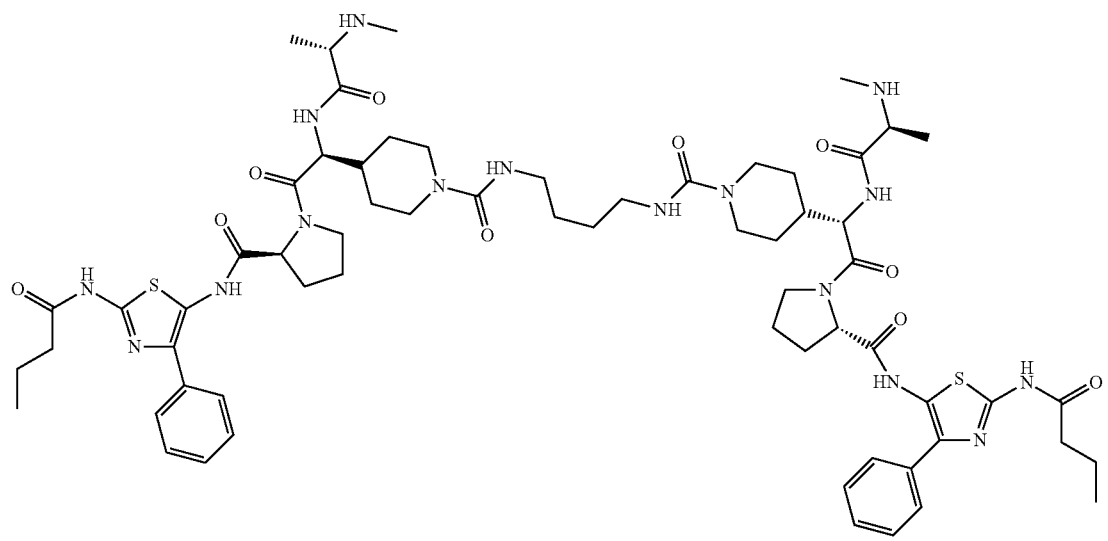
1
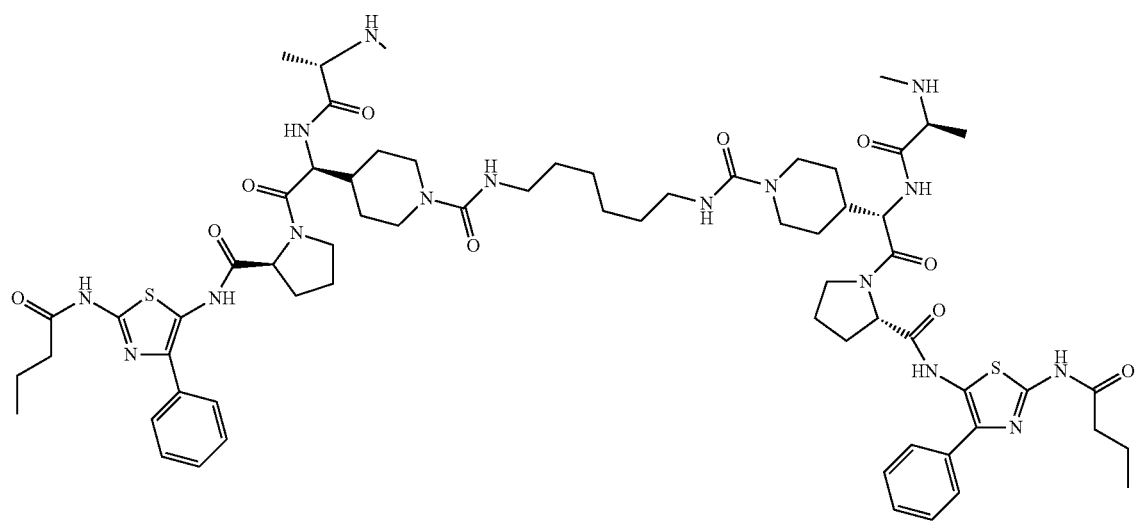
2
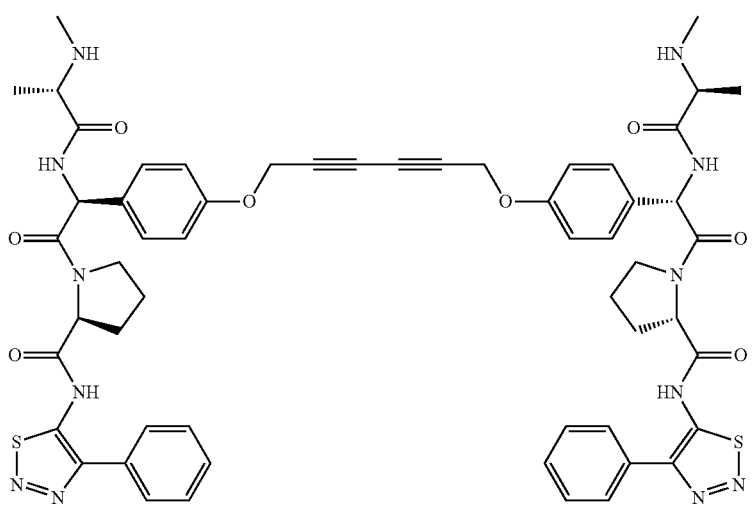
3

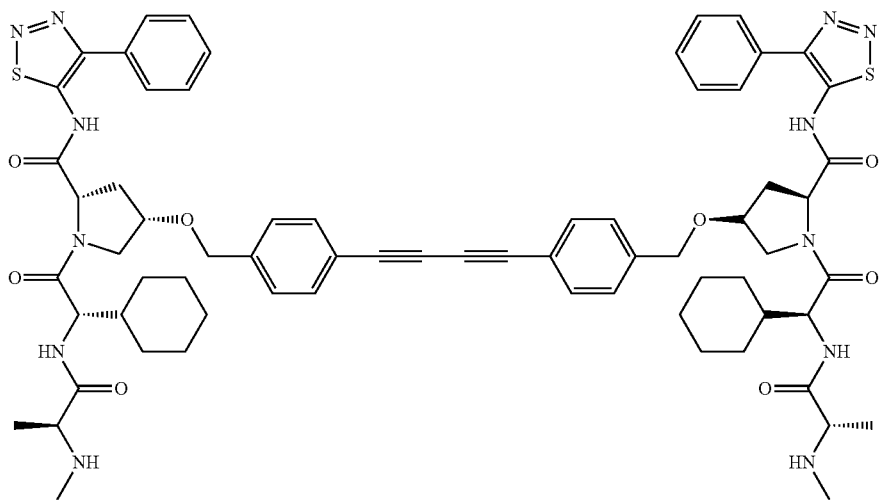
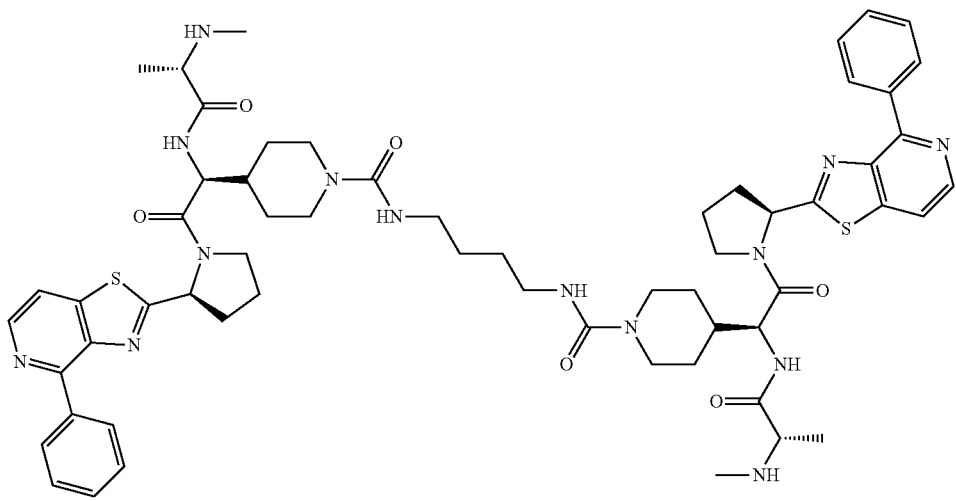
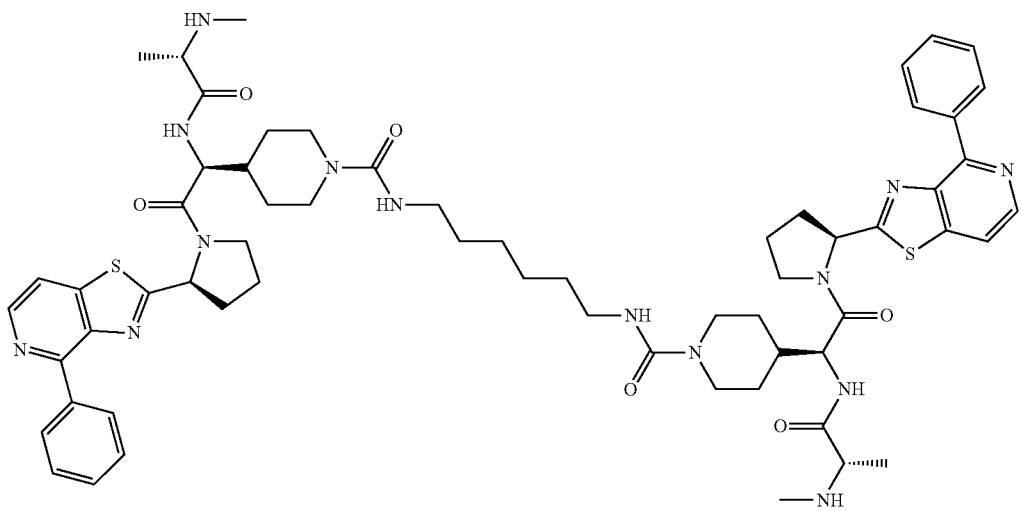

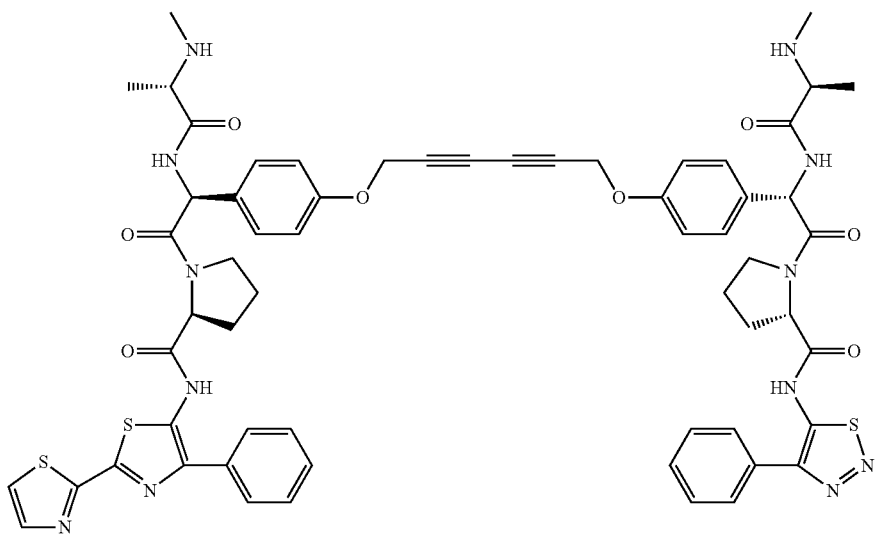
7
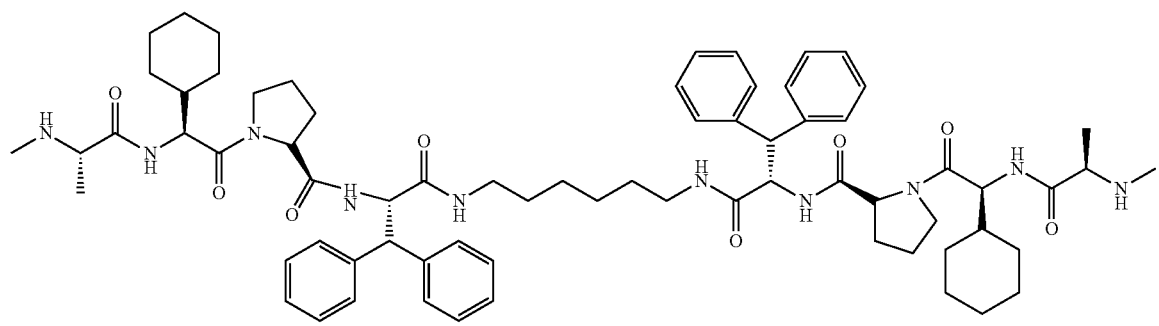
8
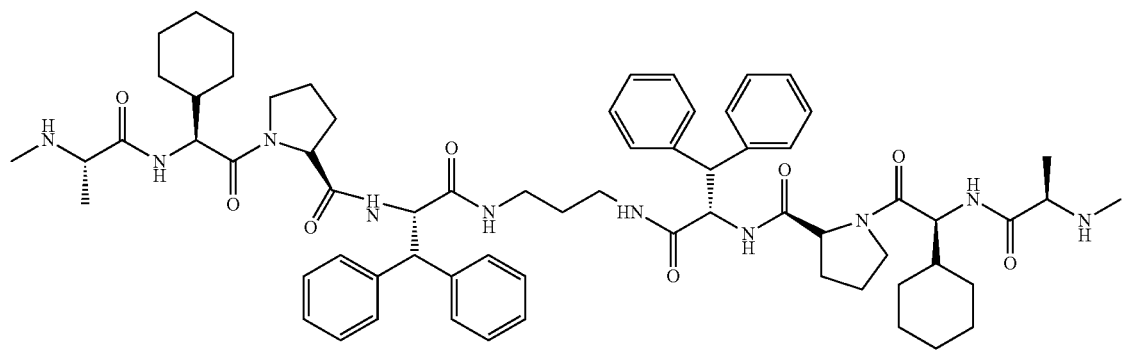
9
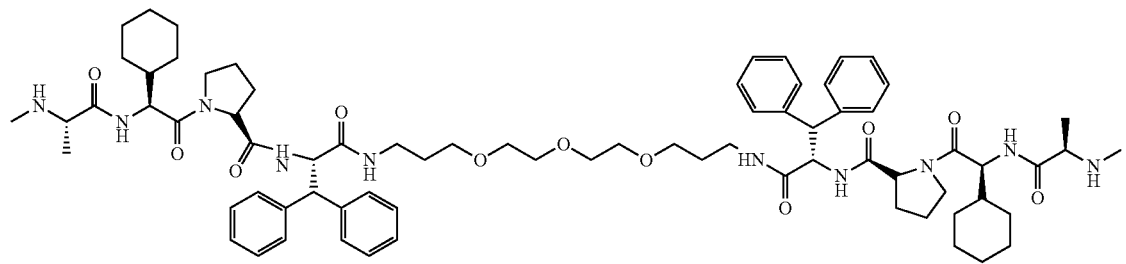
10

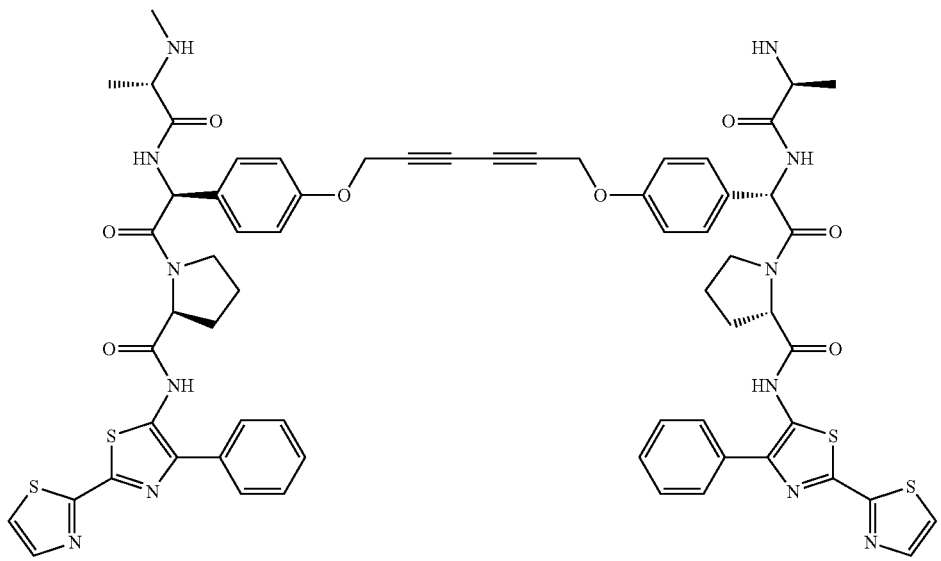
11
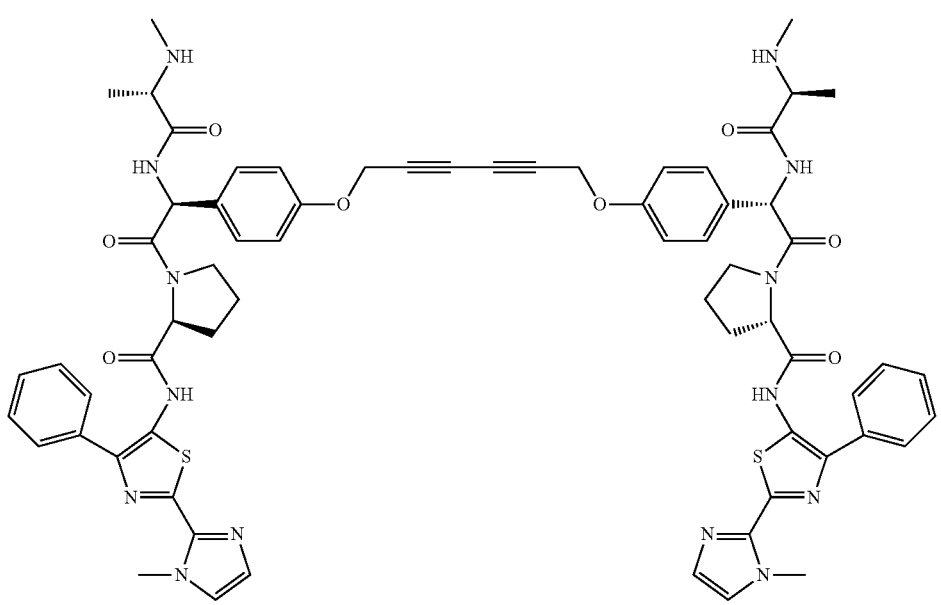
12

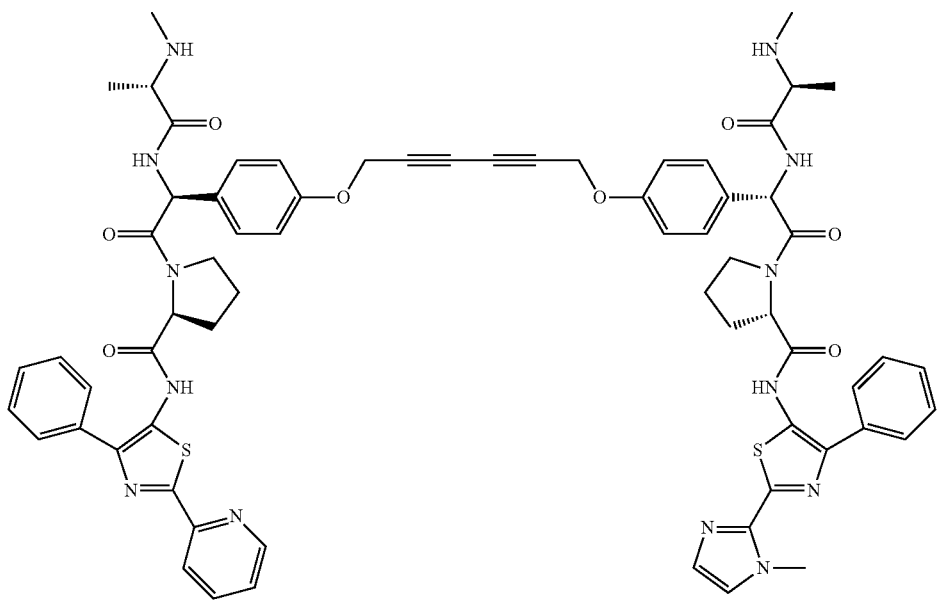
13
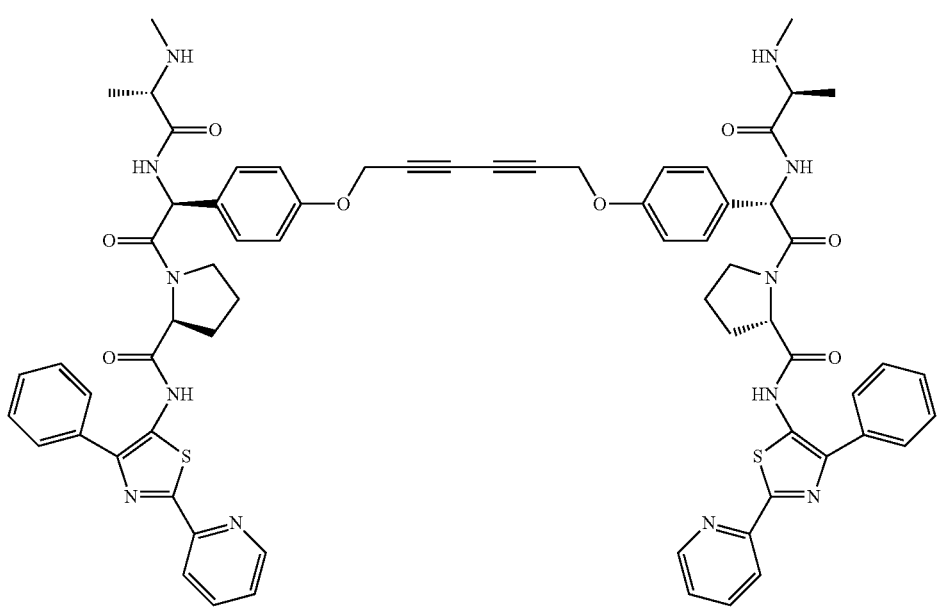
14

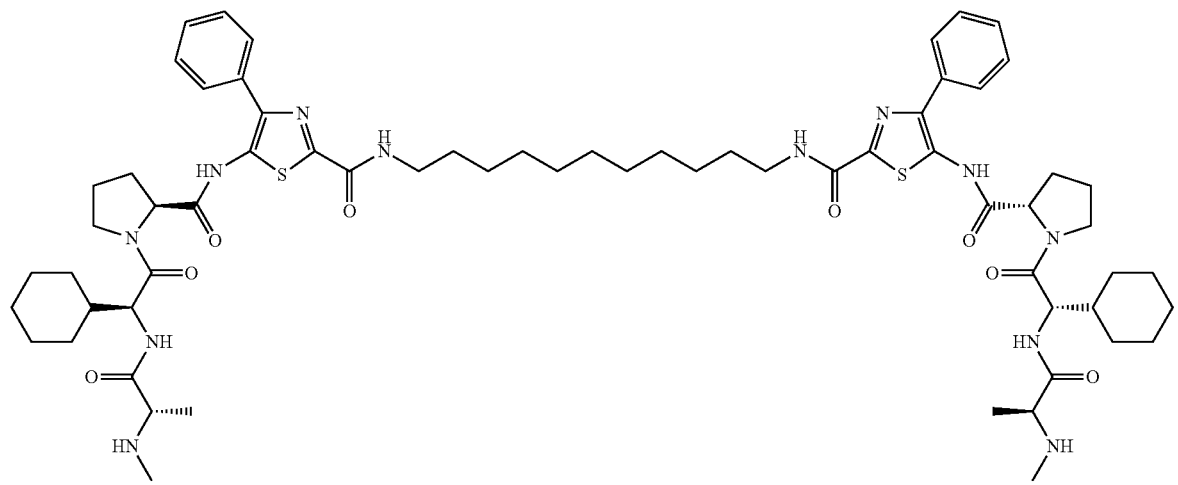
15
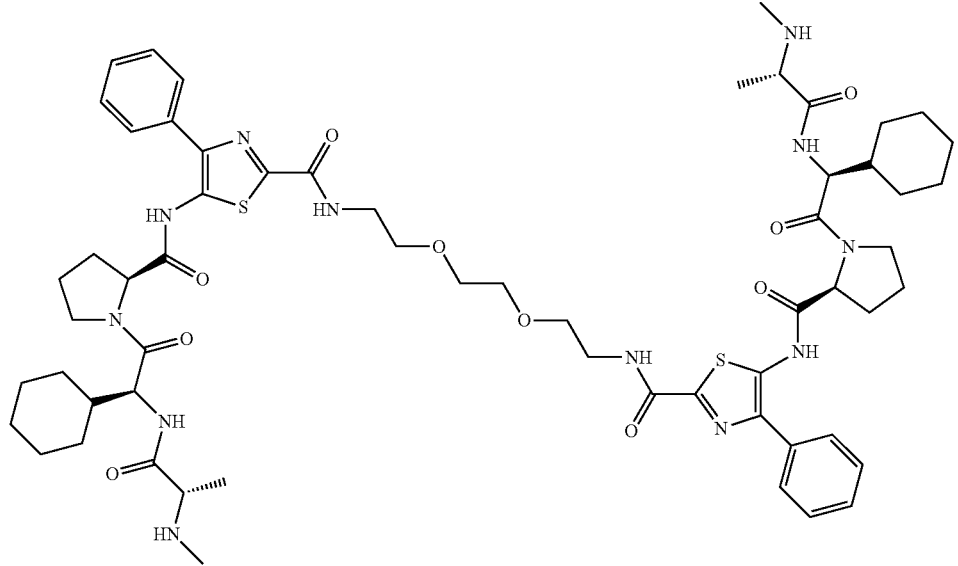
16
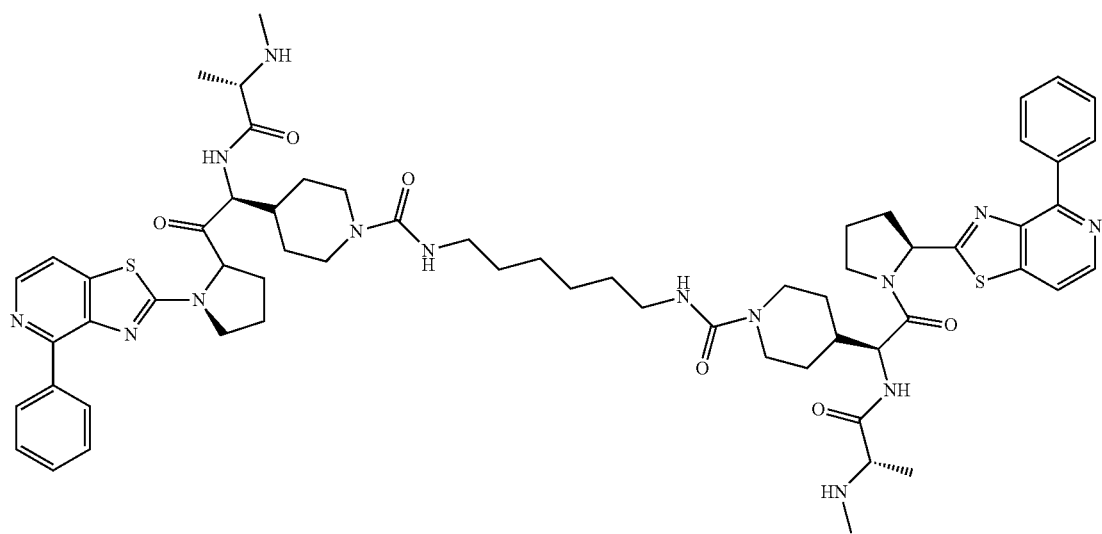
17

-continued
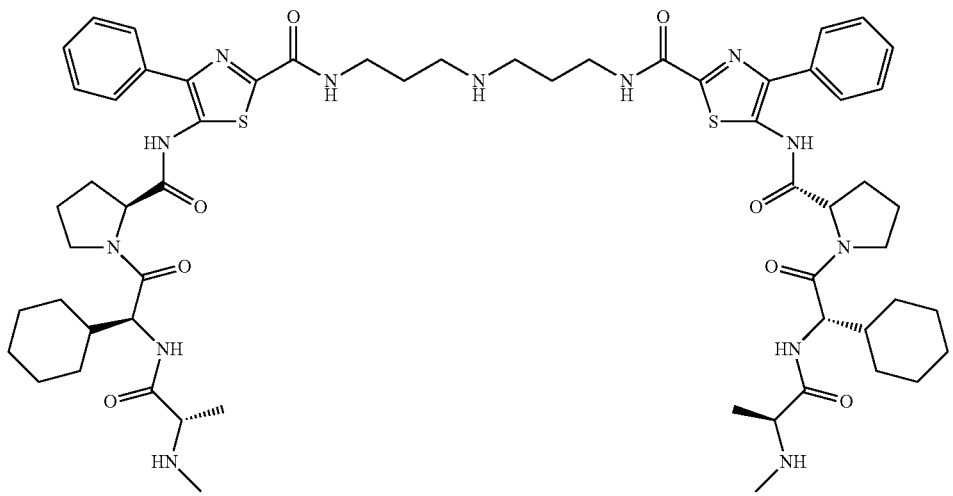
18
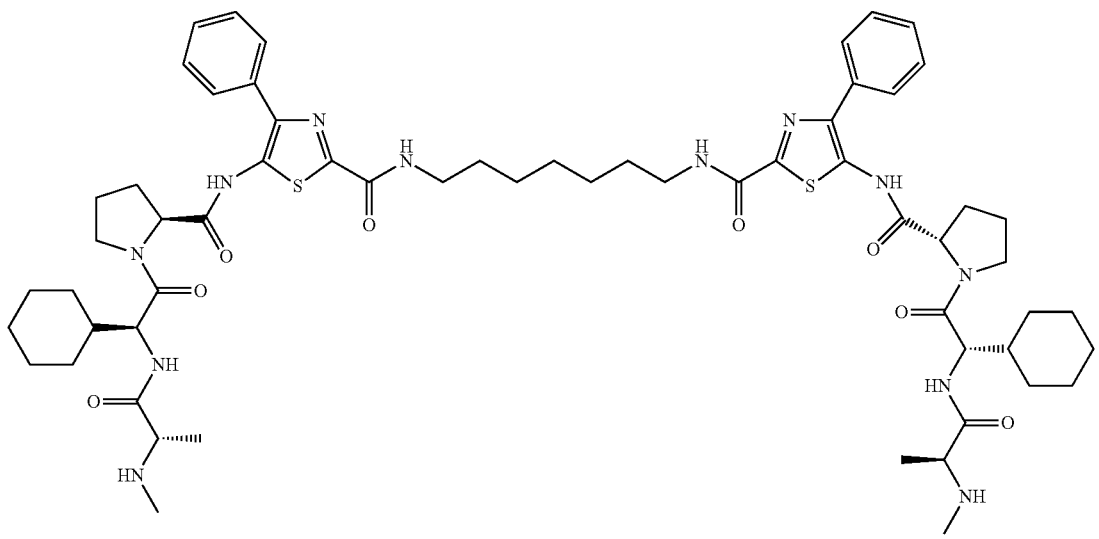
19
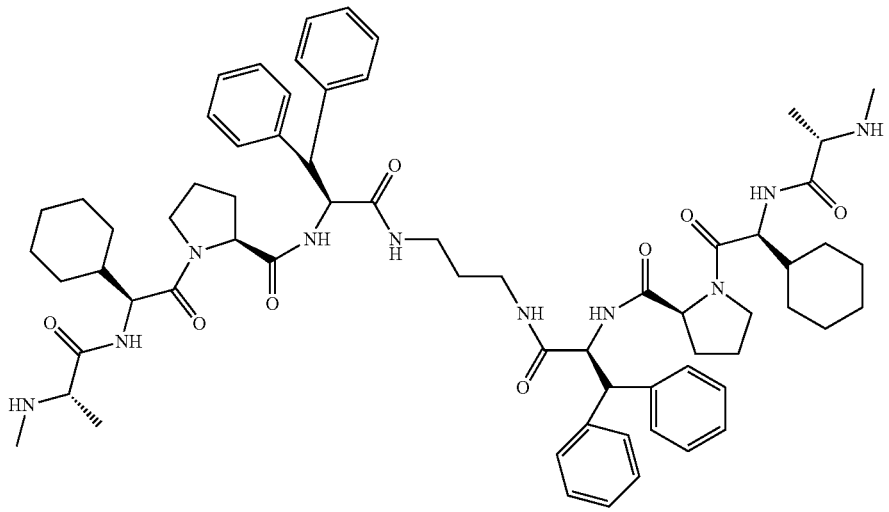
20

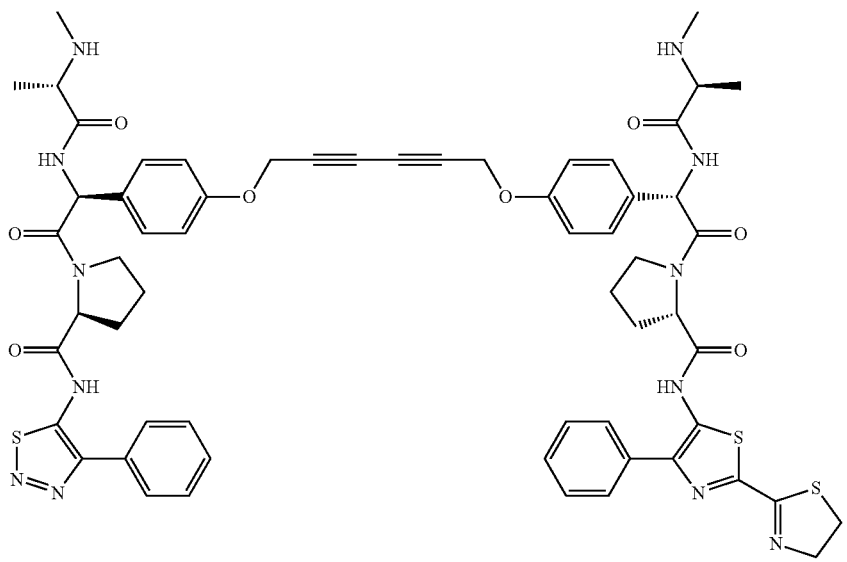
21
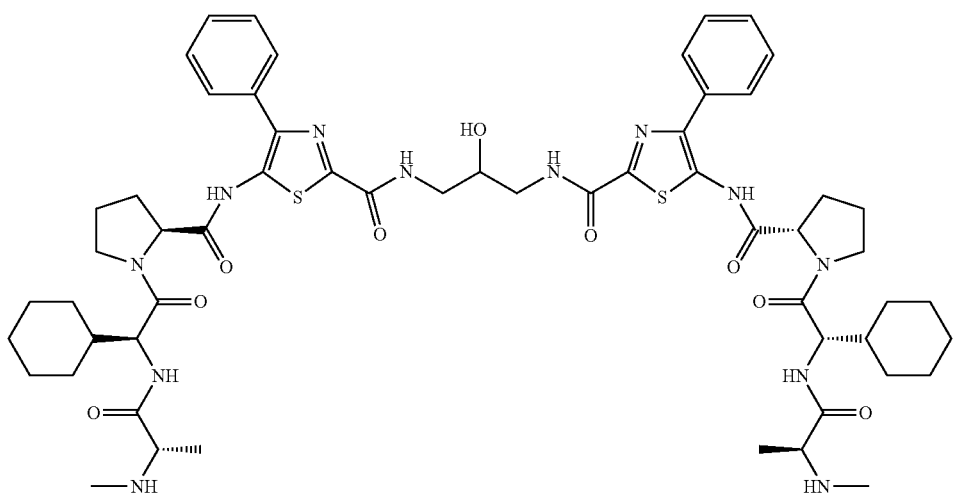
22
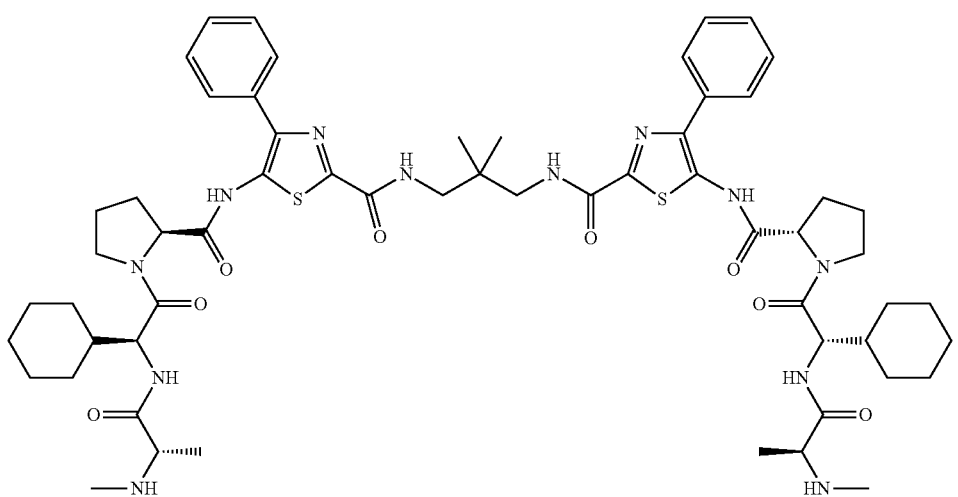
23

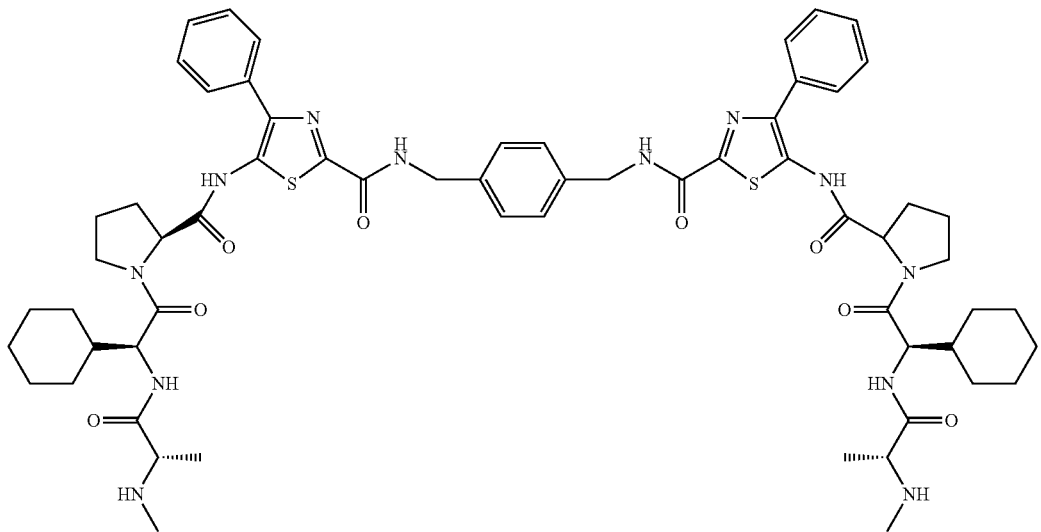
24
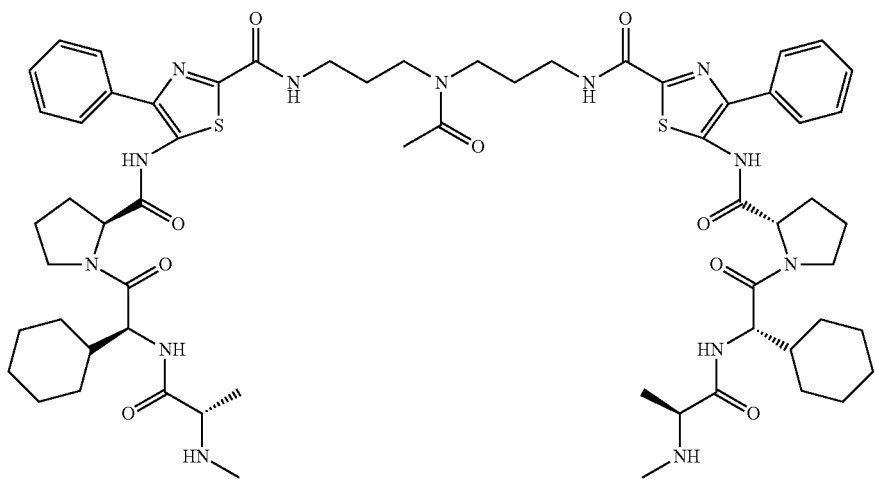
25
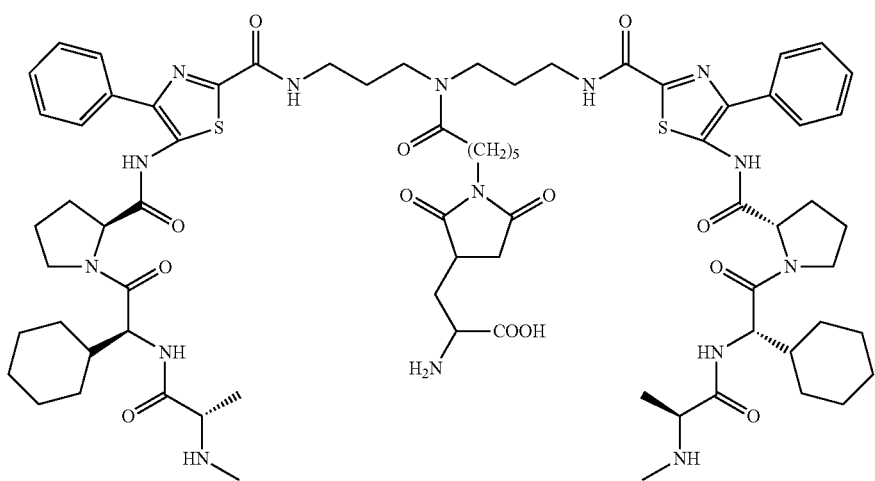
26

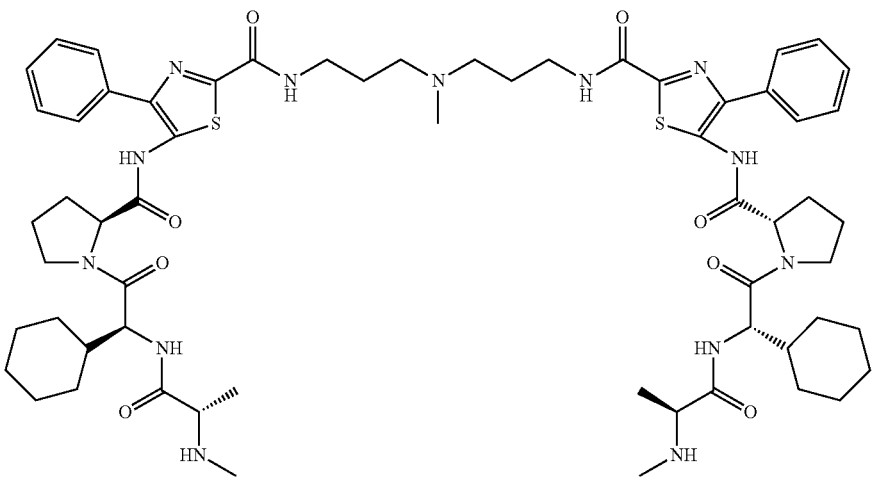

27

SYNTHESIS

Compounds of the invention may exist in different resonance forms and that all such resonance forms are within the scope of the invention herein.

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection steps that are standard in organic synthesis may be required but may not be illustrated in the following schemes. In a general synthetic scheme monomer $U_1$ and $U_2$ are prepared first and then coupled with a linking group M to give compounds of the invention. Monomers may be prepared using typical peptide chemistry techniques by coupling the amino acid residue analogues with typical amide coupling procedures which are described in US2005/0261203, US2006/0014700, US2006/0167066 and PCT/US2006/062335 each of which is incorporated herein by reference.

In scheme 1, amine-protected amino acid residue analogues are coupled and deprotected sequentially to give the final compounds Scheme 1

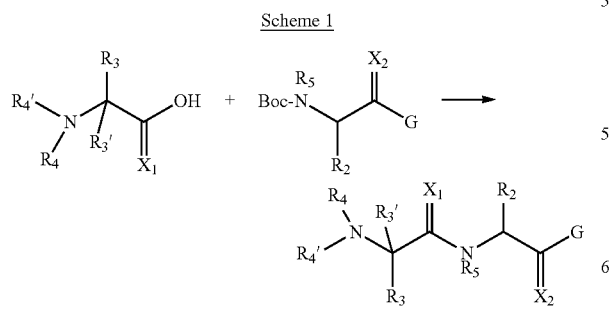

Monomers in which $R_4$ or $R_4'$ are other than H may be prepared according to standard organic chemistry techniques, for example by reductive amination in which a starting amino acid residue analog e.g. $NH_2$—$CH(R_3)$—$C(O)$—$OH$ is reacted with a suitable aldehyde or ketone to give the desired $R_4$ and $R_4'$ substituents as illustrated in the following scheme. The resulting $R_4/R_4'$ substituted amino acid intermediate can then be conjugated to the next amino acid intermediate or the remainder of the compound using standard peptide coupling procedures.

Scheme 2

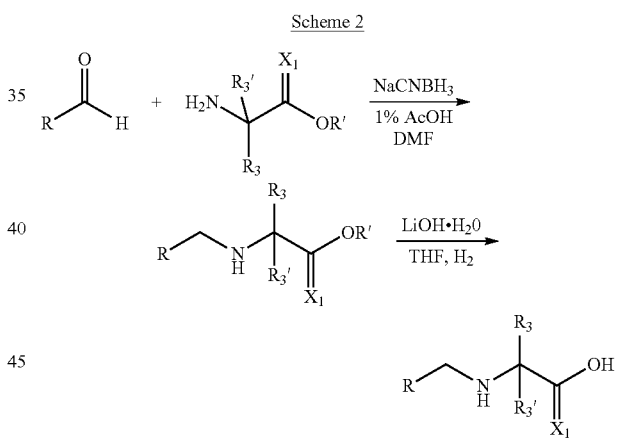

In a particular embodiment, alanine is reacted with 1-methylindole-2-carboxaldehyde and reduced with sodium cyanoborohydride dissolved in 1% HOAc/DMF to give the N-substituted alanine residue which may be used in preparing compounds of the invention as shown in the following scheme.

Scheme 3

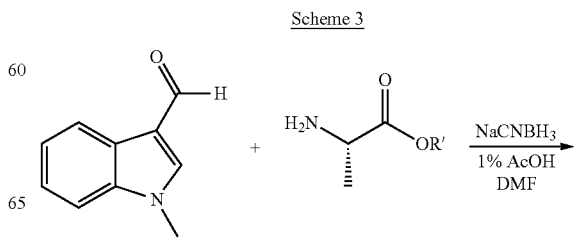

-continued

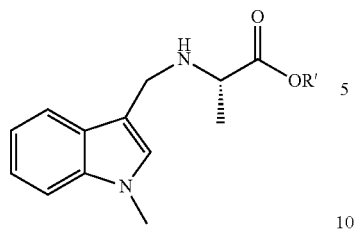

Alternatively, the reductive amination procedure to introduce $R_4/R_4'$ substituents is the final step in the preparation of the compound.

When compounds of the invention incorporate $R_4$ or $R_4'$ substituents other than H, they may also be prepared by substitution of a suitable acid intermediate which incorporates a leaving group with a desired amine. For example Br—CH($R_3$)—C(O)—OH is substituted with an amine $R_4$—$NH_2$ or $R_4$—NH—$R_4'$ according to the following scheme.

Scheme 4

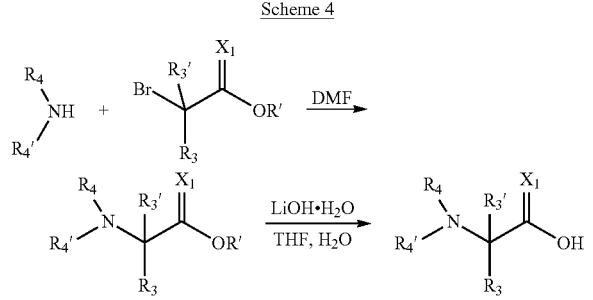

Alternatively, the substitution reaction introducing $R_4$ or $R_4'$ substituents may be performed as a final step in the preparation of the compound as illustrated in the following scheme.

Scheme 5

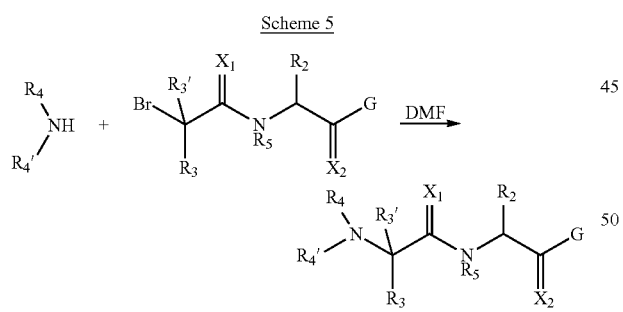

In a particular embodiment, 2-bromopropionic acid is reacted with the following amines dissolved in DMF and bubbled for until substitution is complete to form N-substituted alanine residues:

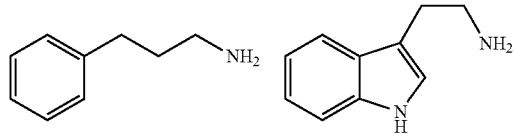

-continued

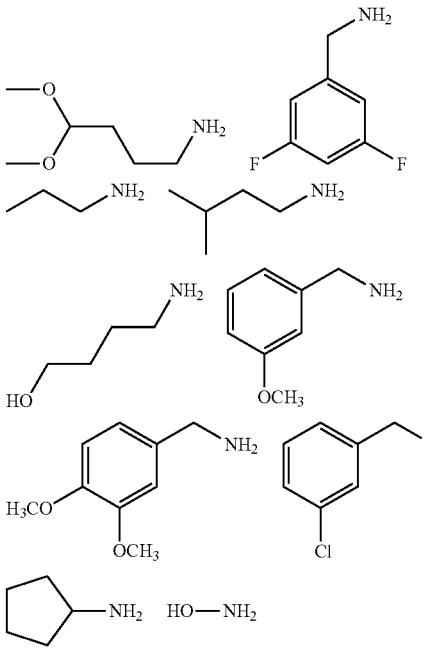

Compounds of the invention in which either $X_1$ or $X_2$ is sulfur, i.e. the compound incorporates a thioamide, may be prepared according to established organic chemistry techniques. For example, compounds in which $X_2$ is sulfur can be prepared starting with an Fmoc protected amino acid residue analog $NH_2$—CH($R_2$)—COOH which is reacted with a thionating reagent such as Lawesson's Reagent or $P_4S_{10}$.

Monomers ($U_1$ or $U_2$) in which G has the formula IVa in which L is —C($X_3$)—, a general synthetic scheme may involve an N-protected 6-amino-azabicyclo-octane group that is coupled to an activated ester of the desired acid (e.g. naphthalene-carboxylic acid) followed by deprotection of the ring amine and subsequent coupling of amino acid residues thereto using typical amide coupling procedures.

Scheme 6

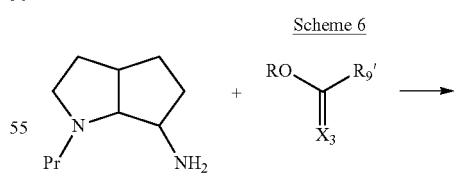

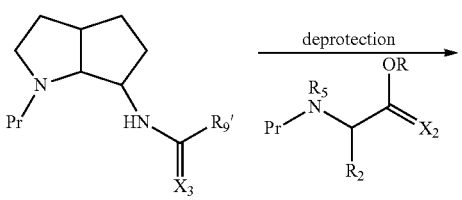

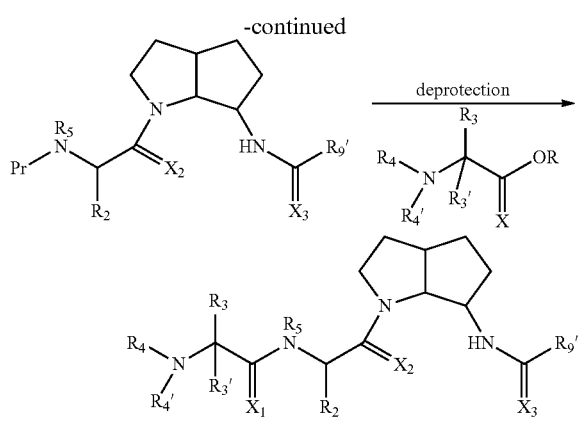

The N-protected 6-amino-azabicyclo-octane intermediate may be prepared according to the procedures described in Cary et al, Tetrahedron Letters, 1989, 30:5547 illustrated in the following scheme. In general, an activated ester of cyclopentene acetic acid is coupled to methylbenzyl amine. The methylbenzyl group serves as an amine protecting for the ring product prior to coupling to amino acid residues. The resulting amide is reduced with lithium aluminum hydride to form a secondary amine which is then reacted with N-bromosuccimide. The resulting N-bromo amine is cyclized with a catalytic amount of cuprous bromide to generated the 6-bromo substituted azabicyclo-octane ring. The ring is then reacted with ammonium hydroxide to convert the 6-bromo group to the corresponding 6-amino ring intermediate which then may used in the synthesis of the compounds of the invention.

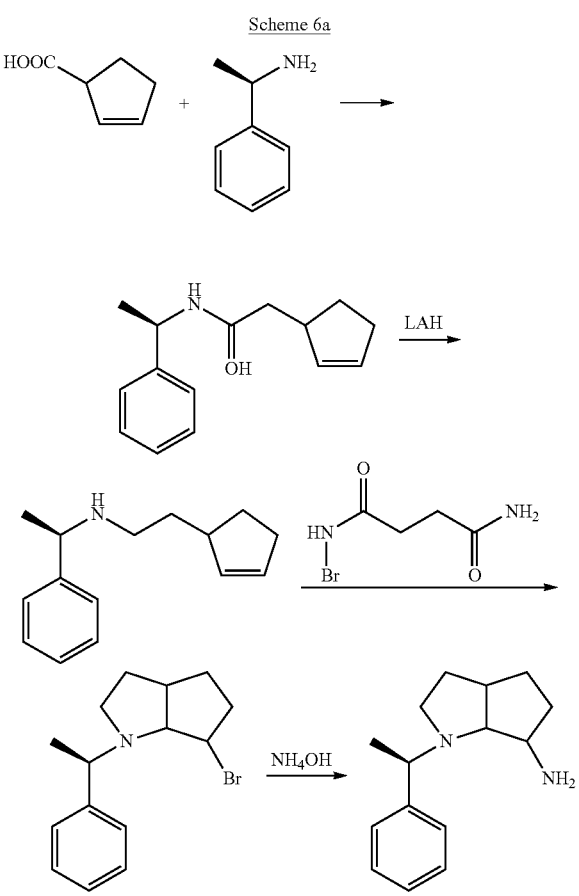

Monomers ($U_1$ or $U_2$) in which G has the formula IVb are prepared by coupling an amine-substituted ring A to a proline analog employing standard amide coupling techniques. The amine-substituted ring A is commercially available or else prepared from standard organic chemistry techniques. For example, 1-aryl-5-aminotetrazoles, such as phenyl-5-aminotetrazole, may be prepared according to the following scheme from commercially available phenyl thiourea by reacting with sodium azide and mercuric chloride.

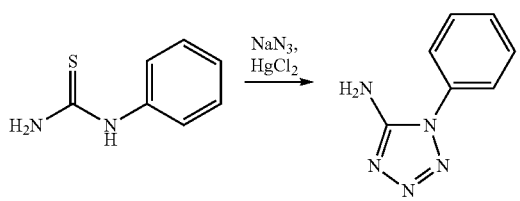

3-Aryl-5-amino-1,2,3-triazoles, such as 3-Phenyl-3H-[1,2,3]triazol-4-ylamine, may be prepared according to the procedures described in J. Org. Chem., 1981, 46:856-9 and illustrated in the following scheme by reacting phenylamine with aminoacetonitrile.

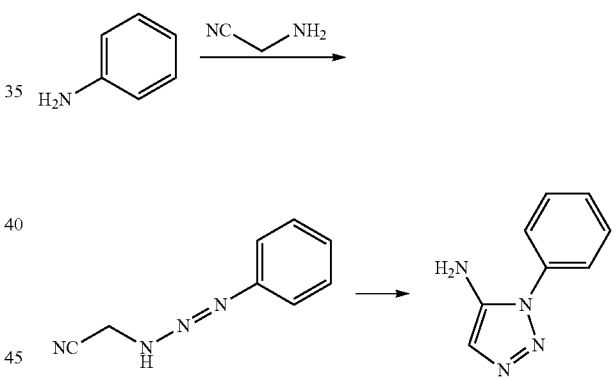

Similarly, 5-Amino-1-phenyl-1H-[1,2,3]triazole-4-carbonitride may be prepared by reacting phenylamine with 2-amino-malononitrile as illustrated in the following scheme.

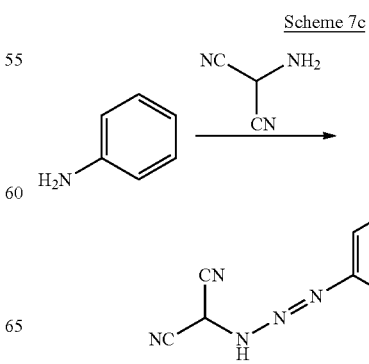

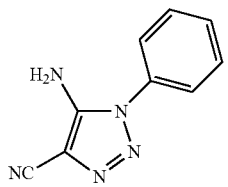

4-Aryl-5-amino-1,2,5-oxadiazoles, such as 4-phenyl-fura-zan-3-ylamine, may be prepared according to the procedures described in Lakhan et al, (Indian Journal of Chemistry, Section B: Organic Chemistry Including Medicinal Chemistry (1987) 26B(7):690-2) and illustrated in the following scheme by reacting benzoyl cyanide with hydroxylamine Scheme 7d

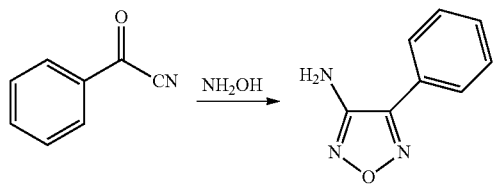

4-Aryl-3-amino-1,2,4-triazoles, such as 4-phenyl-4H-[1,2,4]triazol-3-ylamine, may be prepared by reacting phenyl-isothiocyanate with hydrazinecarboximidamide to give 5-amino-4-phenyl-4H-[1,2,4]triazole-3-thiol in which the thiol group may be removed with Raney nickel catalyst as illustrated in the following scheme.

Scheme 7e

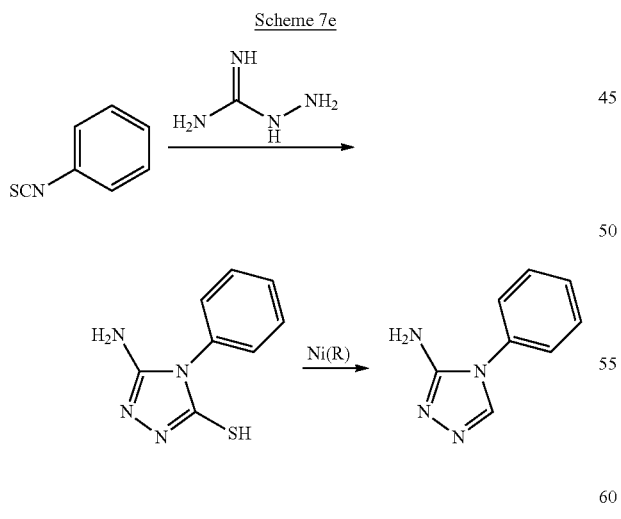

4-Aryl-5-amino-1,2,3-triazoles such as 3,5-diphenyl-3H-[1,2,3]triazol-4-ylamine according to the procedures described in J. Org. Chem., 1990, 55:3351-62 and illustrated in the following scheme, by reacting benzeneacetonitrile with azidobenzene (or alternatively trimethylsilylazide, TMS-N$_3$).

Scheme 7f

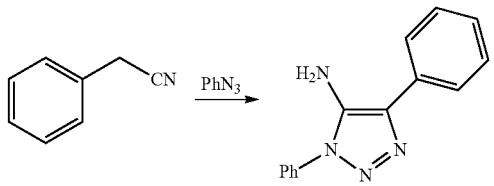

4-Aryl-3-aminopyrazoles such as 4-phenyl-2H-pyrazol-3-ylamine may be prepared according to the procedures described in patent EP269,859 and illustrated in the following scheme, by reacting benzeneacetonitrile with orthoformic acid triethyl ester to give 3-oxo-2-phenyl-propionitrile which is reacted with hydrazine.

Scheme 7g

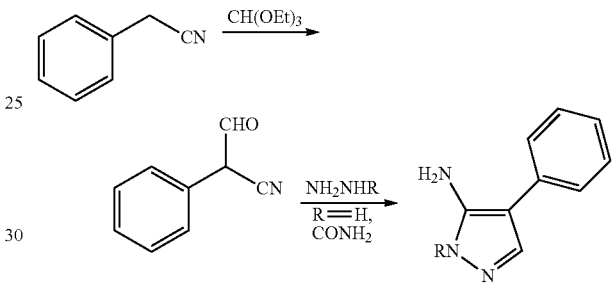

Various hydrazines and derivatives of benzeneacetonitrile can be used to prepare substituted-4-aryl-3-aminopyrazoles as illustrated in the following schemes.

Scheme 7h

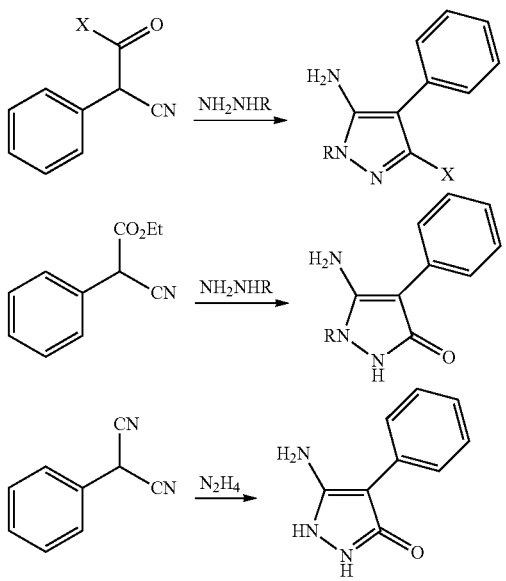

X = H, Me, Et, CO$_2$Et, CF$_3$
R = H, CONH$_2$

1-Aryl-5-aminopyrazoles such as 2-phenyl-2H-pyrazol-3-ylamine may be prepared by reacting phenylhydrazine with 3-oxo-propionitrile. Various nitriles can be used to introduce substitution at the 3-position of the pyrazole ring as illustrated in the following scheme.

Scheme 7i

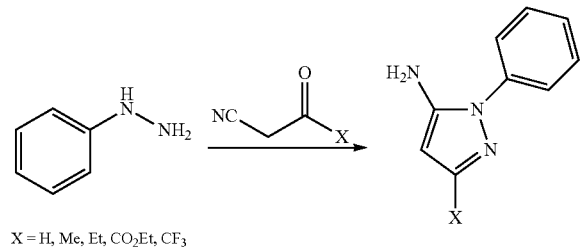

X = H, Me, Et, CO₂Et, CF₃

3-Aryl-4-aminoimidazoles such as 3-phenyl-3H-imidazol-4-ylamine may be prepared by reacting phenylamine with aminoacetonitrile and orthoformic acid triethyl ester as illustrated in the following scheme. Substitution at the 2-position of the imidazole can be introduced using analogs of the orthoformic acid triethylester as follows.

Scheme 7j

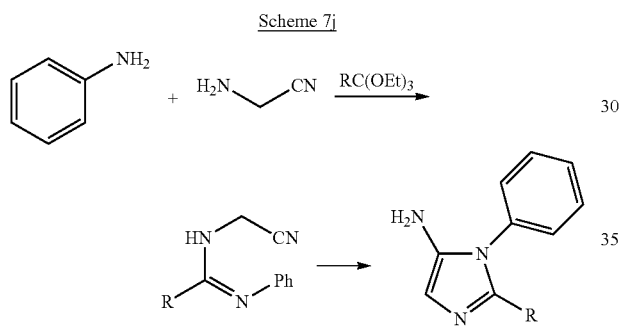

5-Aryl-4-aminoimidazoles such as 5-phenyl-3H-imidazol-4-ylamine may be prepared by reacting formamidine with aminophenylacetonitrile as illustrated in the following scheme. Substitution at the 2-position of the imidazole ring can be introduced using analogs of the formamidine.

Scheme 7k

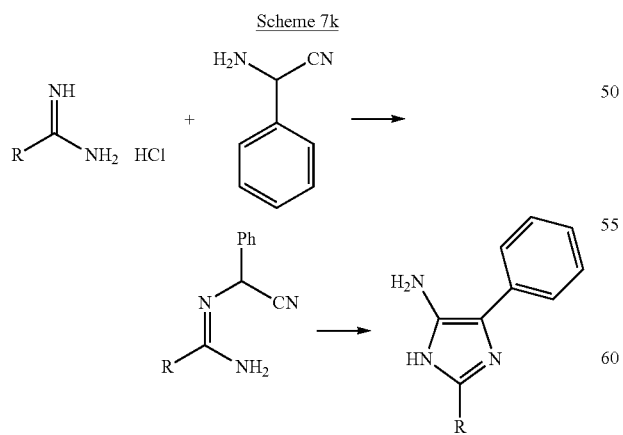

4-Aryl-[1,2,3]thiadiazol-5-ylamines such as 4-phenyl-[1,2,3]thiadiazol-5-ylamine may be prepared according to the following. 2-bromo-1-phenyl-ethanone is reacted with lithium phthalimide and the substitution product is reacted with hydrazinecarboxylate ethyl ester. The resulting hydrazinecarboxylate ethyl ester is cyclized to form a thiadiazole by reacting with thionyl chloride followed by removal of the phthalimide group with hydrazine.

Scheme 7l

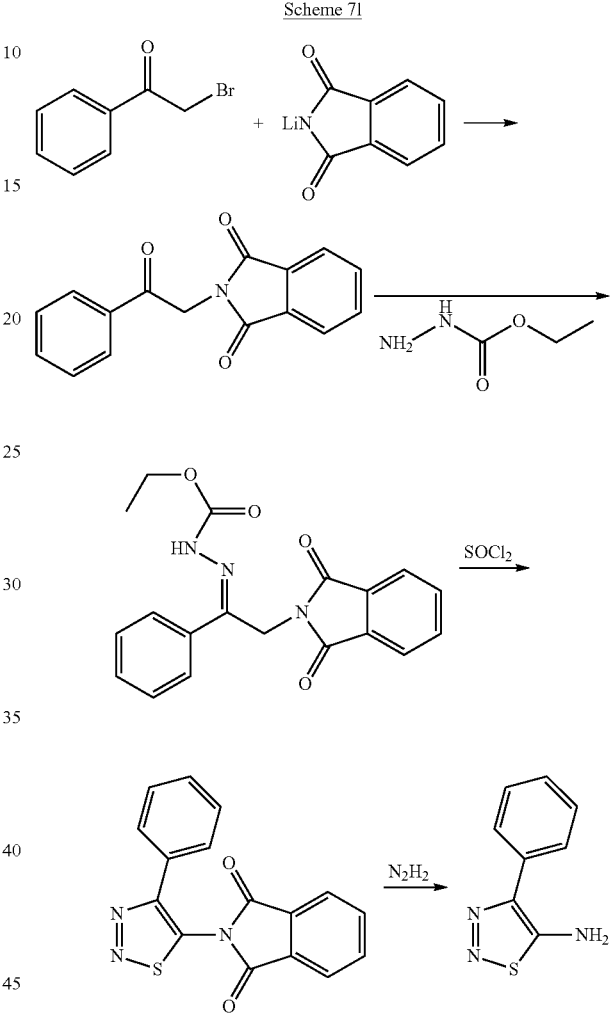

Monomers (U₁ or U₂) in which G has the formula IVc are from commercially available reagents employing standard organic chemistry techniques. For example, when ring A is thiazole, the intermediate may be prepared according to the following scheme:

Scheme 8a

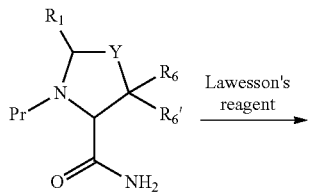

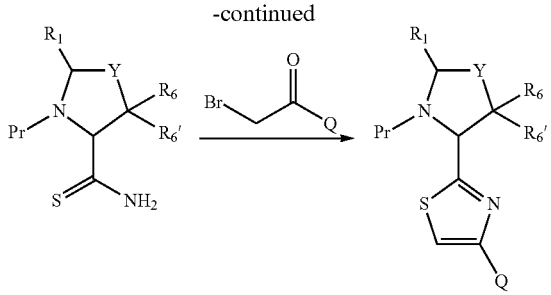

wherein Q, Y, R$_1$, R$_6$, and R$_6$' are as defined herein and Pr is an amine protecting group. A proline analog wherein the alpha nitrogen is protected (Pr), for example with Boc or Cbz, and amidated is converted to the corresponding thioamide, for example using Lawesson's reagent according to the procedures described in Williams et al (J. Org. Chem., 2001, 66:8463). The thiamide is then cyclized with an appropriate bromide to give the desired thiazole substituted with group Q, for example using the procedures described in Ciufolini et al, (J. Org. Chem. 1997, 62: 3804). Alternatively, the bromide in the present scheme may incorporate a functional group which may be used to couple a desired group Q to the thiazole formed from the cyclization step.

For monomers in which G has the formula IVc in which ring A is an oxazole, the intermediate may be prepared according to the following scheme.

Scheme 8b

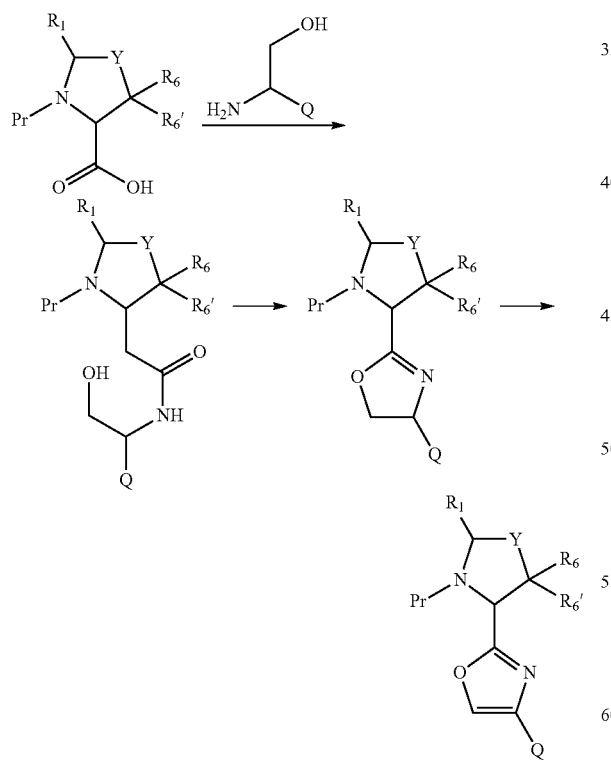

wherein Q, Y, R$_1$, R$_6$, and R$_6$' are as defined herein and Pr is an amine protecting group. The starting proline analog is reacted with an appropriate amine using standard amide forming procedures. The resulting amide is cyclized, for example using Burgess Reagent according to the procedures described in Pihko et al (J. Org. Chem., 1999, 64:652), to give the dihydro-oxazole. The dihydro-oxazole is then reduced to give the desired oxazole substituted with group Q. Alternatively, the amine of the first step in the scheme may incorporate a functional group in place of Q which may be used directly or indirectly to couple a desired group Q to the thiazole formed from the cyclization step.

Monomers (U$_1$ or U$_2$) in which G has the formula IVd may be prepared by coupling amino acid residue analogues employing typical amide coupling procedures. In the following scheme, wherein Q, Y, Z$_1$, Z$_2$, Z$_3$, Z$_4$, R$_1$, R$_6$ and R$_6$' are as defined herein and Pr is a suitable protecting group, amine-protected amino acid residue analogues are coupled and deprotected sequentially to give the final compounds.

Scheme 9

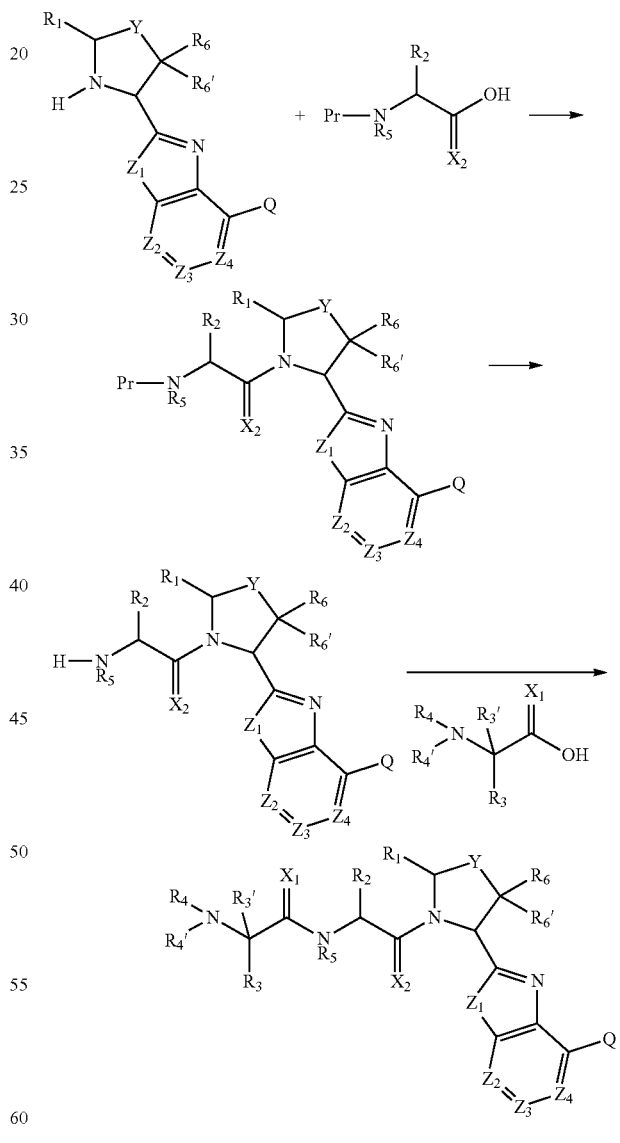

Alternatively monomers in which G has the formula IVd may be prepared by coupling amino acid analogs in any order and may be prepared using solid phase support which is routine in the art. For example, the following scheme illustrates an alternative amino acid residue analogue coupling route.

Scheme 9a

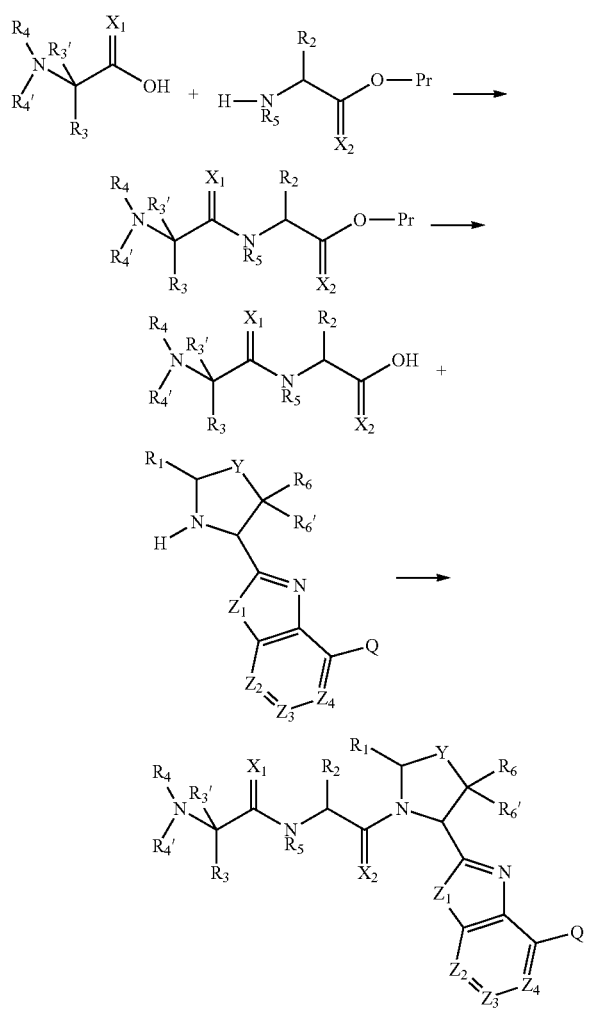

Thiazole amino acid analogs of formula IVd, in which $Z_1$ is S, may be prepared according to scheme 3 wherein Q, Y, Z1, Z2, Z3, Z4, $R_1$, $R_6$ and $R_6'$ are as defined herein and Pr is a suitable protecting group.

Scheme 9b

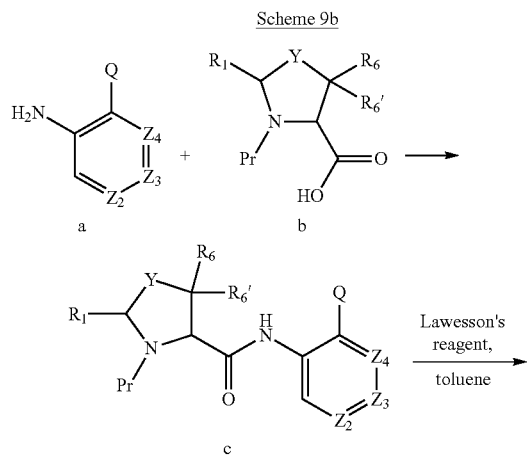

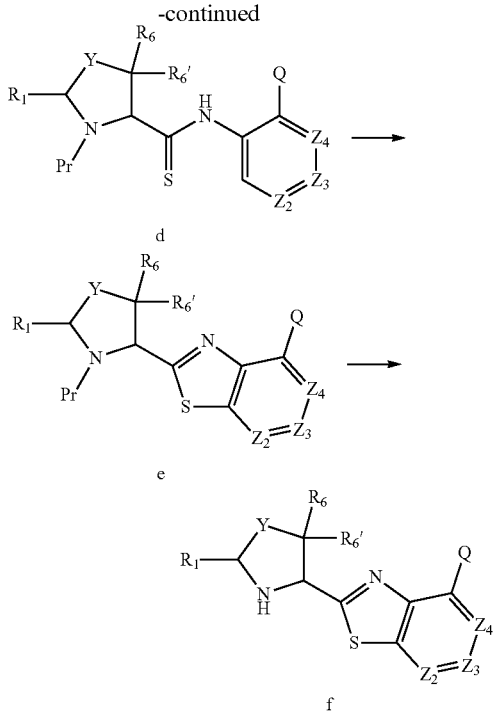

Amine a is coupled with b using standard amide formation procedures, to form amide c which is converted to the corresponding thiamide d by reacting with Lawesson's reagent. Thioamide d is cyclized, for example with $K_3Fe(CN)_6$ in EtOH to form e which is deprotected to give the desired thiazole amino acid analog f.

Alternatively, thiazole amino acid analogs in which $Z_1$ is S may be prepared according to the following scheme.

Scheme 9c

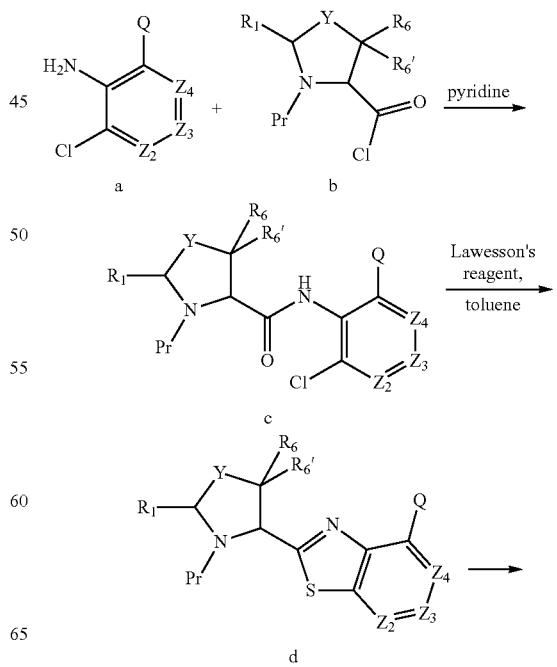

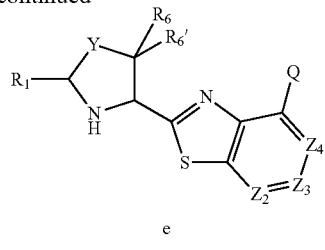

Chloro-substituted amine a is coupled with acid chloride b to give amide c which is reacted with Lawesson's reagent and heated to give cyclized compound d. Compound d is then deprotected to give the desired thiazole intermediate e to be used in preparation of compounds of the invention.

Oxazole amino acid analogs of formula IVd, in which $Z_1$ is O, may be prepared according to the procedures described by Wang et al. (Bioorganic & Medicinal Chemistry (2004), 12(1):17-21) as illustrated in the following scheme.

Scheme 9d

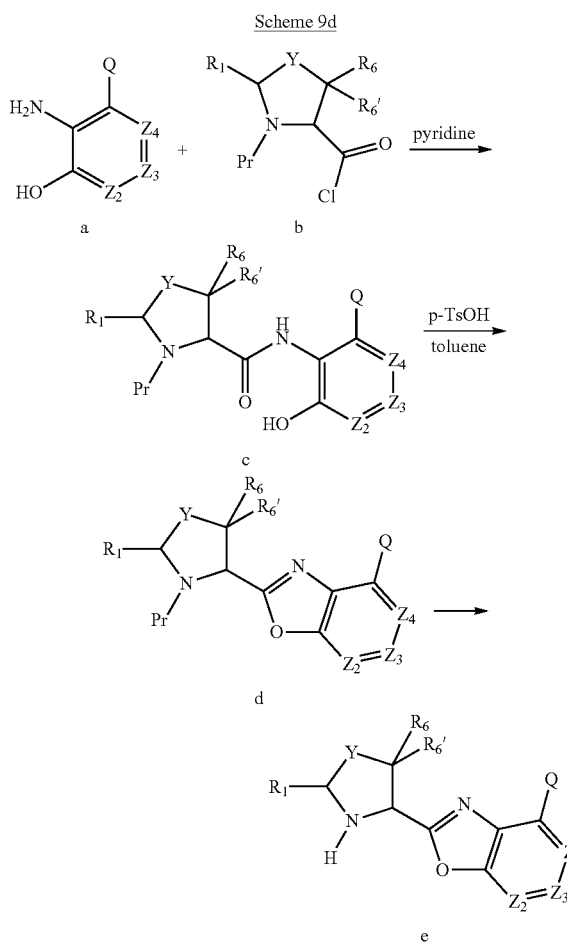

Similar to the previous schemes, an acid chloride b is coupled with amine a to give amide c. However, amide c is refluxed in a solution of p-toluenesulfonic acid in toluene to give d and the protecting group Pr is removed to give the desired oxazole e.

Alternatively, oxazole amino acid analogs of formula IVd may be prepared according to the procedures described by Kauffman et al. (Journal of Heterocyclic Chemistry (2002), 39(5), 981-988) illustrated in the following scheme.

Scheme 9e

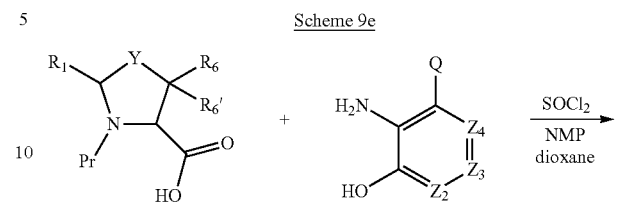

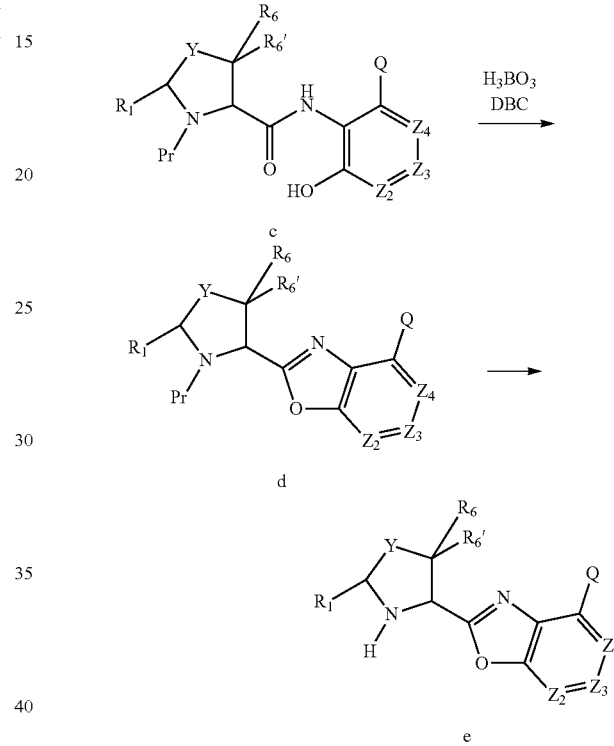

Acid a with dioxane, thionylchloride and N-methylpyrrolidinone are refluxed under inert gas and the resulting acid chloride is coupled with hydroxy/amine b to give amide c. This is then heated with boric acid in dibutylcarbitol to give e and the protecting group Pr is removed to give the desired oxazole intermediate e.

Imidazole amino acid analogs of formula IVd, in which $Z_1$ is NH, may be prepared according to the procedures described by Kumar et al. (Bioorganic & Medicinal Chemistry 2002, 10(12):3997-4004) as illustrated in the following scheme.

Scheme 9f

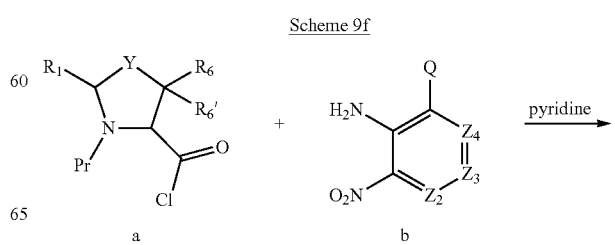

-continued

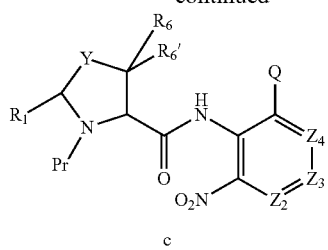

c

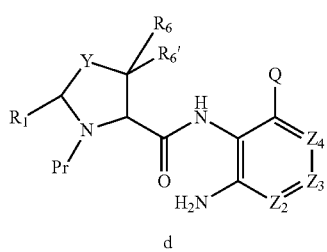

d

AcOH →

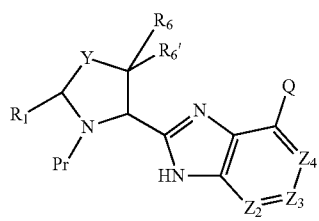

e

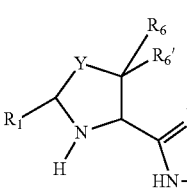

f

Scheme 10

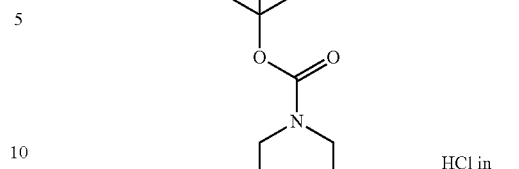

a

HCl in dioxane →

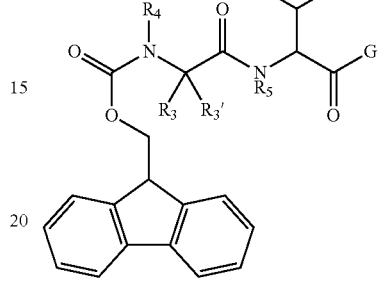

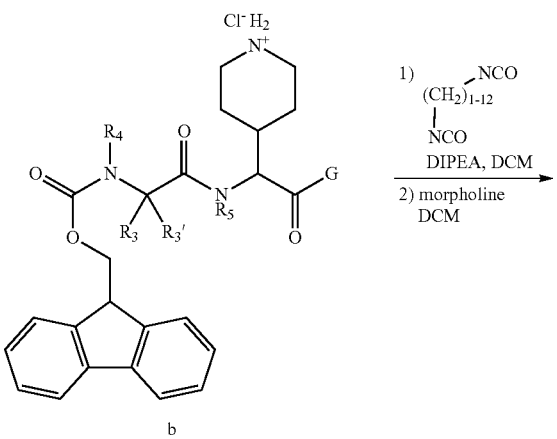

b

1) NCO–(CH$_2$)$_{1-12}$–NCO
DIPEA, DCM
2) morpholine DCM

Acid chloride a is coupled with nitro/amine b to give amide c. The nitro group of amide c is reduced to the corresponding amine d, for example with iron, and is then cyclized by heating with acetic acid to give e. The protecting group Pr of e is removed to give the desired imidazole amino acid analog f.

Dimer compounds of the invention are prepared using standard organic chemistry techniques. They can be conveniently prepared starting with a monomer U$_1$ and coupling to a second monomer U$_2$. Dimer compounds of the invention having the general formula Va in which R$_2$ is a t-butyl protected piperidine may be prepared by dissolving an Fmoc protected monomer a in HCl in dioxane followed by reaction with a diisocyanate linker.

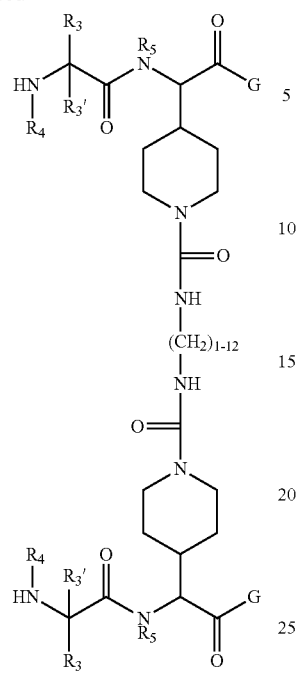

Va

Dimer compounds of the invention having the general formula VIa in which $R_2$ is a hydroxylphenyl may be prepared by reacting a Boc-protected monomer a with propargyl bromide to give propynyloxy monomer b which is dimerized by combining with $Pd(OAc)_2$, CuI and DABCO in acetonitrile followed by Boc removal with HCl in dioxane.

Scheme 11

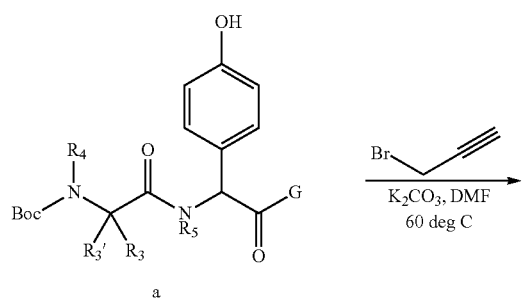

VIa

Dimer compounds of the invention having the general formula VIIa which are linked via proline residues may be prepared by reacting a hydroxy proline residue c with 4-ethynylbenzylbromide b prepared from the corresponding alcohol a. The resulting ethynylbenzyloxy proline d is dimerized by combining with $Pd(OAc)_2$, DABCO and CuI in acetonitrile followed by Boc deprotection with HCl in dioxane.

Scheme 12

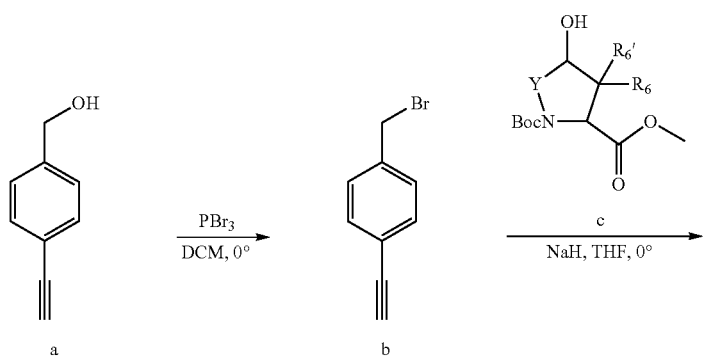

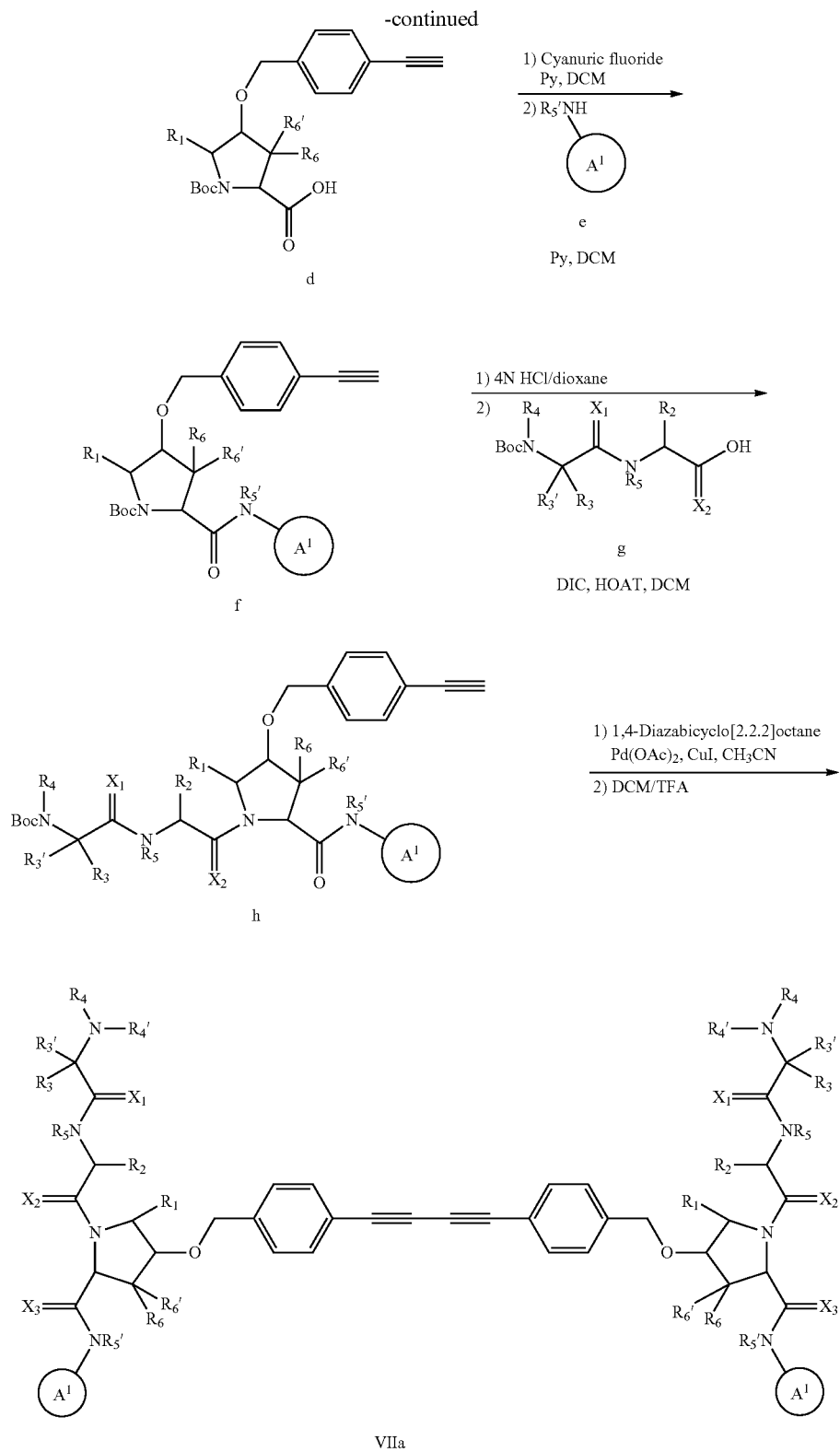
Dimer compounds of the invention having the general formula Xa may be prepared by reacting an Fmoc-protected carboxylic acid monomer a with the appropriate diamine using HATU and DIPEA in DMF followed by Fmoc deprotection with 4-aminomethylpiperidine.

Scheme 13

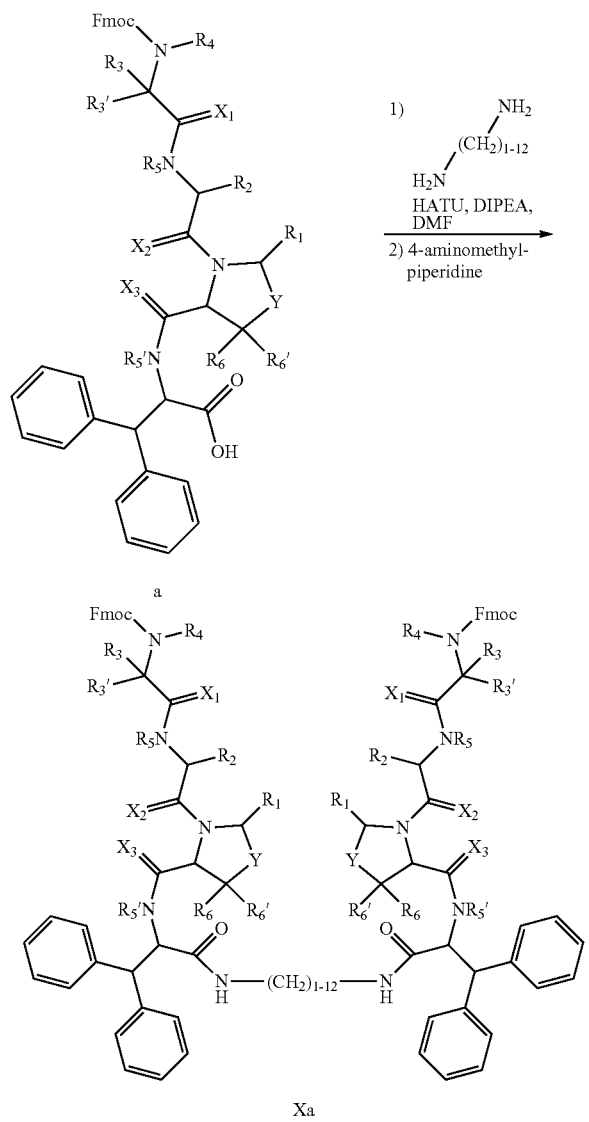

INDICATIONS

The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins. Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present invention are coadministered with a cytostatic compound selected from the group consisting of cisplatin, doxorubicin, taxol, taxotere and mitomycin C. In a particular embodiment, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β1), TRAIL (Apo2L, DR4 ligand), CD95 (Fas, APO-1) ligand, TRAMP (DR3, Apo-3) ligand, DR6 ligand as well as fragments and derivatives of any of said ligands. In an embodiment, the death receptor ligand is TNF-α. In a particular embodiment, the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2

(DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but may range anywhere from about 3 to about 8. Formulation in an acetate buffer at pH 5 is a suitable embodiment. In an embodiment, the inhibitory compound for use herein is sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is may be below the amount that is toxic to normal cells, or the mammal as a whole.

Generally, the initial pharmaceutically effective amount of the compound of the invention administered parenterally per dose will be in the range of about 0.01-100 mg/kg, for example about 0.1 to 20 mg/kg of patient body weight per day, with the typical initial range of compound used being 0.3 to 15 mg/kg/day. Oral unit dosage forms, such as tablets and capsules, may contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants.

EXAMPLES

The invention will be more fully understood by reference to the following examples. They should not, however, be construed as limiting the scope of the invention. Reagents and solvents were obtained from commercial sources and used as received.

Abbreviations used herein are as follows:
AcOH: acetic acid;
ACN: acetonitrile;
Chg: cyclohexylglycine;
DCM: dichloromethane
DIPEA: diisopropylethylamine;
DMAP: 4-dimethylaminopyridine;
DME: 1,2-dimethoxyethane;
DMF: dimethylformamide;
DMSO: dimethylsulfoxide
EDC: 1-ethyl-3-(3-dimethylaminopropyl)carbodiimide;
EEDQ: 2-ethoxy-1-ethoxycarbonyl-1,2-dihydroquinoline;

EtOAc: ethylacetate
EtOH: ethanol;
LCMS: liquid chromatography mass spectrometry;
HATU: O-(7-Azobenzotriazol-1-yl)-1,1,3,3-tetramethyluronium hexafluorophosphate;
HOBt: N-Hydroxybenzotriazole
HBTU: 2-(1H-Benzotriazol-1-yl)-1,1,3,3-Tetramethyluronium Hexafluorophosphate;
HPLC: high performance liquid chromatography;
MeOH: methanol;
NBS: N-bromosuccinamide;
TASF: tris(dimethylamino)sulfonium difluorotrimethylsilicate;
TEA: triethylamine;
TFA: trifluoroacetic acid;
THF: tetrahydrofuran;

Example 1

2-[tert-Butoxycarbonyl-(1H-pyrrol-2-ylmethyl)-amino]-propionic acid

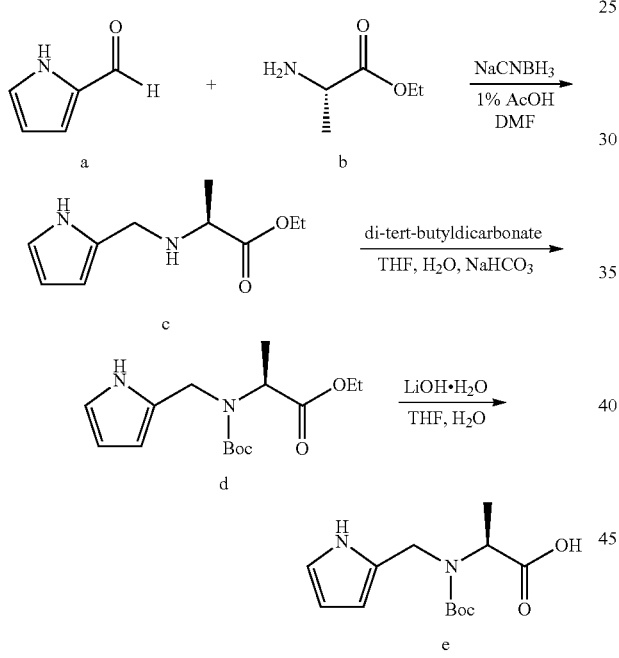

Alanine ethyl ester b (5 g, 32.5 mmol), pyrrole-2-carboxaldehyde a (3.1 g, 32.5 mmol), sodium cyanoborohydride (2.04 g, 32.5 mmol) and AcOH (1%) were mixed in DMF and stirred overnight. The reaction was quenched with $H_2O$, and DMF was evaporated. The mixture was diluted with EtOAc, washed by 0.1N NaOH, dried and concentrated to yield product c 2.5 g. The resulting ester c (2.5 g, 12.8 mmol), di-tert-butyldicarbonate (3.06 g, 14 mmol) were mixed in THF, $H_2O$ with $NaHCO_3$ and stirred overnight. THF was evaporated, and the mixture was diluted with EtOAc, washed by 1N NaOH, sat. $NH_4Cl$ and brine. After dried, the mixture was concentrated to yield the Boc-protected ester d 3.3 g. The Boc-protected ester d (1.67 g, 5.6 mol), lithium hydroxide mono hydrate (284 mg, 6.77 mmol) were mixed in THF and $H_2O$ at 0° C. THF was vacuumed off, and the solution was acidified by dilute $H_2SO_4$, extracted by EtOAc twice. Organic layers were combined, dried and evaporated giving product 2-[tert-butoxycarbonyl-(1H-pyrrol-2-ylmethyl)-amino]-propionic acid e.

Example 2

Tetrahydropyranylglycine

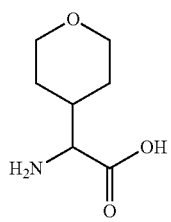

Tetrahydropyranylglycine was purchased from NovaBiochem, or synthesized according to the literature: Ghosh, A. K.; Thompson, W. J.; holloway, M. K.; McKee, S. P.; Duong, T. T.; Lee, H. Y.; Munson, P. M.; Smith, A. M.; Wai, J. M; Darke, P. L.; Zugay, J. A.; Emini, E. A.; Schleife, W. A.; Huff, J. R.; Anderson, P. S. *J. Med. Chem.*, 1993, 36, 2300-2310.

Example 3

Piperidinylglycine

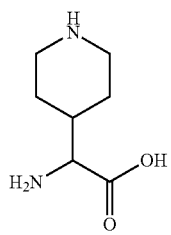

Piperidinylglycine was synthesized according to the procedures described by Shieh et al. (*Tetrahedron: Asymmetry*, 2001, 12, 2421-2425.

Example 4

4,4-difluorocyclohexylglycine

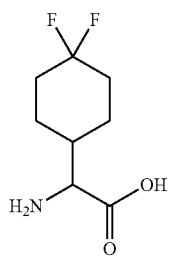

4,4-difluorocyclohexylglycine was made according to the procedures described in patent application US 20030216325.

Example 5

Boc (S)-2-amino-2-(4-hydroxycyclohexyl)acetic acid

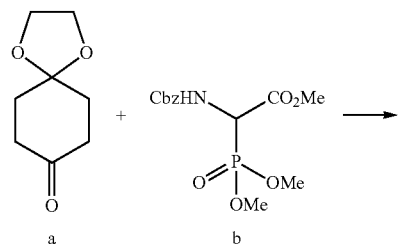

Following the procedure described by Sheih et al. (*Tetrahedron: Asymmetry*, 2001, 12, 2421-2425), a solution of ketone a (8.4 g) and EtOAc (30 mL) was added to a solution of N-Cbz-phosphonoglycine methyl ester b, TMG (4.5 mL) and EtOAc (30 mL). The solution was maintained at rt for 48 h, then washed with 1N HCl (3×50 mL), brine (1×50 mL) dried (Na$_2$SO$_4$), filtered, and concentrated. The residue was adsorbed onto Celite, and purified by chromatography, then further purified by re-crystallization from EtOAc/hexanes to afford 5.2 g of product c.

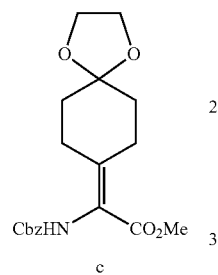

Following the procedure described by Sheih, (*Tetrahedron: Asymmetry*, 2001, 12, 2421-2425), a solution of eneamide c (5.0 g), (S,S)-Me-BPE-Rh(I) (1.5 g, Strem Chemicals, Newburyport, Mass.), and MeOH (100 mL) was shaken vigorously under 70 psi of H$_2$ for 48 h. The solvent was removed under reduced pressure. The residue was taken up in EtOAc, and filtered through SiO$_2$ with more EtOAc. The solvent was removed under reduced pressure to afford 4.0 g of product d as a colorless solid.

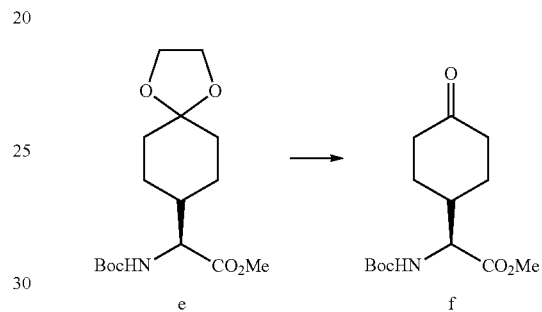

A mixture of Cbz-carbamate d, (4.0 g) Boc$_2$O, (2.9 g), 20% Pd(OH)$_2$.C (1.0 g) and MeOH (30 mL) was maintained under an atmosphere of H$_2$ for 6 h. The mixture was filtered through Celite with MeOH. The solvent was removed under reduced pressure to afford 4.5 g of residue e, which was taken on directly.

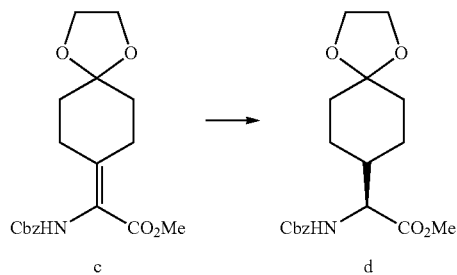 [SMILES: COC(=O)C(NC(=O)OCc1ccccc1)=C1CCC2(CC1)OCCO2 ; COC(=O)[C@@H](NC(=O)OCc1ccccc1)C1CCC2(CC1)OCCO2]

The residue e from above was dissolved in H$_2$O (10 mL), AcOH (30 mL), THF (5 mL), and dichloroacetic acid (3 mL) and maintained at rt overnight. Water (5 mL) was added and the solution and maintained until hydrolysis was complete, as monitored by HPLC-MS. Solid Na$_2$CO$_3$ was added cautiously until gas evolution ceased, the mixture was diluted with aq NaHCO$_3$, and extracted with 10% EtOAc/DCM. The combined organic phases were washed once with brine, dried (Na$_2$SO$_4$), filtered, and concentrated. The residue was purified by chromatography to afford 2.9 g of product f.

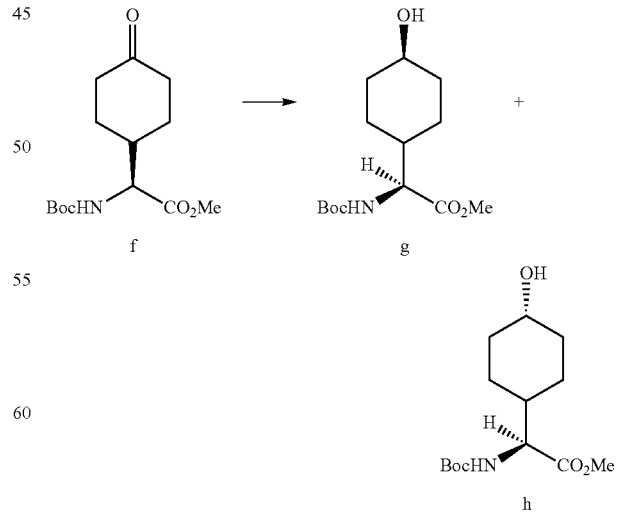

A mixture of ketone f (1.5 g) MeOH (50 ml) was treated with NaBH4 (290 mg) at 0° C. for 20 min. The mixture was acidified to ~pH1 with 10% aq citric acid and the MeOH was removed under reduced pressure. The residue was diluted with water and extracted with 20% EtOAc/DCM. The combined organic phases were washed once with brine, dried (Na$_2$SO$_4$), filtered, and concentrated. The residue was purified by chromatography to afford 1.17 g of product g and 0.23 g of product h.

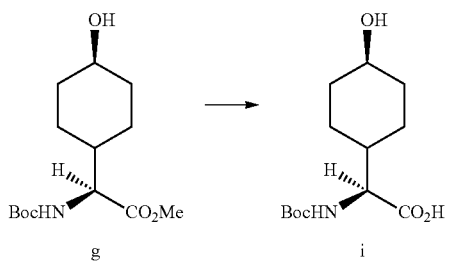

A mixture of ester g (1.17 g) LiOH.H2O (160 mg), THF (3 mL) and water (4.5 mL) was stirred vigorously at rt overnight. The mixture was diluted with brine and exhaustively extracted with EtOAc. The combined organic phases were washed once with brine, dried (Na$_2$SO$_4$), filtered, and concentrated to afford acid i (525 mg).

Example 6

N-Boc-N-cyclopropylmethyl-L-alanine

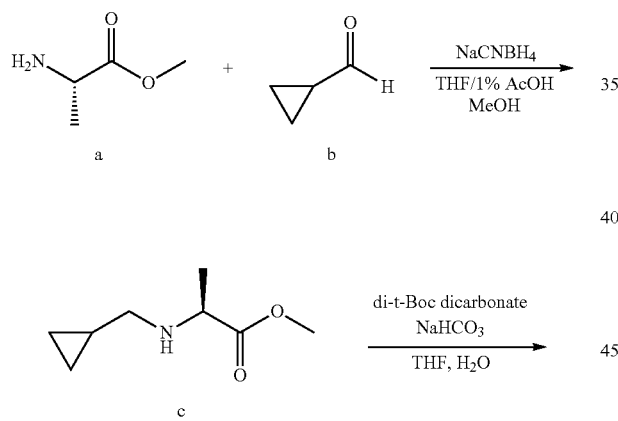

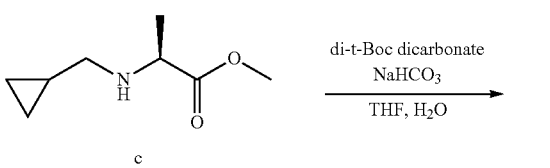

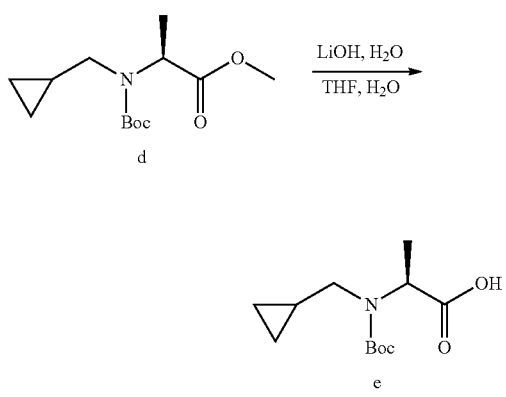

L-alanine methyl ester hydrochloride a (5 g, 35.8 mmol) and cyclopropanecarboxaldehyde b (2.67 ml, 35.8 mmol) were suspended in 50 ml THF w/1% AcOH. Addition of 5 ml of CH$_3$OH made the cloudy solution turned to clear. NaCNBH$_4$ (2.25 g, 35.8 mmol) was added and the reaction mixture stirred overnight. The reaction was quenched by addition of 1N aq. NaOH, extracted by EtOAc twice, organic layers were dried over Na$_2$SO$_4$ and concentrated to dryness. The crude material was purified by chromatography using 30% EtOAc/hexane (stained by ninhydrin) to obtain the compound c (1 g, 18%). The compound c (1 g, 6.37 mmol) and di-t-bocdicarbonate (2.1 g, 9.55 mmol) were diluted in THF (20 ml) and H$_2$O (20 ml), NaHCO$_3$ (1.3 g, 15.9 mmol) was added. The reaction mixture stirred overnight for completion. THF was removed under reduced pressure, and the aqueous layer was extracted by EtOAc 3 times. Combined organic layers were washed by 1N NaOH, sat, NH$_4$Cl followed by brine, the concentrated to dryness. The Boc-protected compound d (1.39 g, 5.40 mmol) was stirred with LiOH.H$_2$O (1.14 g, 27 mmol) in THF (20 ml) and H$_2$O (20 ml) overnight at room temperature. THF was stripped off, and the aqueous layer was adjusted to pH=4 by adding 10% citric acid, then extracted by EtOAc 3 times. Combined organic layers were washed by brine and concentrated. The crude was purified by reverse phase C-18 column eluted by 0%-50% acetonitrile/H$_2$O to give pure compound e as a white solid (794 mg).

Example 7

N-Boc-N-methyl-L-alanine-L-cyclohexylglycine

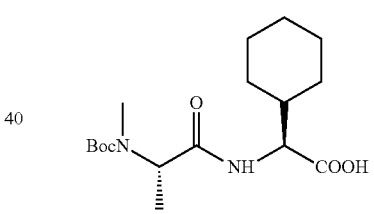

A solution of Fmoc-L-cyclohexylglycine (3.6 g, 9.6 mmol) dissolved in DCM (50 mL) and DIPEA (5.6 mL, 32 mmol) was added to 2-chlorotrityl chloride resin (5 g, 8 mmol) and gently agitated for 3 hours at room temperature. The resin was washed with DCM 4 times, DCM/MeOH/DIPEA (17:2:1) 3 times, DCM 3 times, and 2 times dimethylacetamide (DMA). The Fmoc group was removed by treating the resin with 20% piperidine/DMA (50 mL) for 15 minutes. The resin was washed with DMA 6 times. A solution of Boc-N-methylalanine (3.3 g, 16 mmol), HBTU (6.1 g, 16 mmol), and DIPEA (5.6 mL, 32 mmol) and DMA/DCM (1:1, 50 mL) was added to the resin and gently agitated for 2 hours at room temperature. The resin was washed with DMA 5 times, DCM 2 times, and dried under reduced pressure. The dipeptide was cleaved from the resin by gentle agitation with HOAc/TFE/DCM (1:1:3, 100 mL) for 2 hours at room temperature. The resin was removed by filtration and the solution concentrated. Residual AcOH was removed by azeotroping with hexanes (15 times volume). The solid residue was purified by reverse-phase HPLC(C$_{18}$, MeCN—H$_2$O, 0.1% TFA) and the solvents removed by lyophilization to provide 1.2 g (43%) of dipeptide N-Boc-N-methyl-L-alanine-L-cyclohexylglycine as a white powder.

Example 8

N-Boc-N-methyl-L-alanine-L-dehydropyranylglycine

CH$_2$Cl$_2$ (3×20 mL). The combined organic phases were washed with brine (1×50 mL), dried (Na$_2$SO$_4$), filtered, adsorbed onto Celite and chromatographed (ISCO, 120 g silica column, gradient elution 5-55% EtOAc-hexanes) to afford 4.15 g (80%) of racemic Cbz-pyranylglycine methyl ester. The enantiomers were separated on a Chiracel OD column eluting with 10% EtOH-hexanes. The desired S-enantiomer c elutes first under these conditions.

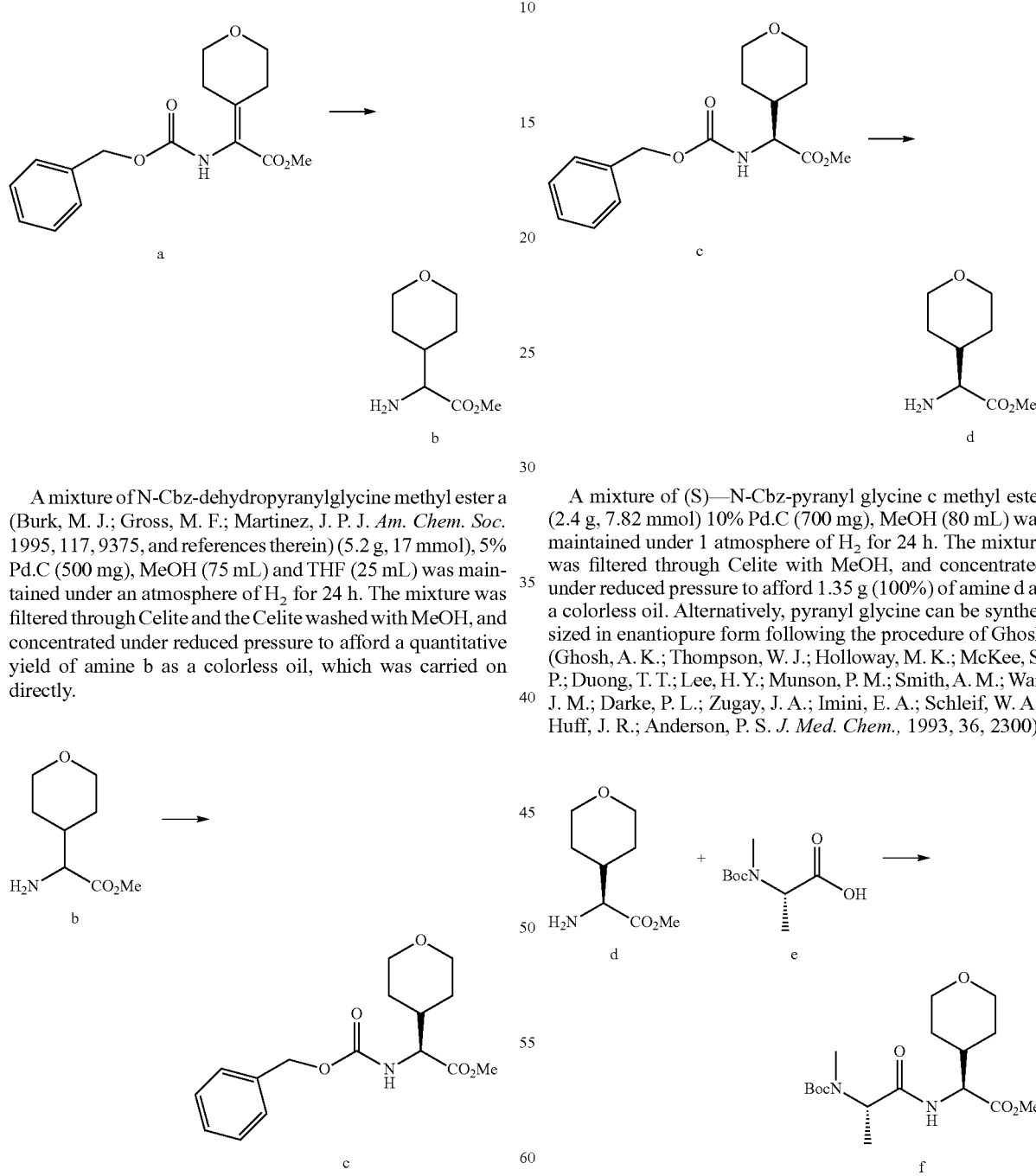

A mixture of N-Cbz-dehydropyranylglycine methyl ester a (Burk, M. J.; Gross, M. F.; Martinez, J. P. J. *Am. Chem. Soc.* 1995, 117, 9375, and references therein) (5.2 g, 17 mmol), 5% Pd.C (500 mg), MeOH (75 mL) and THF (25 mL) was maintained under an atmosphere of H$_2$ for 24 h. The mixture was filtered through Celite and the Celite washed with MeOH, and concentrated under reduced pressure to afford a quantitative yield of amine b as a colorless oil, which was carried on directly.

A mixture of (S)—N-Cbz-pyranyl glycine c methyl ester (2.4 g, 7.82 mmol) 10% Pd.C (700 mg), MeOH (80 mL) was maintained under 1 atmosphere of H$_2$ for 24 h. The mixture was filtered through Celite with MeOH, and concentrated under reduced pressure to afford 1.35 g (100%) of amine d as a colorless oil. Alternatively, pyranyl glycine can be synthesized in enantiopure form following the procedure of Ghosh (Ghosh, A. K.; Thompson, W. J.; Holloway, M. K.; McKee, S. P.; Duong, T. T.; Lee, H. Y.; Munson, P. M.; Smith, A. M.; Wai, J. M.; Darke, P. L.; Zugay, J. A.; Imini, E. A.; Schleif, W. A.; Huff, J. R.; Anderson, P. S. *J. Med. Chem.*, 1993, 36, 2300).

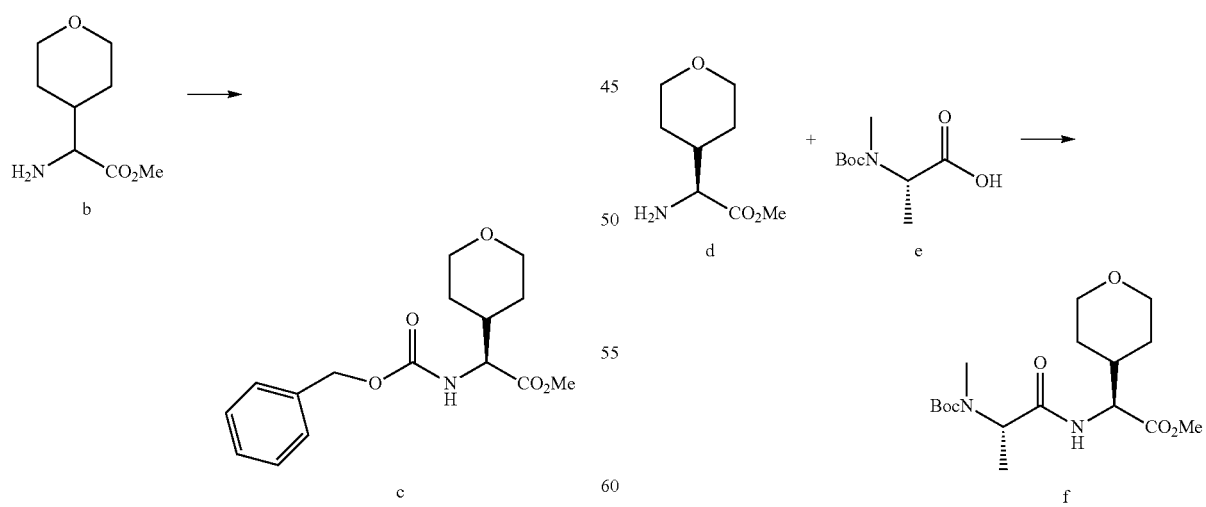

The amine b prepared above was combined with CH$_2$Cl$_2$ (40 mL), saturated aqueous NaHCO$_3$ (40 mL) and cooled to 0° C. Benzyloxy carbonyl chloride (3.0 mL) was then added dropwise and the mixture stirred vigorously overnight. The phases were separated and the aqueous phase extracted with A mixture of amine d (1.35 g, 7.8 mmol), N-Boc-N-methyl alanine e (1.74 g, 8.6 mmol), EDC (1.65 g 8.8 mmol) and MeCN (50 mL) was maintained at rt overnight. The MeCN was removed under reduced pressure, and the residue diluted with EtOAc, washed with 0.5 N HCl (3×10 mL), 0.5 N NaOH (3×10 mL), dried (MgSO₄), filtered, and concentrated to provide 2.1 g (75%) of protected dipeptide f, as a clear oil.

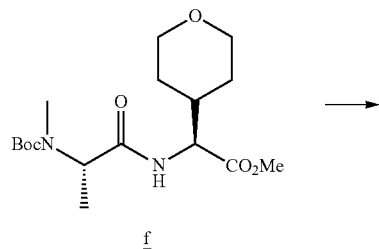

f

To a 0° C. solution of ester f (2.10 g, 5.86 mmol) and THF (50 mL) were added LiO.H₂O (1.23 g, 29.3 mmol) and water (2 mL). The mixture was maintained at 0° C. for 2 h, then the cooling bath was removed and the mixture was stirred overnight. Most of the THF was then removed under reduced pressure and the residue was diluted with CH₂Cl₂, washed with 0.5 N HCl, dried (MgSO₄), filtered, and concentrated to provide 1.53 g (78%) of dipeptide N-Boc-N-methyl-L-alanine-L-dehydropyranylglycine g, as a colorless solid.

Example 9

(S)-tert-butyl 2-(4-phenylbenzo[d]thiazol-2-yl)pyrrolidine-1-carboxylate biphenyl a (0.89 g, 5.3 mmol) was then added in a single portion, and stirring was continued at room temperature for 2 h. The solution was then heated to 45° C. for 5 h and cooled to room temperature over 16 h. The reaction was then poured into 250 ml of water, to which was added 50 ml of brine. The aqueous phase was extracted 3 times with 50 ml EtOAc, and the organics combined. The organic phases were then washed with 100 ml 1 M HCl and 100 ml brine before being dried with MgSO₄, filtered and concentrated to an oil. This oil was adsorbed onto silica gel and purified by flash chromatography (40 g SiO₂, 0% to 40% EtOAc in hexanes) to afford the desired amide b as a clear oil (1.2 g, 3.3 mmol, 71%).

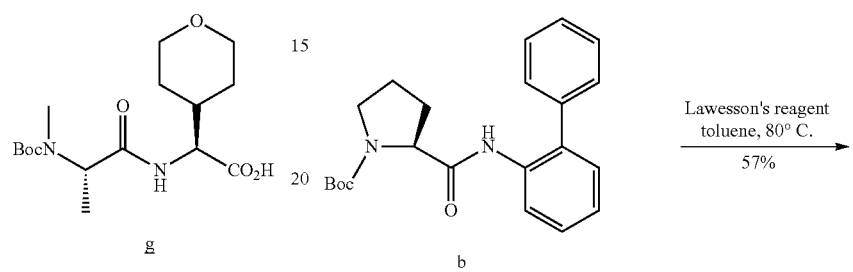

To a stirred solution of b (1.06 g, 2.9 mmol) in 30 ml toluene was added Lawesson's reagent (0.69 g, 1.7 mmol) in a single portion. The reaction was warmed to 80° C. on an oil bath for 3 h, then cooled to room temperature over 16 h. The solution was adsorbed onto silica gel and purified by flash chromatography (40 g SiO₂, 0% to 40% EtOAc in hexanes) to afford the desired thioamide c as a clear oil (0.63 g, 1.6 mmol, 57%).

To a stirred solution of Boc-L-proline (1.0 g, 4.6 mmol) in 50 ml of dry DMF was added DIPEA (2.4 ml, 13.8 mmol), followed by HATU (1.75 g, 4.6 mmol). The resulting solution was stirred for 5 minutes at room temperature. 2-amino- To a stirred solution of K₃Fe(CN)₆ (1.51 g, 4.6 mmol) in 4 ml water at 85° C. was slowly added a suspension of c obtained by initially wetting c (0.42 g, 1.1 mmol) with a few drops of EtOH, then adding a 30% solution of NaOH (1.2 ml, 9.0 mmol) and pipetting vigorously for a several minutes. After addition was complete, the reaction was stirred for 2½ hours at 85° C., after which the reaction was diluted with 25 ml water and filtered. The filtrate was dissolved in dichloromethane and adsorbed onto silica gel and purified by flash chromatography (12 g SiO₂, 0% to 25% EtOAc in hexanes) to give (S)-tert-butyl 2-(4-phenylbenzo[d]thiazol-2-yl)pyrrolidine-1-carboxylate d (0.22 g, 0.58 mmol, 52%).

Example 10

(S)-tert-butyl 2-(4-methylbenzo[d]thiazol-2-yl)pyrrolidine-1-carboxylate

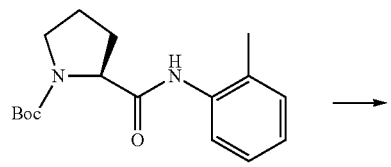

a

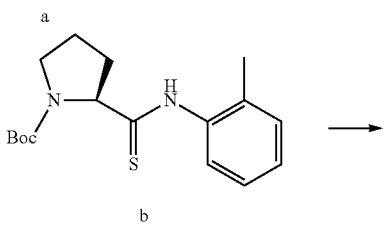

b

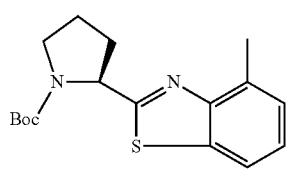

c

Compound c was prepared according to procedures in example 9, above. Ortho-toluidine (0.72 ml, 6.7 mmol) was converted to compound a (1.49 g, 4.9 mmol, 87%). Compound a (1.14 g, 3.7 mmol) was then converted to compound b (0.27 g, 0.84 mmol, 23%). Compound b (0.27 g, 0.84 mmol), was converted to compound c.

Example 11

(S)-tert-butyl 2-(4-isopropylbenzo[d]thiazol-2-yl) pyrrolidine-1-carboxylate

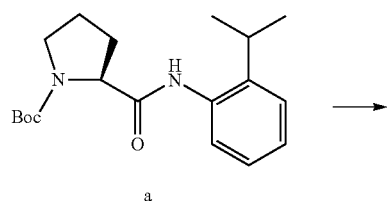

a

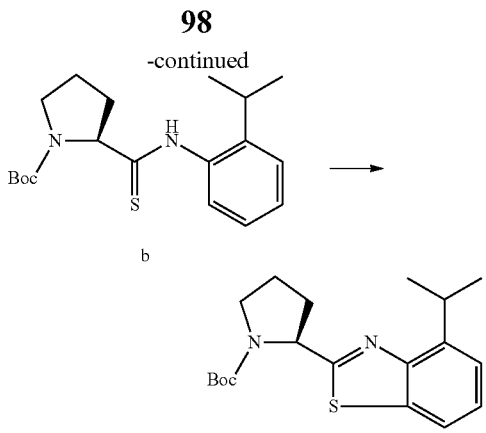

b c

Compound c was prepared according to procedures in example 9. 2-isopropylaniline (0.9 ml, 5.2 mmol) was converted to compound a (1.53 g, 4.9 mmol, 87%). Compound a (1.53 g, 4.9 mmol) was then converted to compound b (1.14 g, 3.3 mmol, 67%). Compound b (1.14 g, 3.3 mmol), was converted to (S)-tert-butyl 2-(4-isopropylbenzo[d]thiazol-2-yl) pyrrolidine-1-carboxylate c (0.35 g, 1.0 mmol, 31%).

Example 12

(S)-tert-butyl 2-(4-benzylbenzo[d]thiazol-2-yl)pyrrolidine-1-carboxylate

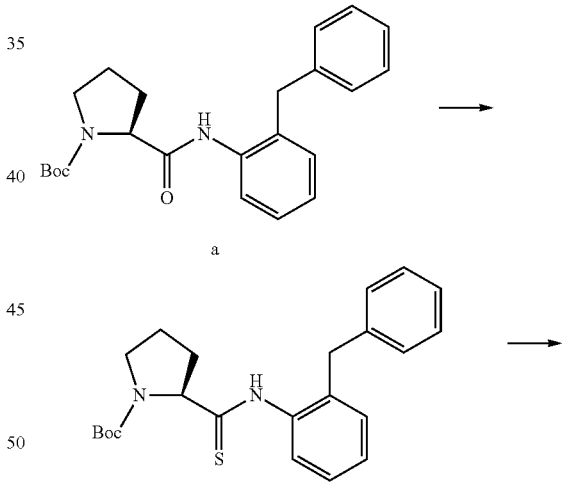

a b

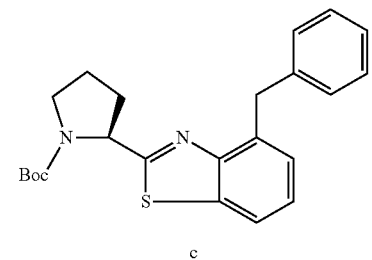

c

Compound c was prepared according to procedures in example 9. 2-benzyl aniline (1.18 g, 6.4 mmol) was converted to compound a (1.43 g, 3.8 mmol, 59%). Compound a (1.18 g, 3.1 mmol) was then converted to compound b (0.85 g, 2.1 mmol, 69%). Compound b (0.85 g, 2.1 mmol), was converted to (S)-tert-butyl 2-(4-benzylbenzo[d]thiazol-2-yl)pyrrolidine-1-carboxylate c (0.18 g, 0.46 mmol, 22%).

Example 13

7-phenyl-2-(pyrrolidin-2-yl)thiazolo[5,4-b]pyridine

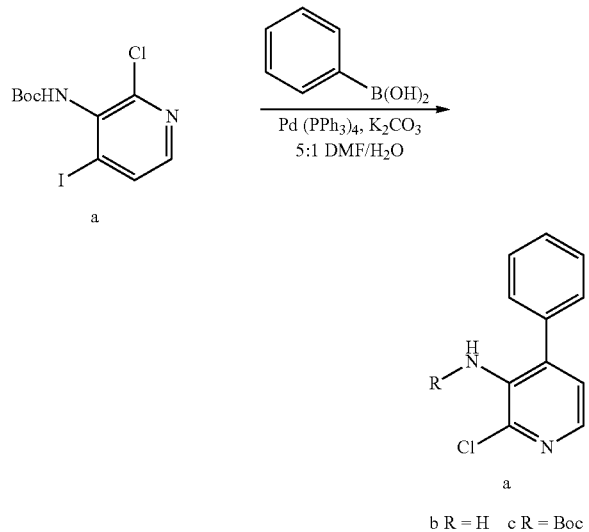

(2-chloro-4-iodo-pyridin-3-yl)-carbamic acid tert-butyl ester a (4.20 g, 11.8 mmol), phenyl boronic acid (1.90 g, 15.6 mmol), potassium carbonate (2.42 g, 17.5 mmol) and tetrakistriphenylphosphine palladium(0) (0.68 g, 0.59 mmol) were weighed into a 20 ml microwave vial. The vial was evacuated, then purged with nitrogen gas 3 times. 16.7 ml dry DMF was added, then 3.3 ml of water, which had been degassed by bubbling nitrogen through it overnight. The vial was then capped and microwaved at 130° C. for 40 minutes. The resulting solution was poured into 250 ml water and extracted with EtOAc (3×50 ml). The combined organics were dried with $MgSO_4$, filtered and concentrated. The resulting oil was adsorbed onto silica gel and purified by flash chromatography (150 g $SiO_2$, 0% to 40% EtOAc in hexanes) to give 2-chloro-3-amino-4-phenyl pyridine b (0.84 g, 4.1 mmol, 35%) and the Boc-protected 2-chloro-3-amino-4-phenyl pyridine c (1.74 g, 5.7 mmol, 48%) as yellow and white solids, respectively.

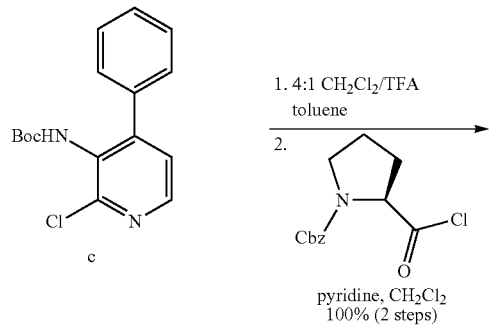

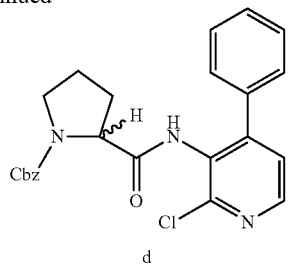

Compound c (1.74 g, 5.7 mmol) was dissolved in 50 ml of 4:1 methylene chloride/TFA and 1 ml of toluene was added. The resulting solution was heated to 40° C. for 2 h, after which the reaction mixture was concentrated to a yellowish solid. This solid was dissolved in 50 ml methylene chloride and washed with 100 ml aqueous 1N NaOH. After the layers were separated, the aqueous phase was extracted a further two times with 50 ml methylene chloride. The organic extracts were combined, dried with $MgSO_4$, filtered and concentrated to a yellow solid, which was carried on without further purification.

To a stirred solution of 2-chloro-3-amino-4-phenyl pyridine in dry methylene chloride was added pyridine (2.5 ml, 30.9 mmol) and then (S)-benzyl 2-(chlorocarbonyl)pyrrolidine-1-carboxylate (1.83 g, 6.8 mmol) prepared in example 14, dropwise. The reaction mixture was stirred 16 h under a nitrogen atmosphere, then poured into 200 ml of 1N HCl. The layers were separated, and the aqueous phase extracted with methylene chloride (3×50 ml). The combined organics were dried with $MgSO_4$, filtered and concentrated. The resulting oil was adsorbed onto silica gel and purified by flash chromatography (40 g $SiO_2$, 0% to 60% EtOAc in hexanes) to give the desired amide d as a foam (2.51 g, 5.8 mmol, 100%).

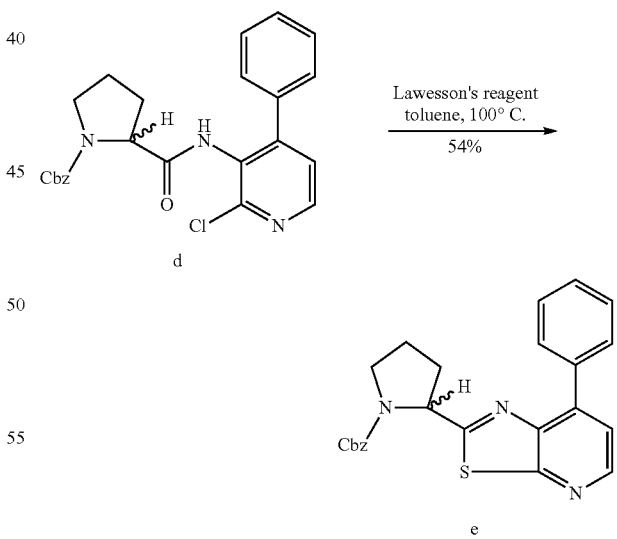

Compound d (2.51 g, 5.76 mmol) and Lawesson's reagent (1.37 g, 3.4 mmol) were dissolved in 50 mL of dry toluene and heated to 100° C. for 16 hours. The solution was cooled, then adsorbed onto silica gel and purified by flash chromatography (120 g $SiO_2$, 0% to 40% EtOAc in hexanes) to give the desired 7-aza benzothiazole e as a white foam (1.30 g, 3.1 mmol, 54%).

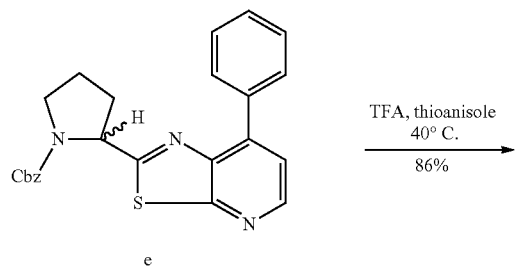

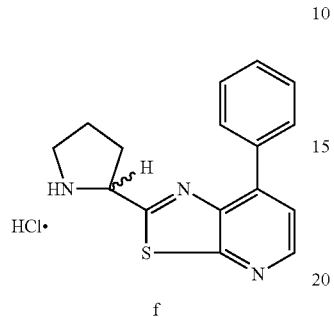

Compound e (1.30 g, 3.1 mmol) was dissolved in 30 ml TFA. Thioanisole (2.9 ml, 24.7 mmol) was added, and the solution was warmed to 40° C. for 16 hours. The volatiles were then removed under vacuum, and the resulting oil dissolved in diethyl ether (50 mL). The solution was poured into 1 N NaOH (200 ml) and the layers separated. The aqueous phase was extracted with diethyl ether (2×50 ml) and the organics combined. The organic phases were dried with $MgSO_4$, and filtered. 4 N HCl in dioxane (0.8 ml, 3.2 mmol) was added, and a white solid precipitated. The material was cooled to 4° C. for 4 hours, then filtered, washing with cold diethyl ether (3×50 ml) to give 7-phenyl-2-(pyrrolidin-2-yl)thiazolo[5,4-b]pyridine hydrochloride salt f (0.852 g, 2.7 mmol, 86%) as fine white crystals.

Example 14

(S)-benzyl 2-(chlorocarbonyl)pyrrolidine-1-carboxylate

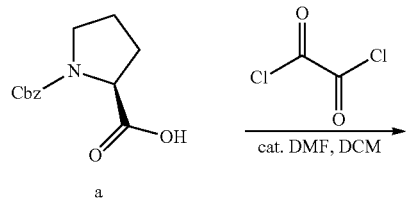

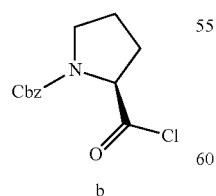

Cbz-Pro-OH a (2.0 g, 8.0 mmol) was dissolved in DCM (10 mL) and oxalyl chloride (6 mL of a 2M solution, 12.0 mmol) was added. DMF (2 drops) was added and the mixture was stirred at room temperature for 30 min. The solution was concentrated to afford 2.1 g (100%) of acid chloride (S)-benzyl 2-(chlorocarbonyl)pyrrolidine-1-carboxylate b as a pale yellow oil.

Example 15

7-phenyl-2-((S)-pyrrolidin-2-yl)thiazolo[5,4-c]pyridine

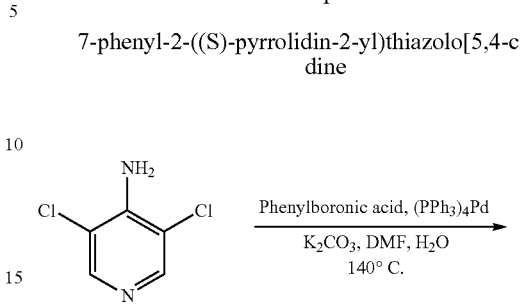

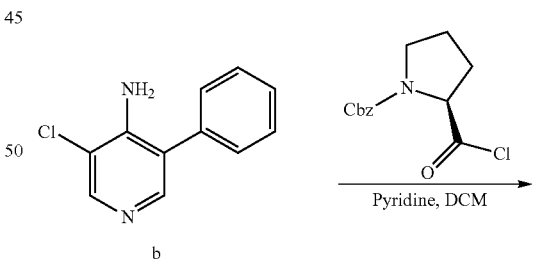

4-amino-3,5-dichloropyridine a (2.0 g, 12.3 mmol), tetrakis(triphenylphosphine)palladium (696 mg, 0.6 mmol), phenylboronic acid (1.9 g, 15.9 mmol) and potassium carbonate (2.2 g, 15.9 mmol) were mixed in a 10 mL microwave vial under $N_2$ atmosphere. DMF (6 mL) and deoxygenated $H_2O$ (1.2 mL) were added. $N_2$ was bubbled through the mixture for 5 min and the mixture was heated for 20 min at 140° C. in the microwave. The mixture was diluted with water (30 mL) and extracted with EtOAc (3×20 mL). The combined organic phases were washed with water (50 mL) and brine (50 mL), dried with $MgSO_4$, filtered and concentrated. The resulting brown oil was adsorbed on silica gel and purified by flash chromatography ($SiO_2$, 0% to 70% ethyl acetate/hexanes) to afford 970 mg (37%) of b as a colorless oil. MS: m/z=205 (M+H).

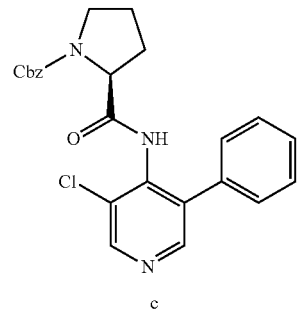

4-amino-3-chloro-5-phenylpyridine b (650 mg, 3.16 mmol) was dissolved in DCM (10 mL). Cbz-Pro-Cl (1.6 g, 6.3 mmol), dissolved in DCM (5 mL) was added, followed by pyridine (467 mg, 6.3 mmol) and the mixture was stirred overnight at room temperature. The reaction was quenched with 0.5N HCl, the phases were separated and the aqueous phase was extracted with DCM (2×20 mL). The combined organic phases were dried with MgSO₄, filtered and concentrated. The resulting oil was adsorbed on silica gel and purified by flash chromatography (SiO₂, 0% to 100% EtOAc/hexanes) to afford 1.12 g (80%) of c as a colorless oil. MS: m/z=436 (M+H).

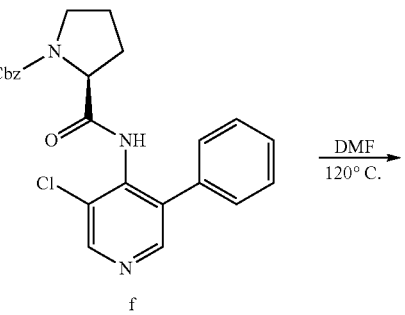

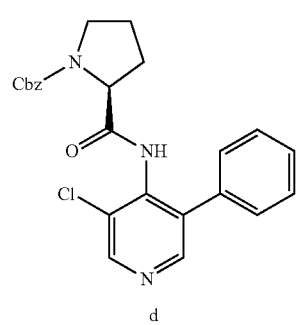

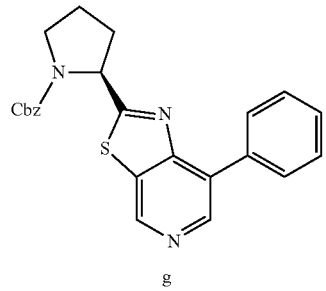

Compound f was dissolved in DMF (5 mL) and the solution was stirred at 120° C. for 3 days. The mixture was cooled to room temperature, diluted with 20 mL of H₂O and extracted with EtOAc (3×25 mL). The combined organic phases were washed with water (50 mL) and brine (50 mL), dried with MgSO₄, filtered and concentrated. The resulting oil was adsorbed on silica gel and purified by flash chromatography (SiO₂, hexanes to ethyl acetate) to afford 423 mg (98%) of g as a yellow oil. MS: m/z=415 (M+H).

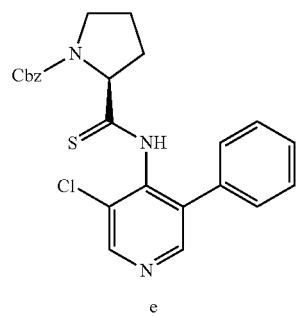

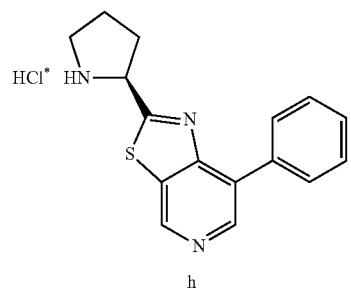

Following the general procedure of Charette (Charette, A. B. et al, *J. Org. Chem.*, 2003, 68, 5792-5794), compound d (1.7 g, 3.9 mmol) and pyridine (0.89 mL, 4.7 mmol) were mixed together in DCM (20 mL) at 0° C. and the solution was stirred for 5 min. Trifluoromethanesulfonic anhydride (1.3 g, 4.7 mmol) was slowly added. The solution was stirred for 3 h and allowed to warm up to room temperature. The reaction was quenched by rapid addition of 20% aqueous ammonium sulfide (2.0 mL, 5.8 mmol) and stirred overnight at room temperature. The mixture was filtered through a pad of silica gel and washed with DCM (50 mL). The filtrate was concentrated and the resulting oil was adsorbed on silica gel and purified by flash chromatography (SiO₂, 0% to 70% ethyl acetate/hexanes) to afford 500 mg (28%) of e as a yellow solid. MS: m/z=452 (M+H).

Compound g (423 mg, 1.0 mmol) and thioanisole (993 mg, 8.0 mmol) were dissolved in TFA (40 mL). The mixture was stirred at 40° C. overnight. The mixture was cooled to room temperature and concentrated. The residual oil was dissolved in ether (20 mL) and washed with 1N NaOH (30 mL). The aqueous phase was extracted with ether (2×20 mL). The combined organic phases were dried with MgSO₄ and filtered. 4N HCl in dioxane was added until a solid precipitated. The solid was collected by filtration, washed with ether and air dried to afford 240 mg (76%) of 7-phenyl-2-((S)-pyrrolidin-2-yl)thiazolo[5,4-c]pyridine h as a pale yellow solid. MS: m/z=282 (M+H).

Example 16

7-phenyl-2-((S)-pyrrolidin-2-yl)thiazolo[5,4-d]pyrimidine

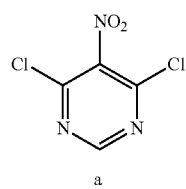

a

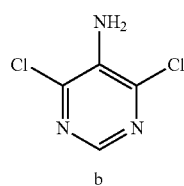

b

Iron powder (12.5 g, 112 mmol) was added to a suspension of 4,6-dichloro-5-nitropyrimidine a (7.0 g, 36.1 mmol) in acetic acid (70 mL). The mixture was stirred at 40° C. for 45 min. The mixture was poured onto ice and neutralized by addition of solid sodium bicarbonate. The aqueous phase was extracted with EtOAc (3×200 mL). The combined organic phases were dried with MgSO₄, filtered and concentrated to afford a pale yellow solid. Recrystallization in hot ethyl acetate afforded 3.6 g (61%) of compound b as off-white needles. MS: m/z=165 (M+H).

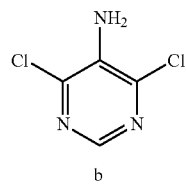

b

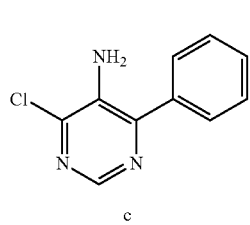

c

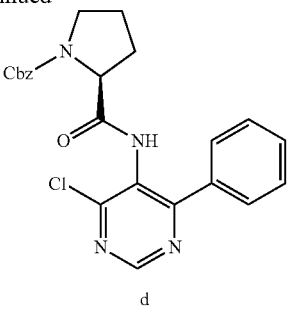

d

Compound c was prepared from compound b (1.0 g, 6.1 mmol) using the general procedure for preparing compound b in example 15. The procedure afforded 410 mg (28%) of c as a yellow solid. MS: m/z=206 (M+H). Compound d was prepared from compound c (270 mg, 1.3 mmol) using the general procedure for preparing compound c in example 15. The procedure afforded 565 mg (99%) of d as a colorless oil. MS: m/z=437 (M+H).

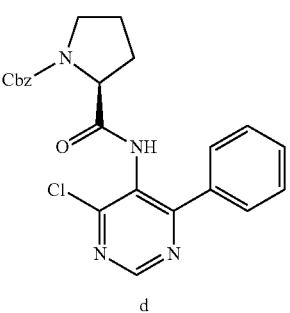

d

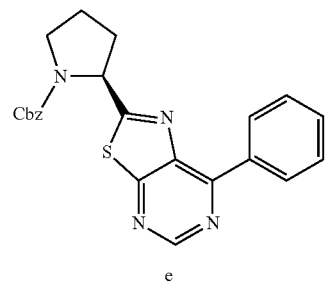

e

A mixture of compound d (550 mg, 1.26 mmol) and Lawesson's reagent (341 mg, 0.84 mmol) in toluene (10 mL) was heated at 80° C. overnight. The solution was concentrated, adsorbed on silica gel and purified by flash chromatography (SiO₂, 0% to 60% ethyl acetate/hexanes) to afford 514 mg (98%) of e as a pale yellow solid. MS: m/z=417 (M+H).

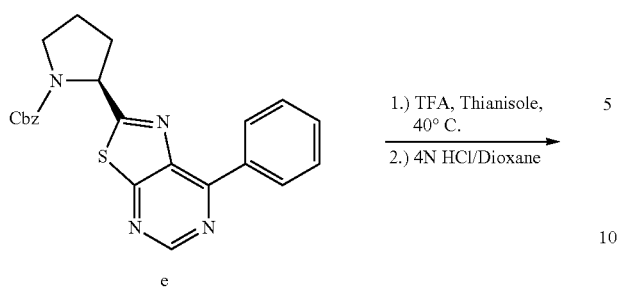

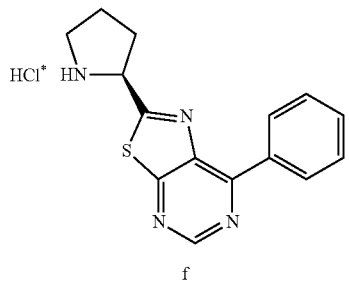

Compound f was prepared from compound e (510 mg, 1.2 mmol) using procedure for preparing compound h in example 15. The procedure afforded 378 mg (98%) of 7-phenyl-2-((S)-pyrrolidin-2-yl)thiazolo[5,4-d]pyrimidine f as an off-white solid. MS: m/z=283 (M+H).

Example 17

2,3-diaminobiphenyl

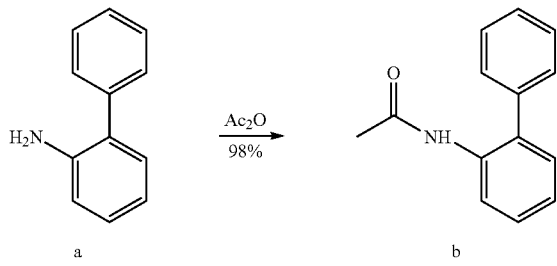 [SMILES: "Ac2O" ; Nc1ccccc1-c1ccccc1 ; CC(=O)Nc1ccccc1-c1ccccc1]

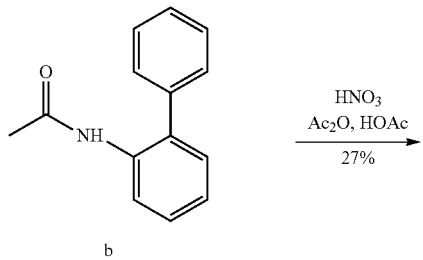

2-Aminobiphenyl a (21.9289 g, 130 mmol) was dissolved in Ac$_2$O (30 mL, 318 mmol) and stirred 10 minutes. An additional portion of Ac$_2$O (10 mL, 106 mmol) was added then stirred for 10 more minutes. The sample was poured onto ice. The resulting solid was vacuum filtered and washed with H$_2$O to give N-acetyl-2-aminobiphenyl b (26.955 g, 128 mmol, 98%).

Following the general procedure of Stepan (Stepan, A. H., et al, *J. Am. Chem. Soc.*, 1949, 71, 2438), N-acetyl-2-amino-biphenyl b (7.198 g, 34.1 mmol), HOAc (6 mL), and Ac$_2$O (5 mL) were mixed and heated at 120° C. for a few minutes until N-acetyl-2-aminobiphenyl b was dissolved. The sample was cooled to room temperature. HOAc (1.5 mL) was added slowly to 2.3 mL of fuming HNO$_3$ (2.3 mL, 54.5 mmol) in an ice bath. While maintaining a temperature of less than 26.5° C., 1.5 mL of the HNO$_3$ mixture was added quickly then the remaining HNO$_3$ mixture was added drop wise to N-acetyl-2-aminobiphenyl b. The sample was stirred at room temperature for 4 hours then stored at 4° C. overnight. The reaction mixture was poured into ice and extracted once with benzene. The benzene layer was stored at 4° C. for 1 hour. The resulting solid was vacuum filtered and washed with cold benzene to give N-acetyl-2-amino-3-nitrobiphenyl c (2.346 g, 9.15 mmol, 27%).

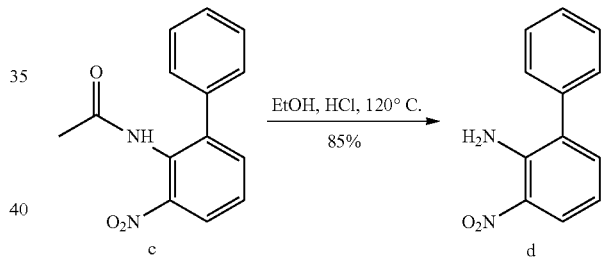

N-Acetyl-2-amino-3-nitrobiphenyl c (1.008 g, 3.93 mmol), EtOH (19 mL, 325 mmol), and concentrated HCl (5 mL, 50 mmol) were mixed and refluxed at 120° C. overnight. The sample was adsorbed onto silica gel and purified by flash chromatography (12 g SiO$_2$, 0-33% EtOAc in hexanes) to give 2-amino-3-nitrobiphenyl d (0.720 g, 3.36 mmol, 85%)

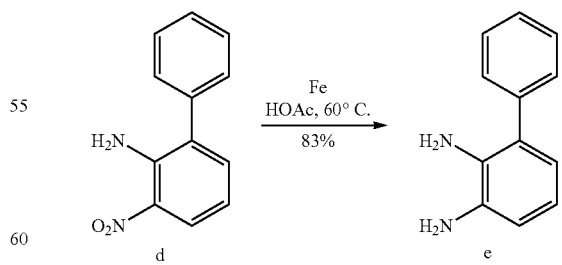

2-Amino-3-nitrobiphenyl d (0.613 g, 2.86 mmol) was purged under nitrogen for 30 minutes then HOAc (5 mL) was added followed by iron powder (0.4895 g, 8.76 mmol). The sample was heated at 60° C. for 30 minutes then HOAc (5 mL) was added. The sample was stirred at 60° C. for 1 hour then poured into ice. The sample was extracted with EtOAc (3×100 mL). The EtOAc extracts were washed with saturated NaHCO₃ (3×100 mL. The EtOAc layer was dried over MgSO₄, filtered, and concentrated to give 2,3-diaminobiphenyl e (0.439 g, 2.38 mmol, 83%).

Example 18

2(S)-[[(2-Iodophenyl)amino]carbonyl]-1-(1,1-dimethylethylester)-1-pyrrolidinecarboxylic acid

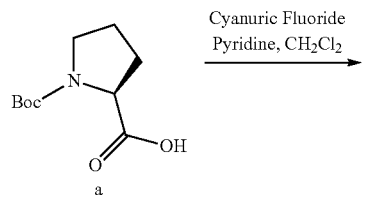

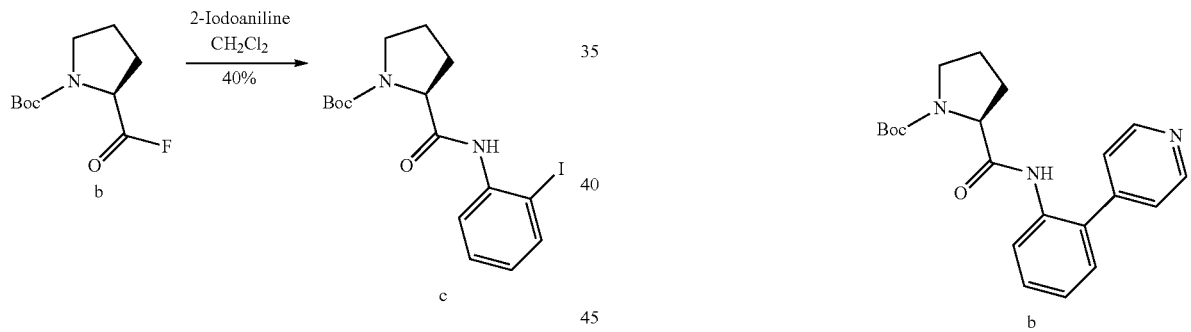

Boc-Pro-OH a (5.0030 g, 23.2 mmol) was dissolved in dry CH₂Cl₂ (50 mL) then cooled to 0° C. Dry pyridine (3.8 mL, 46.4 mmol) was added. Cyanuric fluoride (2.2 mL, 25.5 mmol) was added drop wise. The sample was warmed to room temperature and stirred for 30 minutes. H₂O (5 mL) was added to quench the reaction. The reaction mixture was diluted with H₂O and extracted three times with CH₂Cl₂. The CH₂Cl₂ extracts were washed with saturated NaCl, The CH₂Cl₂ layer was dried over MgSO₄, filtered, and concentrated to give the acid fluoride b which was used without further purification. The acid fluoride b was dissolved in dry CH₂Cl₂ (50 mL). 2-Iodoaniline (4.9932 g, 22.8 mmol) was added, and the sample was stirred overnight. The reaction mixture was adsorbed onto silica gel and purified by flash chromatography (80 g SiO₂, 0-50% EtOAc in hexanes) to give 2(S)-[[(2-iodophenyl)amino]carbonyl]-1-(1,1-dimethylethylester)-1-pyrrolidinecarboxylic acid c (3.845 g, 9.24 mmol, 40%).

Example 19

2(S)-[[(2-(4-pyridyl)phenyl)amino]carbonyl]-1-(1,1-dimethylethylester)-1-pyrrolidinecarboxylic acid

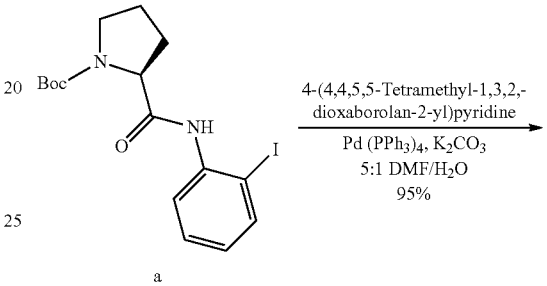

2(S)-[[(2-Iodophenyl)amino]carbonyl]-1-(1,1-dimethylethylester)-1-pyrrolidinecarboxylic acid a (0.4810 g, 1.16 mmol), 4-(4,4,5,5-Tetramethyl-1,3,2-dioxaborolan-2-yl)pyridine (0.3240 g, 1.58 mmol), K₂CO₃ (0.2190 g, 1.58 mmol), and Pd(PPh₃)₄ (0.0702 g, 0.0607 mmol) were combined in a 5 mL microwave vial. The sample was evacuated and purged with nitrogen three times, Dry DMF (2 mL) and deoxygenated H₂O (0.4 mL) were added. The sample was microwaved at 130° C. for 10 minutes. The reaction mixture was diluted with H₂O and extracted three times with EtOAc. The EtOAc extracts was dried over MgSO₄, and filtered. The crude material was adsorbed onto silica gel and purified by flash chromatography (4 g SiO₂, 0-100% EtOAc in hexanes) to give the 2(S)-[[(2-(4-pyridyl)phenyl)amino]carbonyl]-1-(1,1-dimethylethylester)-1-pyrrolidinecarboxylic acid b (0.404 g, 1.10 mmol, 95%).

Example 20

2(S)-[[(2-(3'-Chloro(1,1'-biphenyl))amino]carbonyl]-1-(1,1-dimethylethylester)-1-pyrrolidinecarboxylic acid

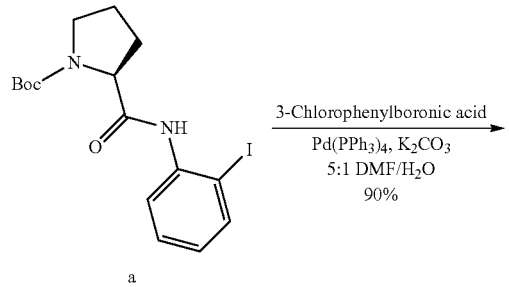

a

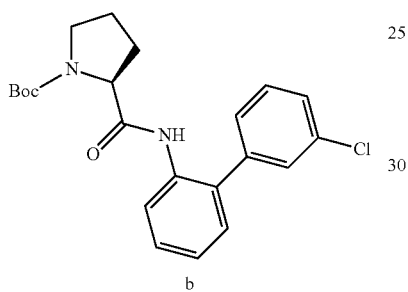

b

Following the procedure of example 19, 2(S)-[[(2-Iodophenyl)amino]carbonyl]-1-(1,1-dimethylethylester)-1-pyrrolidinecarboxylic acid a (0.4576 g, 1.10 mmol), 3-chlorophenylboronic acid (0.2520 g, 1.61 mmol), $K_2CO_3$ (0.2431 g, 1.76 mmol), and $Pd(PPh_3)_4$ (0.0725 g, 0.0627 mmol) gave the 2 (S)-[[(2-(3'-chloro(1,1'-biphenyl))amino]carbonyl]-1-(1,1-dimethylethylester)-1-pyrrolidinecarboxylic acid b (0.399 g, 0.995 mmol, 90%).

Example 21

2(S)-[[(2-(2'-Chloro(1,1'-biphenyl))amino]carbonyl]-1-(1,1-dimethylethylester)-1-pyrrolidinecarboxylic acid

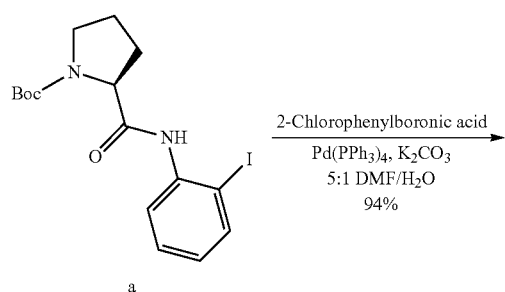

a

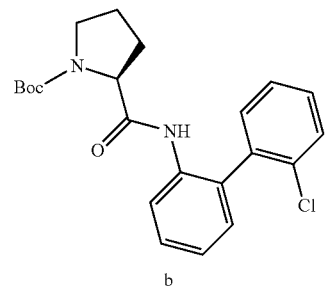

b

Following the procedure of example 19, 2(S)-[[(2-Iodophenyl)amino]carbonyl]-1-(1,1-dimethylethylester)-1-pyrrolidinecarboxylic acid a (0.4554 g, 1.09 mmol), 2-chlorophenylboronic acid (0.2518 g, 1.59 mmol), $K_2CO_3$ (0.2592 g, 1.88 mmol), and $Pd(PPh_3)_4$ (0.0752 g, 0.0651 mmol) gave the 2(S)-[[(2-(2'-chloro(1,1'-biphenyl))amino]carbonyl]-1-(1,1-dimethylethylester)-1-pyrrolidinecarboxylic acid b (0.414 g, 1.03 mmol, 94%).

Example 22

2(S)-[[(2-(4'-Chloro(1,1'-biphenyl))amino]carbonyl]-1-(1,1-dimethylethylester)-1-pyrrolidinecarboxylic acid

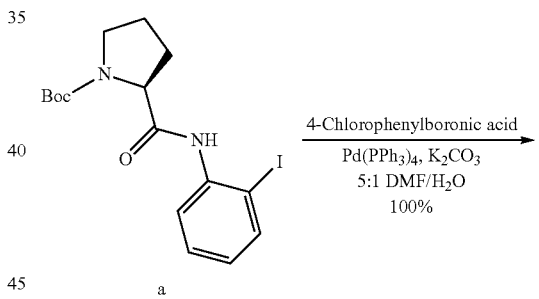

a

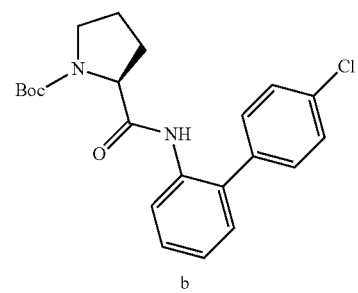

b

Following the procedure of example 19, 2(S)-[[(2-Iodophenyl)amino]carbonyl]-1-(1,1-dimethylethylester)-1-pyrrolidinecarboxylic acid a (0.4494 g, 1.08 mmol), 4-chlorophenylboronic acid (0.2561 g, 1.62 mmol), $K_2CO_3$ (0.2639 g, 1.91 mmol), and $Pd(PPh_3)_4$ (0.0732 g, 0.0633 mmol) gave the 2(S)-[[(2-(4'-chloro(1,1'-biphenyl))amino]carbonyl]-1-(1,1-dimethylethylester)-1-pyrrolidinecarboxylic acid b (0.411 g, 1.08 mmol, 100%).

Example 23

2(S)-[[(2-(3'-Fluoro(1,1'-biphenyl))amino]carbonyl]-1-(1,1-dimethylethylester)-1-pyrrolidinecarboxylic acid

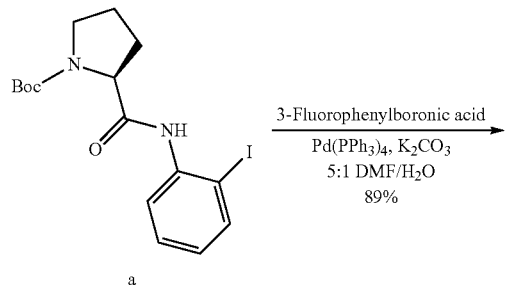

a

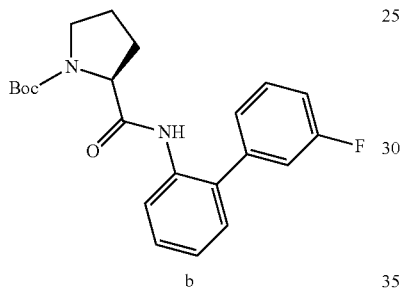

b

Following the procedure of example 19, 2(S)-[[(2-Iodophenyl)amino]carbonyl]-1-(1,1-dimethylethylester)-1-pyrrolidinecarboxylic acid a (0.4507 g, 1.08 mmol), 3-fluorophenylboronic acid (0.2158 g, 1.54 mmol), $K_2CO_3$ (0.2343 g, 1.69 mmol), and $Pd(PPh_3)_4$ (0.0756 g, 0.0654 mmol) gave the 2(S)-[[(2-(3'-fluoro(1,1'-biphenyl))amino]carbonyl]-1-(1,1-dimethylethylester)-1-pyrrolidinecarboxylic acid b (0.387 g, 1.01 mmol, 89%).

Example 24

2(S)-[[(2-(2'-Fluoro(1,1'-biphenyl))amino]carbonyl]-1-(1,1-dimethylethylester)-1-pyrrolidinecarboxylic acid

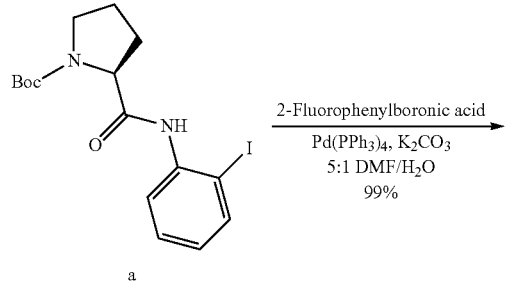

a

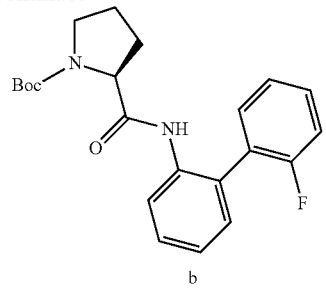

b

Following the procedure of example 19, 2(S)-[[(2-Iodophenyl)amino]carbonyl]-1-(1,1-dimethylethylester)-1-pyrrolidinecarboxylic acid a (0.4487 g, 1.08 mmol), 2-fluorophenylboronic acid (0.2154 g, 1.54 mmol), $K_2CO_3$ (0.2305 g, 1.67 mmol), and $Pd(PPh_3)_4$ (0.0663 g, 0.0574 mmol) gave the 2(S)-[[(2-(2'-fluoro(1,1'-biphenyl))amino]carbonyl]-1-(1,1-dimethylethylester)-1-pyrrolidinecarboxylic acid b (0.410 g, 1.07 mmol, 99%).

Example 25

2(S)-[[(2-(4'-Fluoro(1,1'-biphenyl))amino]carbonyl]-1-(1,1-dimethylethylester)-1-pyrrolidinecarboxylic acid

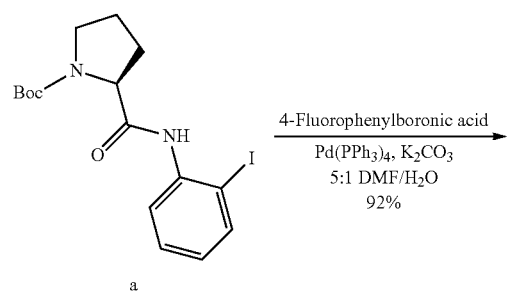

a

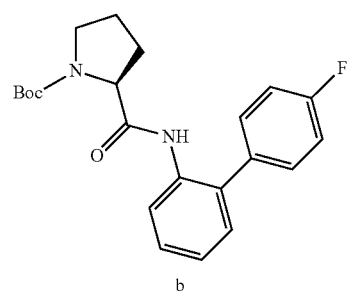

b

Following the procedure of example 19, 2(S)-[[(2-Iodophenyl)amino]carbonyl]-1-(1,1-dimethylethylester)-1-pyrrolidinecarboxylic acid a (0.4467 g, 1.07 mmol), 4-fluorophenylboronic acid (0.2230 g, 1.59 mmol), $K_2CO_3$ (0.2434 g, 1.76 mmol), and $Pd(PPh_3)_4$ (0.0686 g, 0.0594 mmol) gave the 2(S)-[[(2-(4'-fluoro(1,1'-biphenyl))amino]carbonyl]-1-(1,1-dimethylethylester)-1-pyrrolidinecarboxylic acid a (0.382 g, 0.994 mmol, 92%).

Example 26

3-Amino-4-chloro-2-phenylpyridine

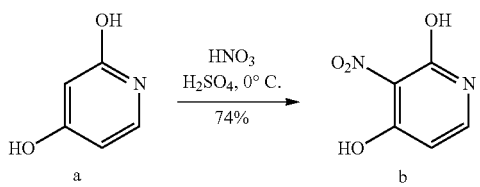

Following the general procedure of Norman (Norman, M. H., et al, *J. Med. Chem.*, 2000, 43, 4288), 2,4-dihydroxypyridine (4.931 g, 44.4 mmol) and $H_2SO_4$ (20 mL) were combined and cooled to 0° C. $HNO_3$ (20 mL, 444 mmol) was added dropwise. The sample was stirred for 30 minutes then poured onto ice. The resulting solid was stored at 4° C. for 1 hour then vacuum filtered to give 2.4-dihydroxy-3-nitropyridine (5.143 g, 32.9 mmol, 74%).

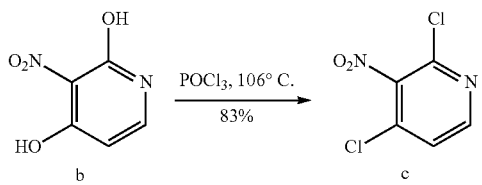

Following the general procedure of Norman (Norman, M. H., et al, *J. Med. Chem.*, 2000, 43, 4288), 2.4-dihydroxy-3-nitropyridine b (2.0013 g, 12.9 mmol) and $POCl_3$ (25 mL, 268 mmol) were combined under nitrogen. The mixture was heated to 106° C. and stirred overnight. The sample was concentrated and poured onto ice. The reaction mixture was extracted with EtOAc (3×100 mL). The EtOAc extracts were washed with saturated NaCl (1×100 mL). The EtOAc layer was dried over $MgSO_4$ and filtered. The crude material was adsorbed onto silica gel, filtered through a plug of silica gel (50% EtOAc in hexanes), and concentrated to give 2,4-dichloro-3-nitropyridine c (2.058 g, 10.7 mmol, 83%).

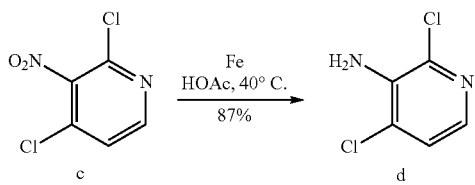

2.4-Dichloro-3-nitropyridine c (2.058 g, 10.7 mmol) was dissolved in HOAc (10 mL) under nitrogen. Iron powder (1.9191 g, 34.4 mmol) was added. The sample was heated at 40° C. for two hours. The reaction mixture was poured onto ice and then $NaHCO_3$ was added to give a neutral solution. The sample was extracted with EtOAc (3×100 mL). The EtOAc extracts were washed with saturated $NaHCO_3$ (1×100 mL). The combined aqueous layers were back extracted once with 100 mL EtOAc. The combined EtOAc extracts were dried over $MgSO_4$, filtered, and concentrated to give 3-amino-2-4-dichloropyridine d (1.510 g, 9.26 mmol, 87%).

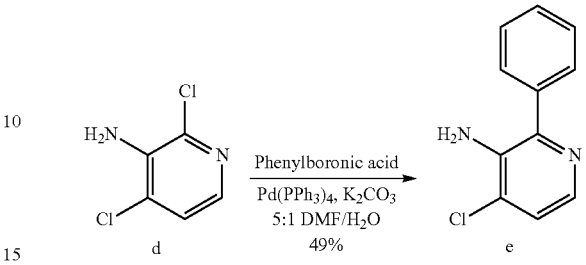

3-Amino-2-4-dichloropyridine d (0.7047 g, 4.32 mmol), phenylboronic acid (0.5177 g, 4.24 mmol), $K_2CO_3$ (0.8023 g, 5.80 mmol), and $Pd(PPh_3)_4$ (0.0702 g, 0.0607 mmol) were combined. The sample was evacuated and purged with nitrogen three times. Dry DMF (2 mL) and deoxygenated $H_2O$ (0.4 mL) were added. The sample was microwaved at 130° C. for 40 minutes. The reaction mixture was diluted with $H_2O$ (50 mL) and extracted with EtOAc (3×50 mL). The EtOAc extracts was dried over $MgSO_4$ and filtered. The crude material was adsorbed onto silica gel and purified by flash chromatography (40 g $SiO_2$, 0-30% EtOAc in hexanes) to give 3-amino-4-chloro-2-phenylpyridine e (0.435 g, 2.12 mmol, 49%).

Example 27

2(S)-[[4-phenyl-2-thiazolo[4,5-c]pyridinyl]-1-(9H-fluoren-9-ylmethyl)ester-1-pyrrolidinecarboxylic acid

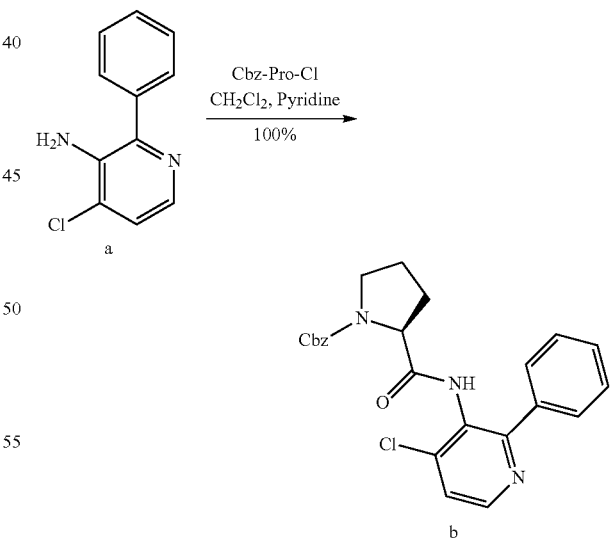

3-Amino-4-chloro-2-phenylpyridine a (0.435 g, 2.12 mmol) was dissolved in dry $CH_2Cl_2$ (10 mL). Dry pyridine (0.86 mL, 10.6 mmol) was added. Cbz-Pro-Cl (1.0804 g, 4.04 mmol), prepared according to example 14, in $CH_2Cl_2$ (5 mL) was added dropwise. The sample was stirred for one hour. The reaction mixture adsorbed onto silica gel and purified by flash chromatography (40 g $SiO_2$, 0-100% EtOAc in hexanes) to give 2(S)-[[4-chloro-2-phenyl-3-pyridinyl)amino]carbonyl]-1-(9H-fluoren-9-ylmethyl)ester-1-pyrrolidinecarboxylic acid b (0.986 g, 2.12 mmol, 100%).

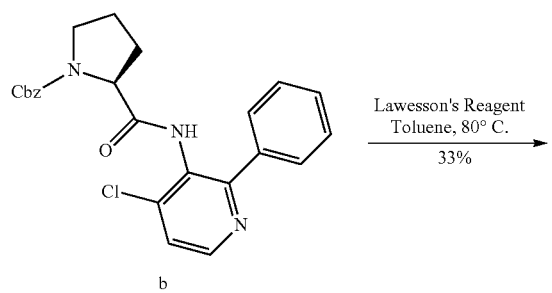

b

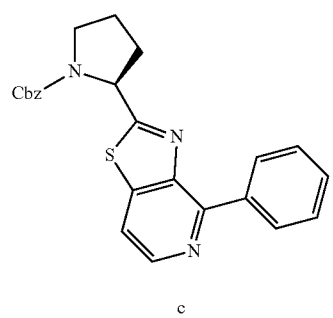

c

2(S)-[[4-Chloro-2-phenyl-3-pyridinyl)amino]carbonyl]-1-(9H-fluoren-9-ylmethyl)ester-1-pyrrolidinecarboxylic acid b (0.986 g, 2.12 mmol) was dissolved in dry toluene (20 mL). Lawesson's reagent (0.6315 g, 1.56 mmol) was added. The sample was heated to 80° C. and stirred overnight. The reaction mixture was adsorbed onto silica gel and purified by flash chromatography (40 g SiO₂, 0-100% EtOAc in hexanes) to give 2(S)-[[4-phenyl-2-thiazolo[4,5-c]pyridinyl]-1-(9H-fluoren-9-ylmethyl)ester-1-pyrrolidinecarboxylic acid c (0.294, 0.71 mmol, 33%).

Example 28

N-Boc-protected cyclic sulfonyl amino acid

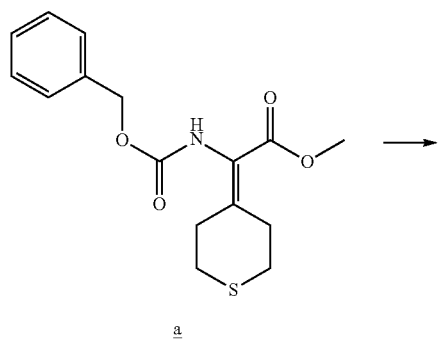

a

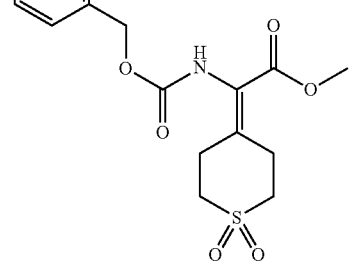

b

Sulfide a (810 mg, 2.5 mmol), synthesized according to the general procedure of Shieh [Shieh, W—C.; Xue, S.; Reel, N.; Wu, R.; Fitt, J.; Repic, O. *Tetrahedron: Asymmetry*, 2001, 12, 2421-2425], was dissolved in methanol (25 mL). Oxone (4.5 g) was dissolved in deionized water (25 mL). The methanol solution of substrate was cooled to −10° C., and the aqueous solution of oxone was added to the reaction slowly. The reaction was kept on ice and gradually allowed to warm to room temperature while stirring overnight. Deionized water was used to dilute the reaction to approximately 150 mL, then poured into 90% ethyl acetate-hexanes for extraction. The organic phase was dried ($Na_2SO_4$), adsorbed onto Celite and purified by chromatography ISCO CombiFlash 40 g column, 5-90% ethyl acetate-hexanes over 30 min to afford 804 mg (2.27 mmol, 91%) of the product sulfone b.

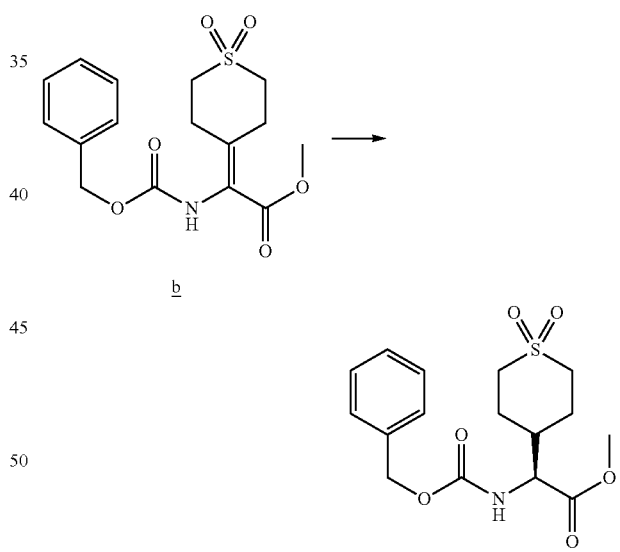

Following the general procedure of Burk [Burk, M. J.; Gross, M. F.; Martinez, J. P. *J. Am. Chem. Soc.* 1995, 117, 9375-9376.], alkene b (774 mg 2.19 mmol), dry methanol (40 mL), and [(S,S)-Me-BPE-Rh(COD)]⁺OTf⁻ (500 mg, 0.8 mmol) were mixed in a Parr shaker flask purged with nitrogen. The Parr flask was evacuated and subsequently charged to 60 psi with hydrogen gas and shaken vigorously overnight. Methanol was removed under reduced pressure, and crude product was filtered through a small plug of silica gel using ethyl acetate. Evaporation of the solvent yielded 730 mg (2.0 mmol, 94%) of product c with >98% yield.

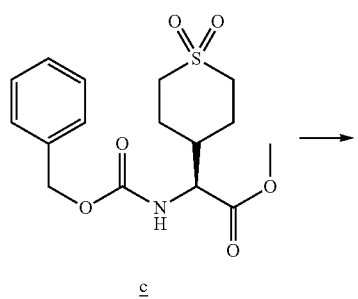

c

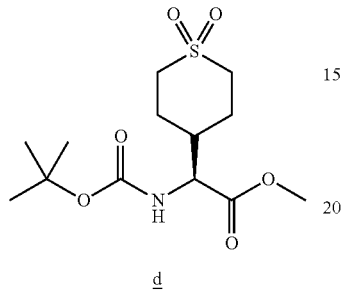

d

Z-protected amino ester c (804 mg, 2.27 mmol) was dissolved in methanol (16 mL). To this solution was added BOC-anhydride (1.5 g, 6.8 mmol), followed by 20% Pd(OH)$_2$—C (250 mg). All air was removed from the reaction flask by house vacuum, and the mixture was stirred vigorously for 5 min. The flask was then filled with hydrogen gas and allowed to stir vigorously at room temperature for 6 h. After evacuating the hydrogen atmosphere, the mixture was filtered through Celite using methanol, and crude product d was obtained by evaporation of the solvent (508 mg, 1.56 mmol, 70% yield).

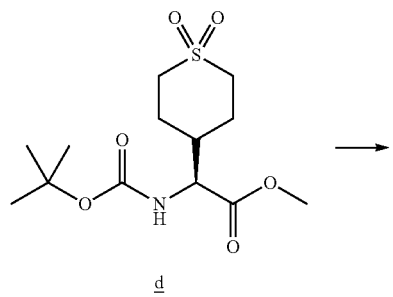

d

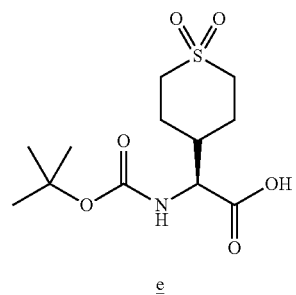

e

Ester d (508 mg, 1.56 mmol) was dissolved in 8 mL of THF. Deionized water (4 mL) was added, followed by LiOH.H$_2$O (120 mg, 2.8 mmol). The mixture was stirred at room temperature overnight, acidified using aqueous 1 N HCl and extracted into ethyl acetate (3×25 mL). The organic extracts were dried further with Na$_2$SO$_4$, filtered and concentrated to give 372 mg (1.21 mmol, 78% yield) of the N-Boc-protected cyclic sulfonyl amino acid e, which was carried on without purification.

Example 29

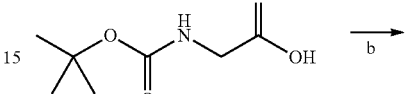

a

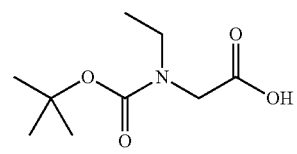

c

Following the general procedure of Grigg [Blaney, P.; Grigg, R.; Rankovic, Z.; Thornton-Pett, M.; Xu, J. *Tetrahedron*, 2002, 58, 1719-1737] a roundbottom flask was charged with sodium hydride (480 mg 60% dispersion in oil, 12.0 mmol, 4.0 equiv) and purged with nitrogen for 15 min. THF (6.0 mL) was added to the flask, and the suspension was cooled to 0° C. using an ice water bath. A separate flask was charged with BOC-glycine a (525 mg, 3.0 mmol), dry THF (6.0 mL) and ethyl iodide (1.0 mL, 12 mmol, 4 equiv). This mixture was added dropwise to the NaH suspension in THF, with vigorous stirring at 0° C. After 1 h of stirring, the reaction was warmed to room temperature and allowed to stir overnight. The reaction was again cooled to 0° C., and methanol (4 mL) was added very slowly to quench the excess hydride. Deionized water was added to dilute the mixture, and methanol was removed under reduced pressure. Impurities were extracted into 90% ethyl acetate-hexanes, the aqueous layer was then acidified by adding solid citric acid until the pH reached 2-3. The product was extracted into 90% ethyl acetate-hexanes. This organic layer was dried (Na$_2$SO$_4$) and filtered. Removal of the solvents under reduced pressure afforded a quantitative yield of the product b.

Example 30

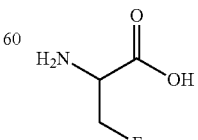

a

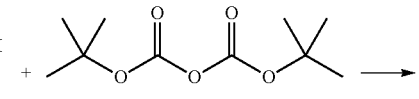

b

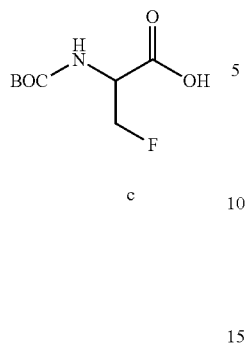

A mixture of unprotected amino acid a (775 mg, 7.24 mmol) and sodium carbonate (1.69 g, 16.0 mmol) was dissolved in a 1:1 solution of deionized water and THF (15 mL each). To this mixture was added BOC-anhydride b (1.73 g, 7.96 mmol). The mixture was stirred at room temperature overnight, and THF was removed under reduced pressure. The mixture was then acidified to pH 2-3 with saturated aqueous citric acid, and product was extracted into 10% ethyl acetate-dichloromethane. The organic layer was dried (Na$_2$SO$_4$), filtered and concentrated under reduced pressure to afford clean BOC-protected amino acid c (1.40 g, 6.7 mmol, 93%) to be used without further purification.

Example 31

Dimer Compound 1

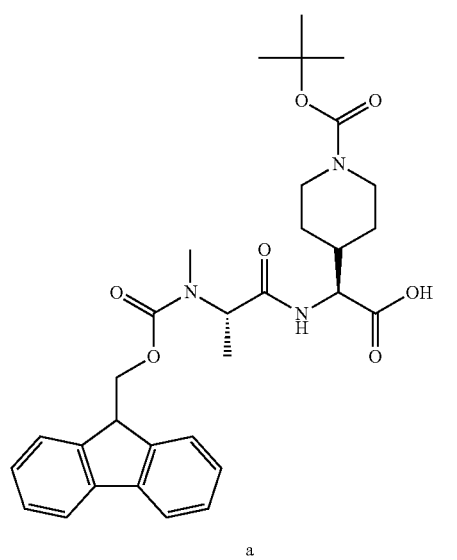

+

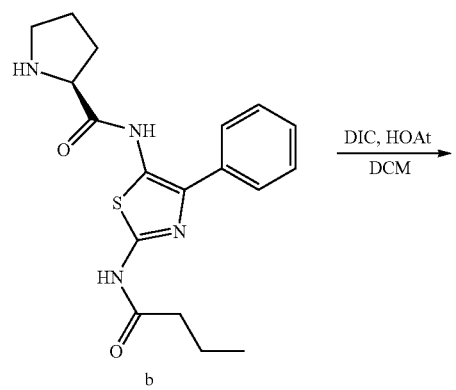

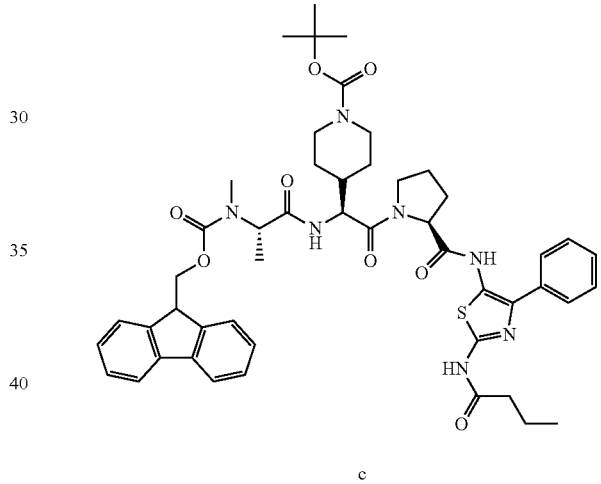

In a 25 mL round-bottomed flask, dipeptide a (1.2 g, 2.1 mmol) and compound b (500 mg, 1.2 mmol) were dissolved in dichloromethane (5.0 mL). N,N-diisopropylcarbodiimide (0.35 mL, 2.2 mmol) and 1-hydroxy-7-azabenzotriazole (300 mg, 2.2 mmol) were added and the mixture was stirred at room temperature overnight. The mixture was then concentrated on silica gel and purified by flash chromatography (100% Hex to 100% EtOAc, 40 g column) to afford 1.1 g (87%) of compound c as a white solid. MS: M/Z=907.

123
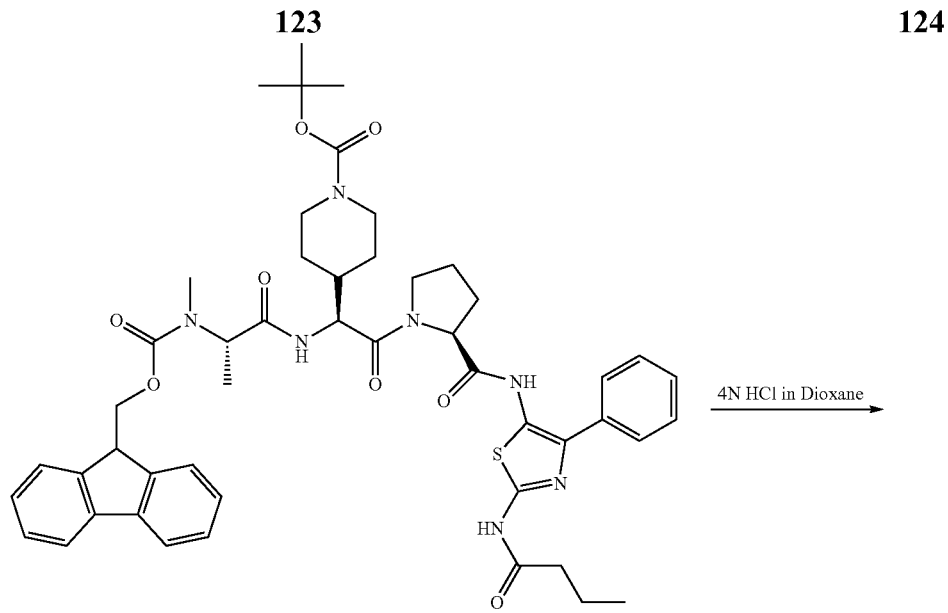
c
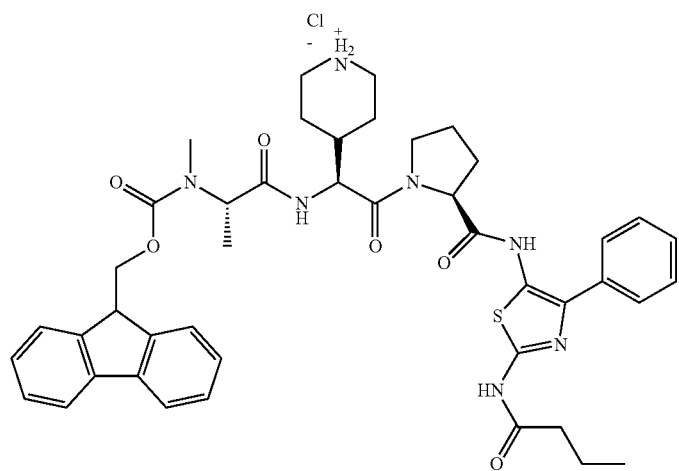
d
In a 50 mL round-bottomed flask, compound c (1.1 g, 1.2 mmol) was dissolved in a solution of 4N HCl in dioxane (20 mL, 60 mmol) and the solution was stirred at room temperature for 30 minutes. The solution was then concentrated to afford 1.0 g (99%) of compound d as a pale yellow solid. MS: M/Z=807.
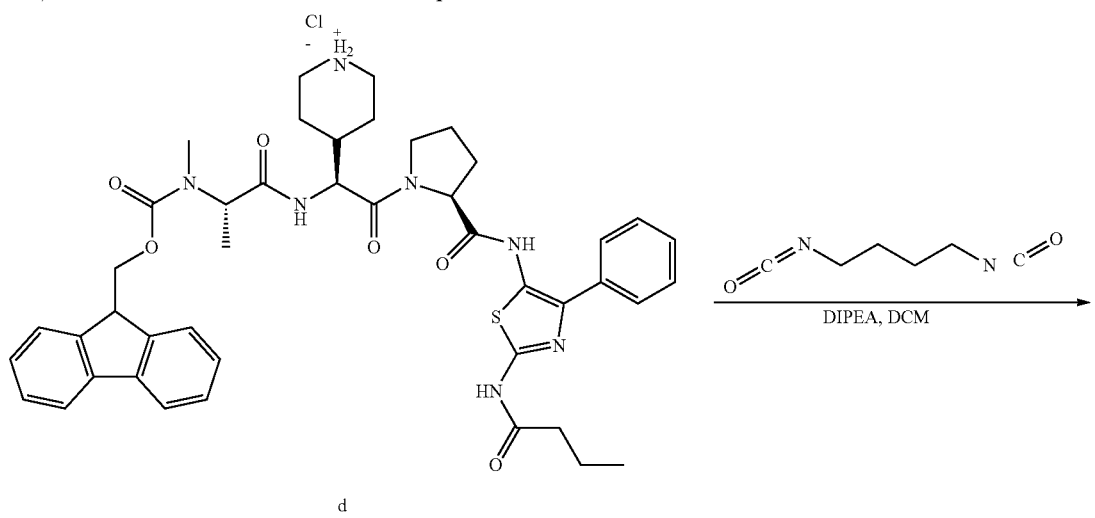
d -continued

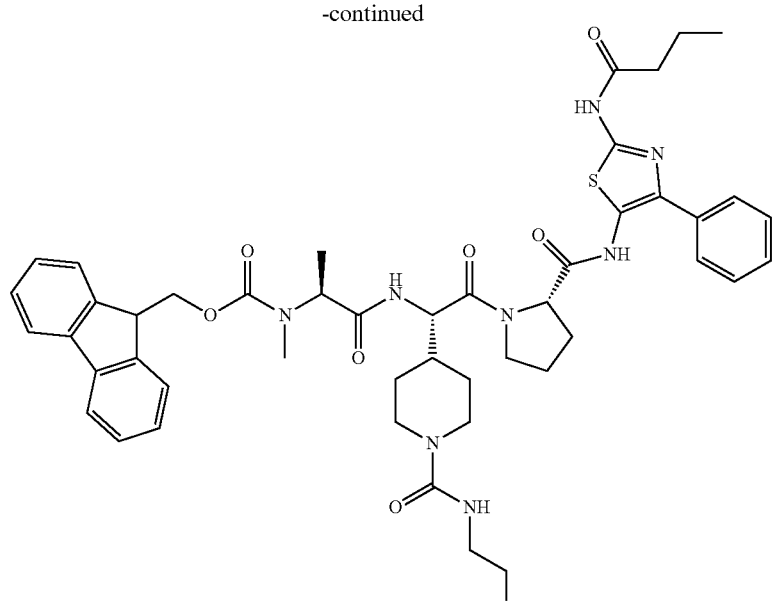

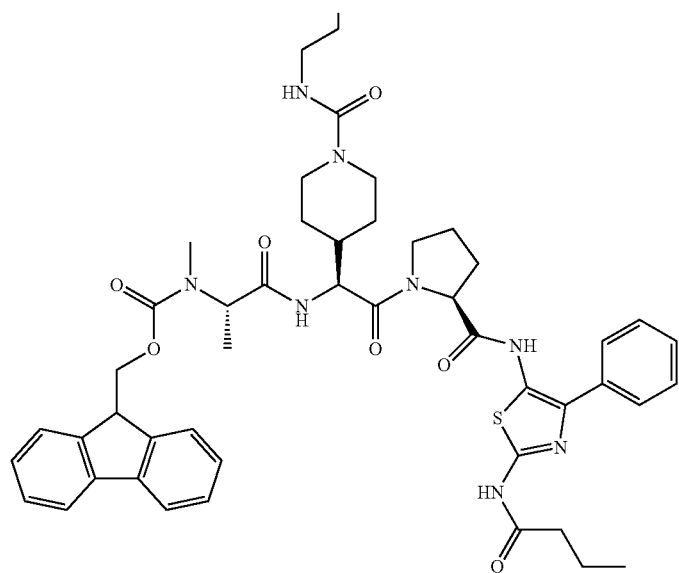

e

In a 10 mL round-bottomed flask, 1,4-diisocyanatobutane (9.0 µL, 0.071 mmol), dissolved in dichloromethane (0.5 mL), was slowly added to a solution of compound d (120 mg, 0.14 mmol) and N,N-diisopropylethylamine (37 µL, 0.21 mmol) in dichloromethane (0.5 mL) and the mixture was stirred at room temperature for 6 h. The mixture was then concentrated on silica gel and purified by flash chromatography (100% DCM to 5% MeOH/DCM, 12 g column) to afford 81 mg (65%) of compound e as a white solid. MS: M/Z=1753.

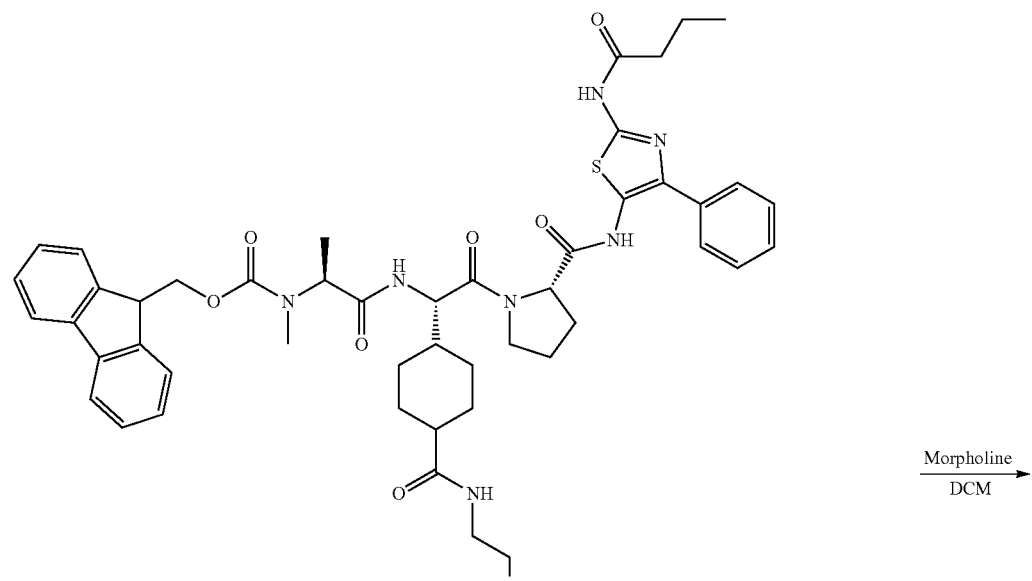
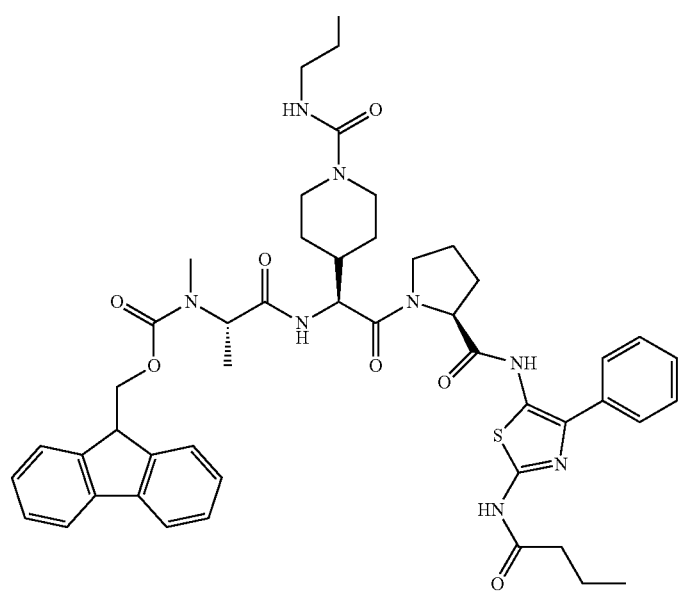

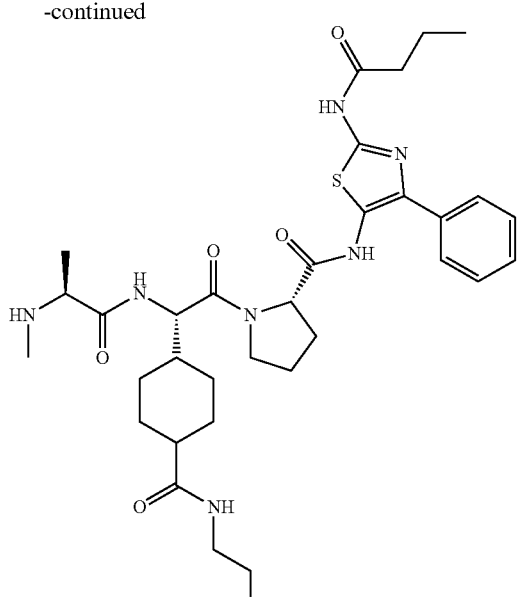
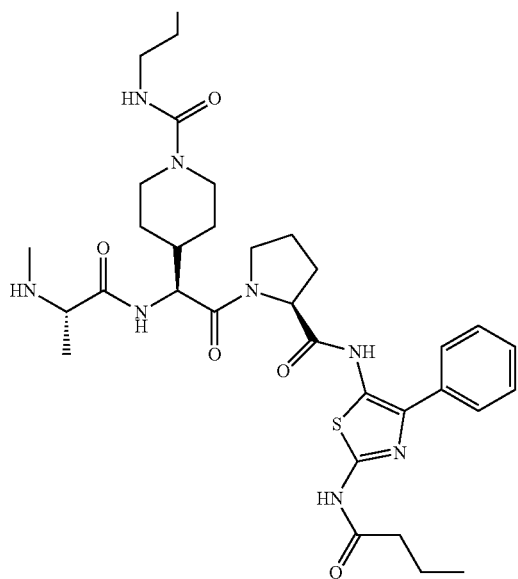
1
In a 25 mL round-bottomed flask, compound e (81 mg, 0.046 mmol) was dissolved in dichloromethane (5.0 mL) and morpholine (0.40 mL, 4.6 mmol) was added. The solution was stirred at room temperature overnight. The solution was then concentrated and purified by reverse phase HPLC to afford 22.6 mg (37%) of compound 1 as a white solid. MS: M/Z=1308.

Example 32

Dimer Compound 2

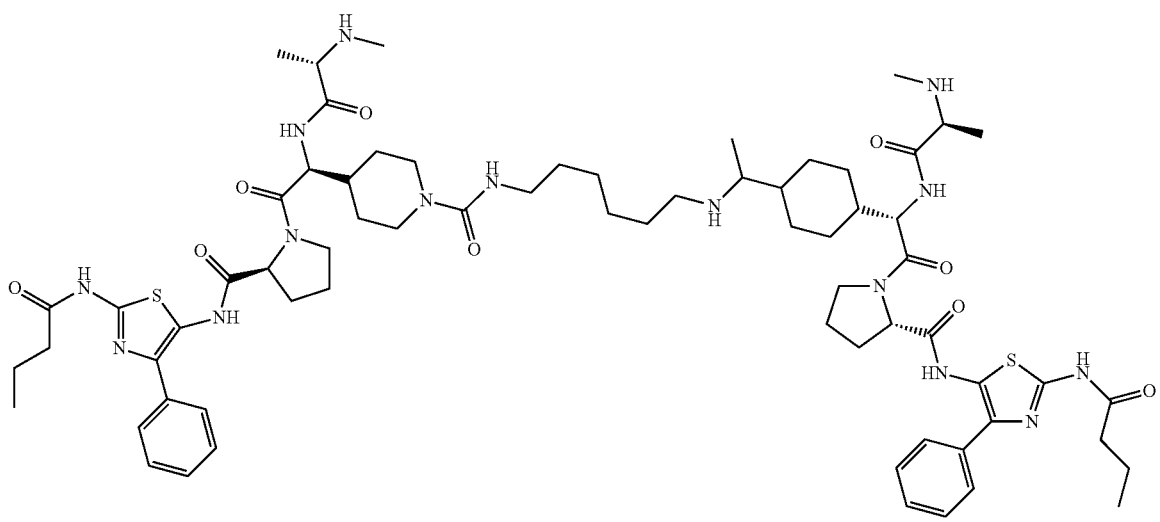

Compound 2 was prepared using the procedure for compound 1, (12.6 mg of a white solid). MS: M/Z=1336.

Example 33

Dimer Compound 3

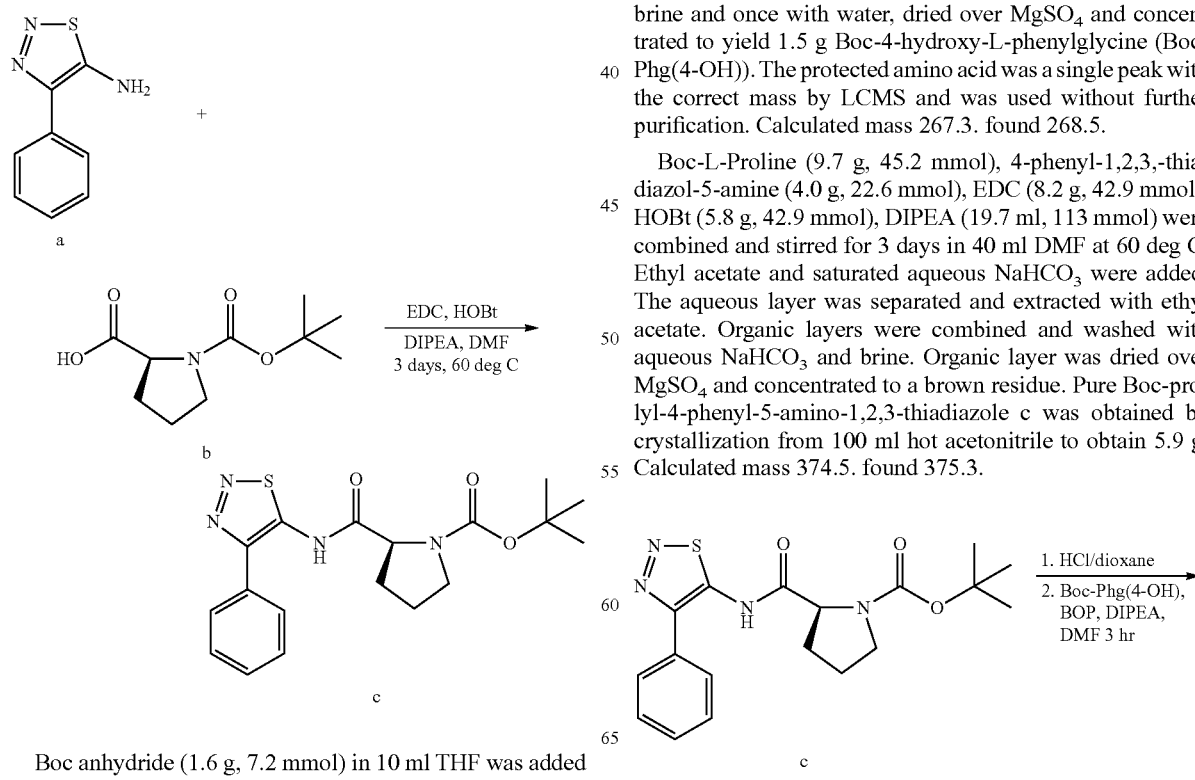

Boc anhydride (1.6 g, 7.2 mmol) in 10 ml THF was added dropwise to an ice-cooled stirring solution of 4-hydroxy-L-phenylglycine (1.0 g, 6 mmol) and NaHCO$_3$ (1.0 g, 12 mmol) in 10 ml water. After complete addition, solution was warmed to room temp and stirred overnight. THF was evaporated off and 10 ml water was added. The aqueous layer was extracted twice with 20 ml ethyl acetate and the aqueous layer was acidified to pH 3 with aqueous citric acid. The aqueous layer was extracted twice with 25 ml ethyl acetate and organic layers combined. The organic layer was washed twice with brine and once with water, dried over MgSO$_4$ and concentrated to yield 1.5 g Boc-4-hydroxy-L-phenylglycine (Boc-Phg(4-OH)). The protected amino acid was a single peak with the correct mass by LCMS and was used without further purification. Calculated mass 267.3. found 268.5.

Boc-L-Proline (9.7 g, 45.2 mmol), 4-phenyl-1,2,3,-thiadiazol-5-amine (4.0 g, 22.6 mmol), EDC (8.2 g, 42.9 mmol), HOBt (5.8 g, 42.9 mmol), DIPEA (19.7 ml, 113 mmol) were combined and stirred for 3 days in 40 ml DMF at 60 deg C. Ethyl acetate and saturated aqueous NaHCO$_3$ were added. The aqueous layer was separated and extracted with ethyl acetate. Organic layers were combined and washed with aqueous NaHCO$_3$ and brine. Organic layer was dried over MgSO$_4$ and concentrated to a brown residue. Pure Boc-prolyl-4-phenyl-5-amino-1,2,3-thiadiazole c was obtained by crystallization from 100 ml hot acetonitrile to obtain 5.9 g. Calculated mass 374.5. found 375.3.

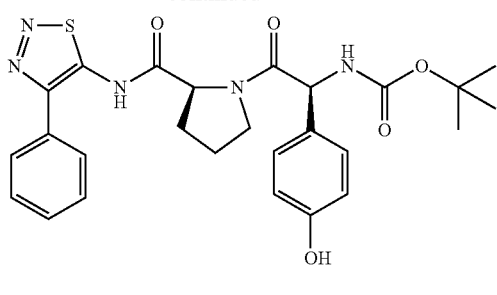

d

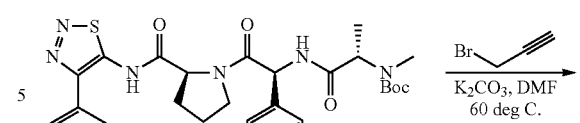

e

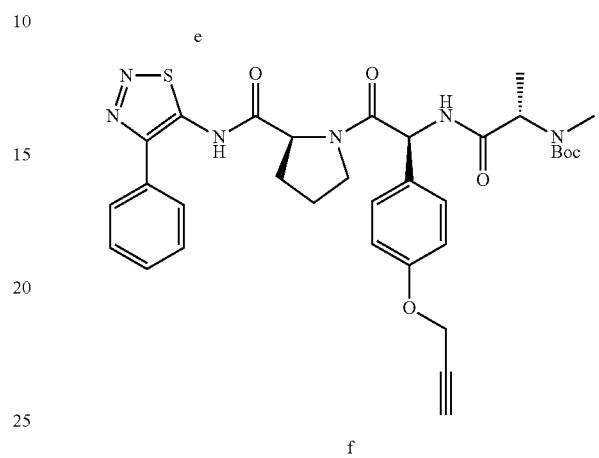

f

Compound c (1.5 g, 4.25 mmol) was treated with 20 ml 4N HCl/dioxane for 30 minutes and the solvent was removed. Boc-L-Phg(4-OH) (1.25 g, 4.68 mmol), BOP (2.1 g, 4.68 mmol), DIPEA (1.63 ml, 9.36 mmol) were combined in 30 ml DMF and stirred for 3 hours at room temp. to give compound d. Standard workup: Ethyl acetate was added and organic layer washed twice with aqueous sodium bicarbonate, washed twice with brine, dried over MgSO₄ and concentrated. The residue was a single peak with the correct mass by LCMS and was used in the next step without purification. Calculated mass 523.6. found 524.3.

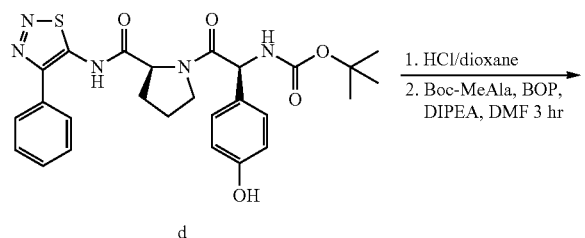

d

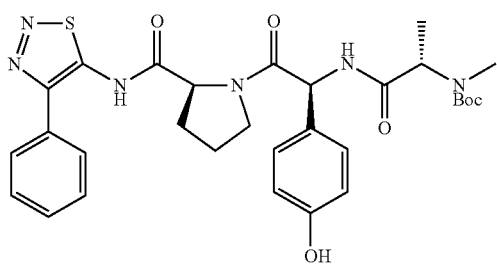

e

Compound d from the previous step was treated with 20 ml 4N HCl/dioxane for 30 minutes and the solvent removed. Boc-N-methylalanine (0.95 g, 4.68 mmol), BOP (2.1 g, 4.68 mmol) and DIPEA (1.63 ml, 9.36 mmol) were combined in 30 ml DMF and stirred for 3 hours at room temp. Standard workup: Ethyl acetate was added and organic layer washed twice with aqueous sodium bicarbonate, washed twice with brine, dried over MgSO₄ and concentrated. The residue was purified by HPLC to yield 1.2 g of compound e. Calculated mass 608.7. found 609.3.

Compound e (1.2 g, 1.97 mmol), 80 weight % propargyl bromide in toluene (879 mg, 5.91 mmol), K₂CO₃ (817 mg, 5.91 mmol) were combined in 40 ml DMF and stirred for 16 hours at 60 deg C. Water was added to solution and extracted 3 times with ethyl acetate. Organic layers were combined, washed twice with aqueous NaHCO₃, washed twice with brine, dried over MgSO₄ and concentrated. Crude residue purified by HPLC to yield 200 mg of compound f. Calculated mass 646.8. found 647.3.

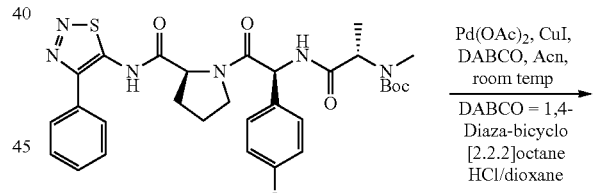

f

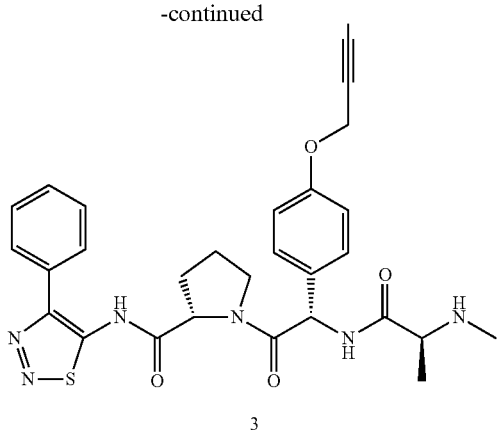

3

b

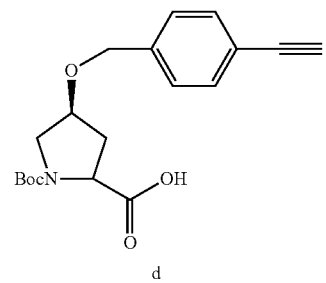

Compound f (200 mg, 0.31 mmol), Pd(OAc)$_2$ (1.2 mg, 0.0062 mmol), CuI (1.4 mg, 0.0062 mmol) and DABCO (104 mg, 0.93 mmol) were combined in 20 ml acetonitrile and stirred overnight at room temp. Ethyl acetate was added and the organic layer was washed twice with aqueous NaHCO$_3$, washed twice with brine, dried over MgSO$_4$ and concentrated. The residue was treated with 20 ml 4N HCl/dioxane for 30 minutes and concentrated. The crude residue was purified by HPLC to obtain 81 mg of compound 3. Calculated mass 1091.3. found 1091.7.

Example 34

Dimer Compound 4

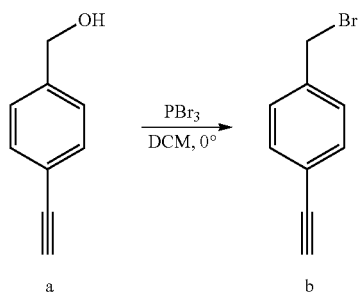

4-Ethynylbenzyl alcohol a (1 g, 7.57 mmol) was diluted in 20 ml DCM, and cooled to 0° in ice bath. Phosphorus tribromide (4.1 g, 15 mmol) was added dropwise. The reaction was allowed to warm to room temperature gradually, and stirred under nitrogen overnight. The reaction was quenched by addition of H$_2$O in ice bath, extracted by DCM. Combined organic layers were washed with brine, dried over Na$_2$SO$_4$ and concentrated to dryness. The crude material was purified by chromatography (ISCO) using 100% hexane to give pure 4-ethynylbenzyl bromide b (220 mg). M+H$^+$ 195.1

NaH (135 mg, 3.4 mmol, 60% dispersion in mineral oil) was suspended in an ice-cooled anhydrous THF solution (5 ml) under nitrogen. N-boc-cis-4-hydroxy-L-proline methyl ester c (417 mg, 1.7 mmol) was added followed by 4-ethynylbenzyl bromide b (220 mg, 1.13 mmol). The reaction was allowed to warm to room temperature gradually, and stirred under nitrogen overnight. The reaction was quenched by addition of H$_2$O in ice bath, and concentrated to dry. The crude material was purified by chromatography (ISCO) using 10% MeOH/DCM to obtain 200 mg compound d. M+H$^+$ 346.2

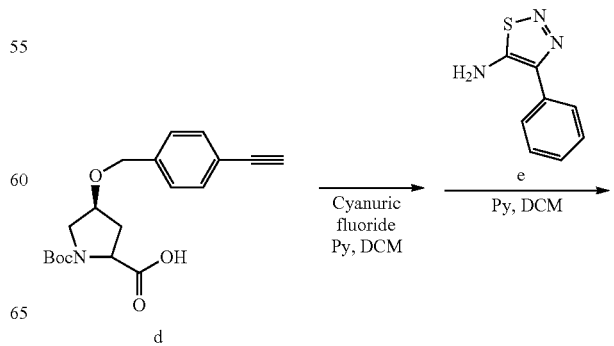

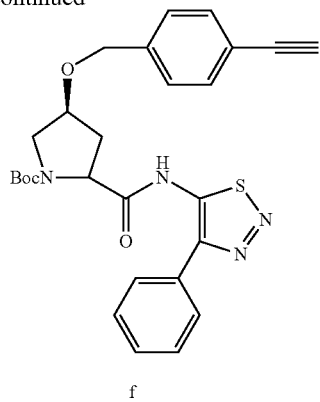

f

The compound d (200 mg, 0.578 mmol) was diluted in DCM (10 ml), cooled in an ice bath, treated with pyridine (137 mg, 1.73 mmol) and cyanuric fluoride (109 mg, 0.81 mmol) dropwise. After complete addition, solution was warmed to room temperature and stirring for 4 hours. 1 ml of H$_2$O was added, solution was stirred for 15 minutes. Additional H$_2$O (20 ml) was added, and aqueous layer was extracted by DCM twice. Combined organic layers were washed with sat. brine, dried over Na$_2$SO$_4$, and concentrated to dry. The residue was used in the next step without further purification. The crude oil (205 mg, 0.578 mmol), 4-phenyl-1,2,3-thiadiazol-5-amine e (207 mg, 1.16 mmol) and pyridine (136 mg, 1.76 mmol) were combined in 10 ml DCM and stirred overnight. Additional DCM was added, and washed with aq. NaHCO$_3$. Aqueous layer was extracted by DCM twice, washed with sat. brine, dried over Na$_2$SO$_4$ and concentrated to dry. The crude material was purified by chromatography (ISCO) using 40%-80% EtOAc/Hexane to obtain 101 mg compound f. M+H$^+$ 505.4

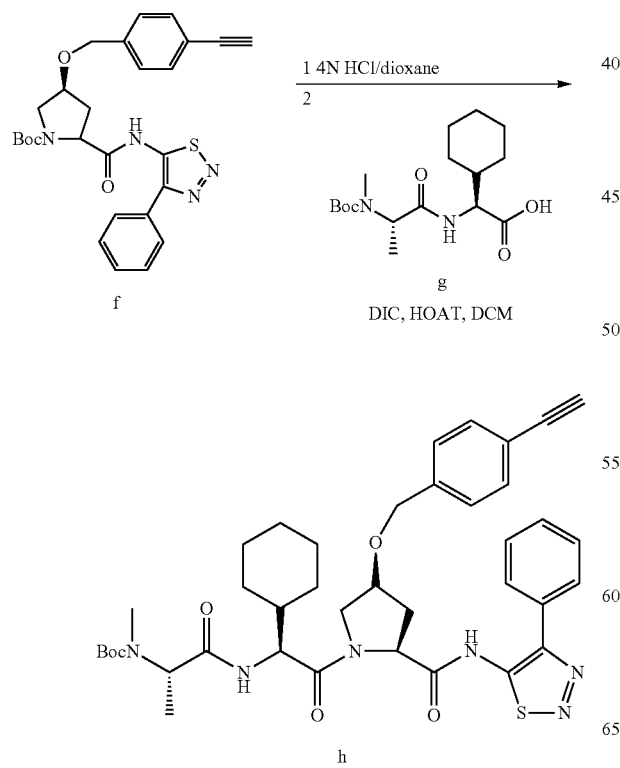

The compound f (40 mg, 0.079 mmol) was treated with 10 ml 4N HCl/dioxane for 30 minutes and solvent was removed. The residue, Boc-N-Meala-Chg-OH g, DIC and HOAt were combined in 5 ml of dry DCM and stirred for 4 hours at room temperature. H$_2$O was added to solution and extracted twice with DCM. Organic layers were combined, dried over Na$_2$SO$_4$, and concentrated. The crude material was purified by chromatography (ISCO) using 40%-80% EtOAc/Hexane to obtain 48 mg pure compound h. M+H$^+$ 729.5

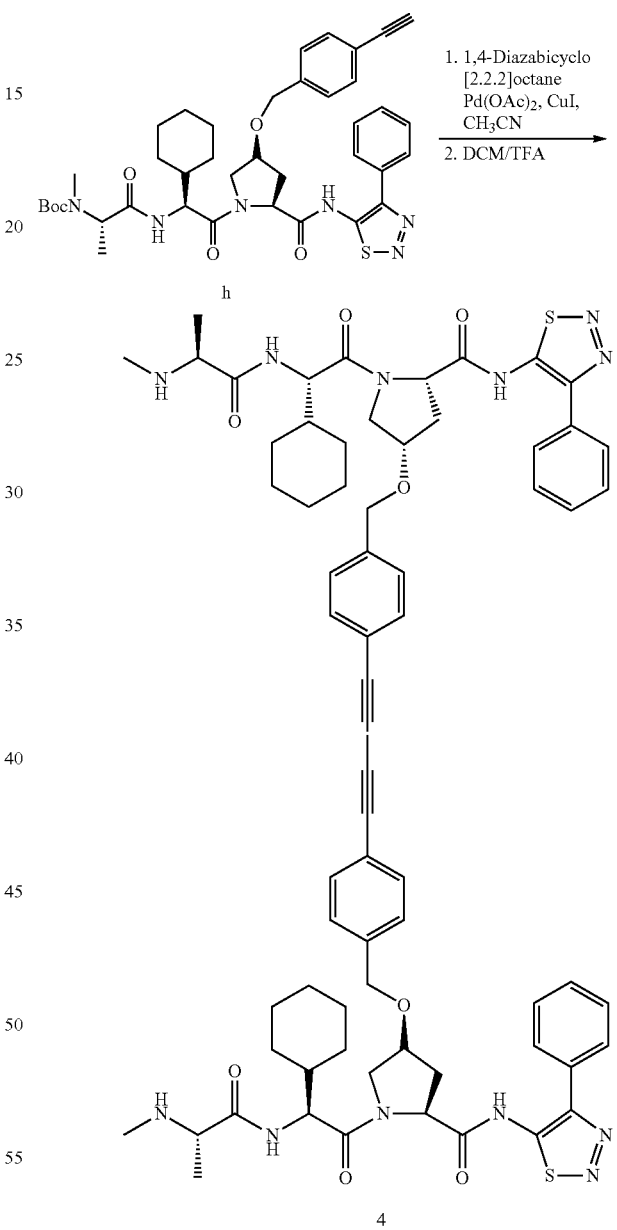

The compound h (20 mg, 0.027 mmol), Pd(OAc)$_2$ (0.121 mg, 0.00054 mmol), DABCO (9 mg, 0.082 mmol) and CuI (0.105 mg, 0.00054 mmol) were combined in 5 ml of acetonitrile and stirred overnight at room temperature. Ethyl acetate was added and the organic layer was washed twice with aq. NaHCO$_3$, the combined organic layers were washed with brine, dried over Na$_2$SO$_4$ and concentrated. The residue was treated with 1:1 DCM and TFA (20 ml) for 30 minutes and concentrated. The crude material was purified by HPLC to obtain 7 mg of compound 4. M+H$^+$1255.6

Example 35

Dimer Compound 5

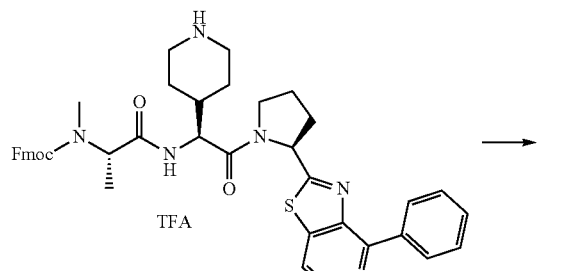

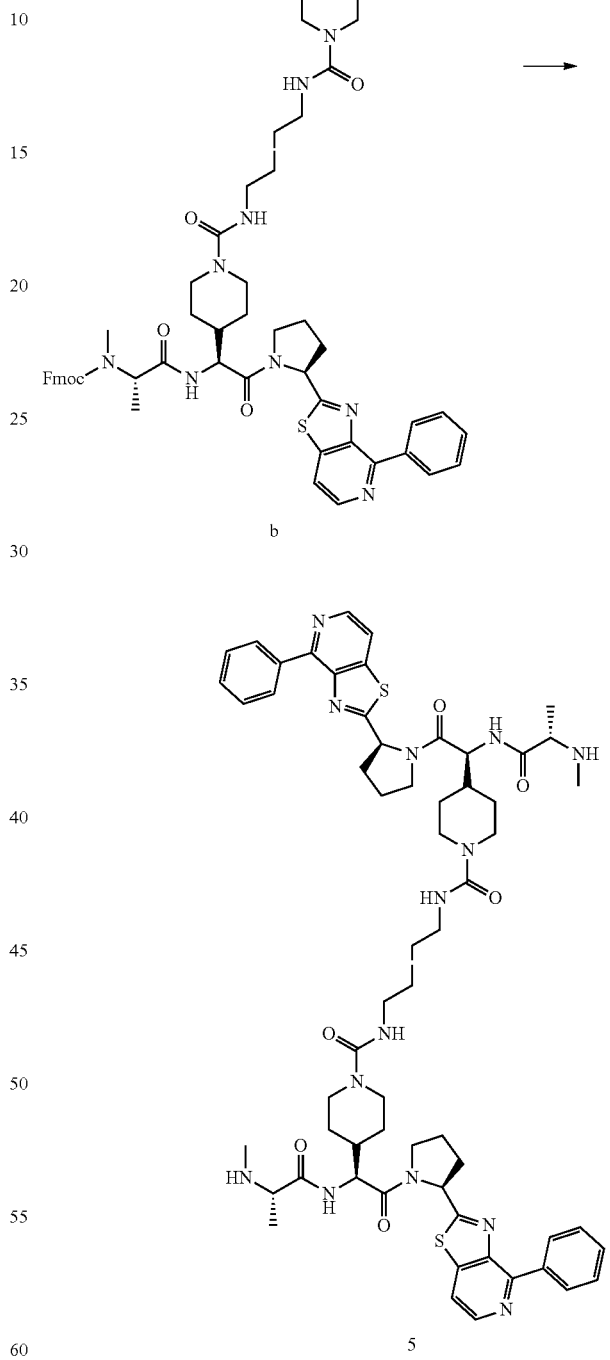

To a solution of a (0.1 g, 0.12 mmol) in dichloromethane (2 mL) was added diisopropylamine (0.0456 mL, 0.26 mmol). Adipoyl chloride (0.00862 mL, 0.06 mmol) was added to the mixture. The resulting solution was stirred at room temperature for 4 hours. Diisopropylamine (0.0456 mL, 0.26 mmol) was added to the mixture again. The solution was stirred overnight. The crude material was adsorbed onto silica gel and purified by flash chromatography (4 g SiO$_2$, 0-5% methanol in dichloromethane) to give the Fmoc protected dimer b (0.073 g, 0.046 mmol, 78%).

To a solution of Fmoc protected dimer b (0.073 g, 0.046 mmol) in dichloromethane (5 mL) was added morpholine (0.21 mL, 2.4 mmol). The mixture was stirred 3 hours. Morpholine (0.21 mL, 2.4 mmol) was added to the solution again. The solution was stirred overnight. The sample was concentrated and purified by SFC (ethyl-pyridine, 20-60% methanol in $CO_2$ in 6.5 min at 50 mL/min) to give dimer 5 (0.019 g, 0.017 mmol, 36%).

Example 36

Dimer Compound 6 room temperature for 4 hours. A small crystal of N,N-dimethylaminopyridine was added. The mixture was stirred for 30 minutes. Diisopropylamine (0.0338 mL, 0.13 mmol) was added to the mixture again. The mixture was stirred for 30 minutes. 1,6-Diisocyanatohexane (0.00478 mL, 0.0297 mmol) was added. The solution was stirred overnight. The crude material was adsorbed onto silica gel and purified by flash chromatography (4 g $SiO_2$, 0-5% methanol in dichloromethane) to give the Fmoc protected dimer b in quantitative yield.

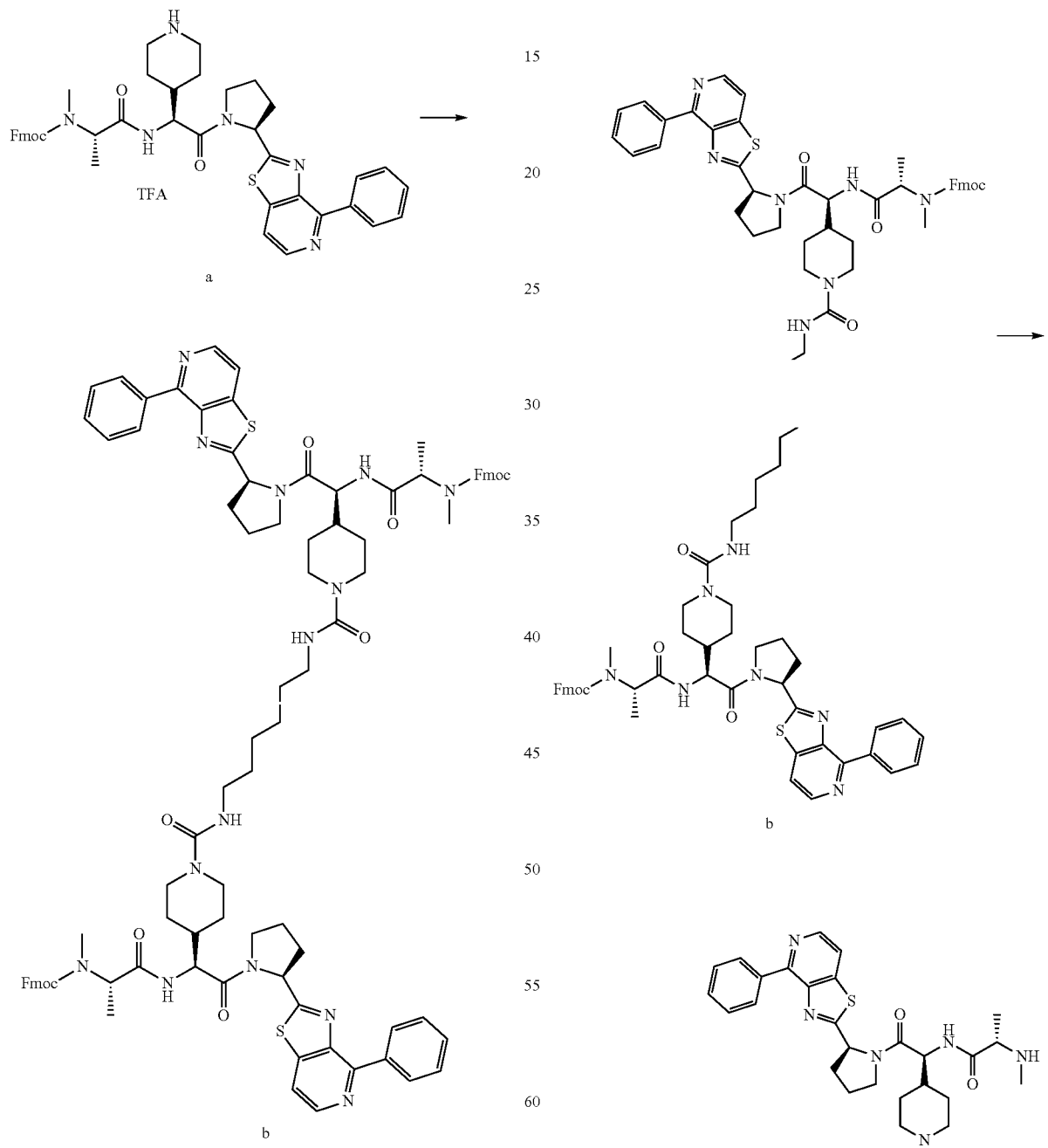

To a solution of a (0.1 g, 0.12 mmol) in dichloromethane (2 mL) was added diisopropylamine (0.0228 mL, 0.13 mmol). 1,6-Diisocyanatohexane (0.00954 mL, 0.0593 mmol) was added to the mixture. The resulting solution was stirred at

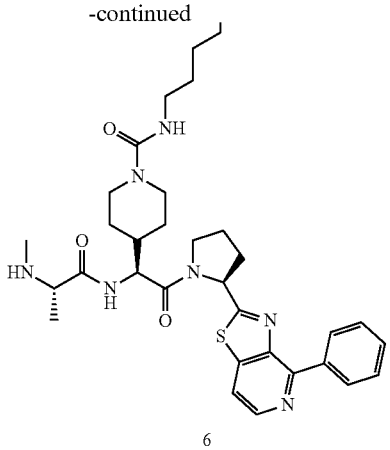

6

To a solution of Fmoc protected dimer b (0.12 mmol) in dichloromethane (5 mL) was added morpholine (0.38 mL, 4.3 mmol). The mixture was stirred 3 hours. Morpholine (0.38 mL, 4.3 mmol) was added to the solution again. The solution was stirred overnight. The sample was concentrated and purified by SFC (ethyl-pyridine, 20-60% methanol in $CO_2$ in 6.5 min at 50 mL/min) to give dimer 6 (0.0392 g, 0.033 mmol, 28%).

Example 37

Dimer Compound 7

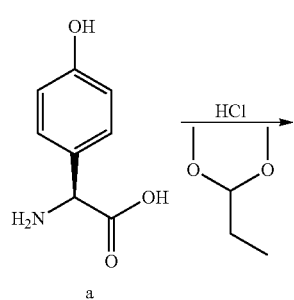

a

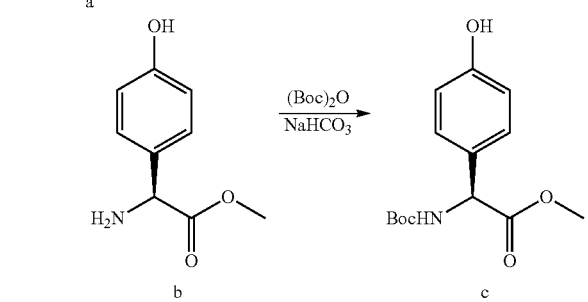

4-Hydroxyphenylglycine a (1.0 g, 5.98 mmol) and concentrated HCl (6 ml) in 2,2-dimethoxypropane (33 ml, 813 mmol) was stirred overnight at room temp. The brown solution was evaporated and the pure compound b was precipitated from a solution of methanol and ethyl ether. 1.3 g obtained. Calculated mass 181.2. found mass 181.9. Compound b (1.3 g, 5.98 mmol) and $NaHCO_3$ (1.0 g, 12.0 mmol) was dissolved in 15 ml water and 15 ml acetonitrile and Boc-anhydride (1.6 g, 7.2 mmol) in 10 ml THF was added dropwise and solution was stirred overnight at room temp. The solution was evaporated and ethyl acetate was added. The standard workup was done: the organic solution was washed with aqueous $NaHCO_3$, brine, water, dried over $MgSO_4$ and concentrated to compound c. Calculated mass 281.2. found mass 282.1.

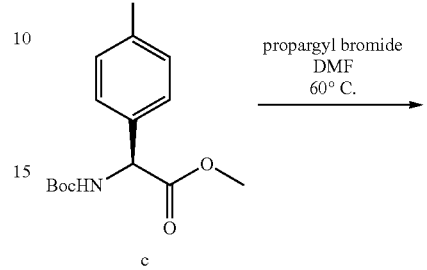

c

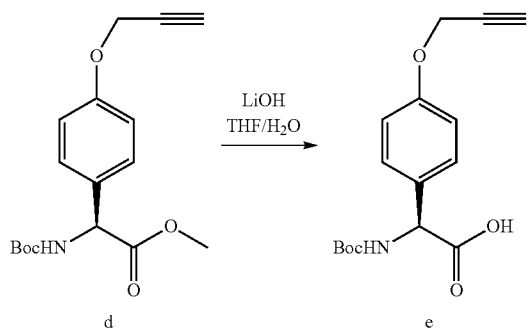

Compound c (1.63 g, 5.8 mmol), 80 weight % propargyl bromide in toluene (1.93 ml, 17.4 mmol), $K_2CO_3$ (2.4 g, 17.4 mmol) were dissolved in 30 ml DMF and heated at 50 degrees overnight. The solution was evaporated and the standard workup procedure was done as described above. The pure compound d was purified by HPLC. Calculated mass 319.4. found mass 320.1. Compound d (1.85 g, 5.8 mmol) was dissolved in 50 ml THF/water (1:1) with LiOH (487 mg, 11.6 mmol) and stirred for 4 hrs. The solution was evaporated and acidified with aqueous citric acid. The solution was extracted into EtOAc, washed with brine, dried over $MgSO_4$ and concentrated to a yellow oil of compound e. Yield 770 mg. Calculated mass 305.3. found mass 305.8.

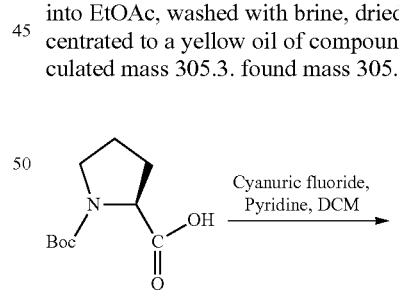

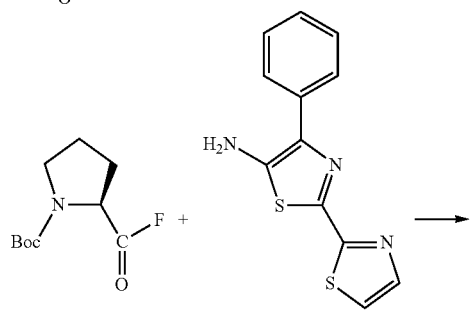

-continued

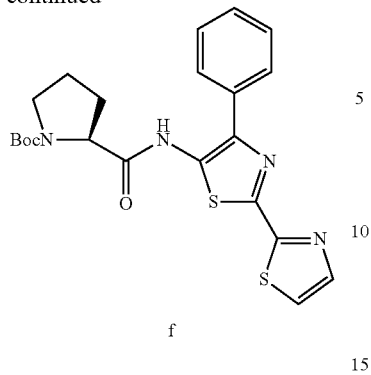

f

To an ice-cooled solution of Boc-Proline (598 mg, 2.78 mmol) and pyridine (411 ul, 5.09 mmol) in 10 ml DCM, cyanuric fluoride (406 mg, 3.01 mmol) was added dropwise. The solution allowed to warm to room temperature and stirred for 90 min. The solution was evaporated and EtOAc was added and the organic layer was washed with brine, dried over MgSO₄ and concentrated. 4-phenyl-2,2'-Bithiazol-5-amine (600 mg, 2.31 mmol) with pyridine was added to the residue and stirred overnight at room temp. The solution was evaporated, EtOAc added and the standard workup was done. Compound f was purified by HPLC. Yield 270 mg. Calculated mass 456.6. found mass 457.3.

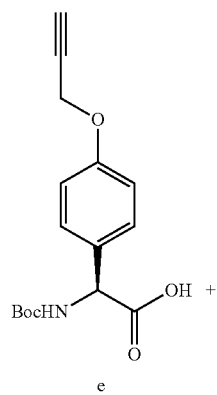

e

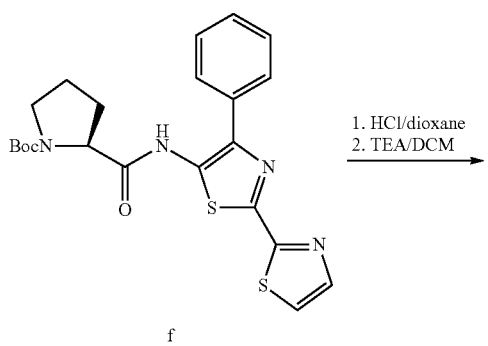

f

1. HCl/dioxane
2. TEA/DCM
→

-continued

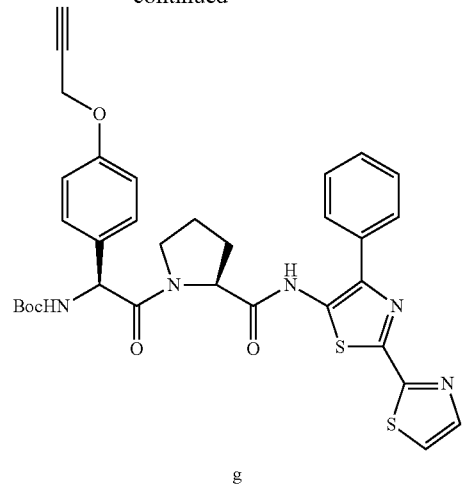

g

Compound f (200 mg, 0.44 mmol) was treated with 20 ml 4N HCl in dioxane for 30 min and the solvent removed. Boc-Phg(4-O-propargyl)-OH e (147 mg, 0.48 mmol), benzotriazol-1-yloxytris(dimethylamino)phosphonium hexafluorophosphate (BOP) (213 mg, 0.48 mmol) and DIPEA (168 ul, 0.96 mmol) were combined in 20 ml DMF and stirred for 3 hrs at room temp. Standard workup was done and purification by HPLC was done to obtain compound g. Calculated mass 643.8. found mass 644.3.

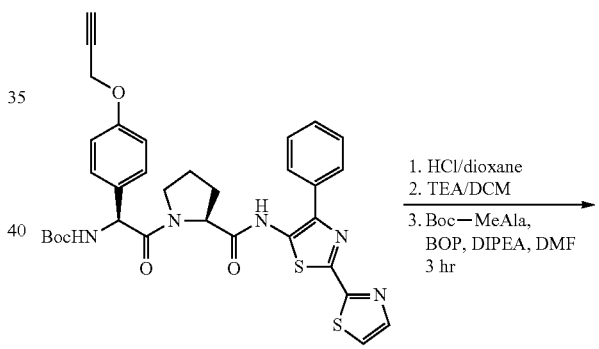

1. HCl/dioxane
2. TEA/DCM
3. Boc—MeAla, BOP, DIPEA, DMF 3 hr
→

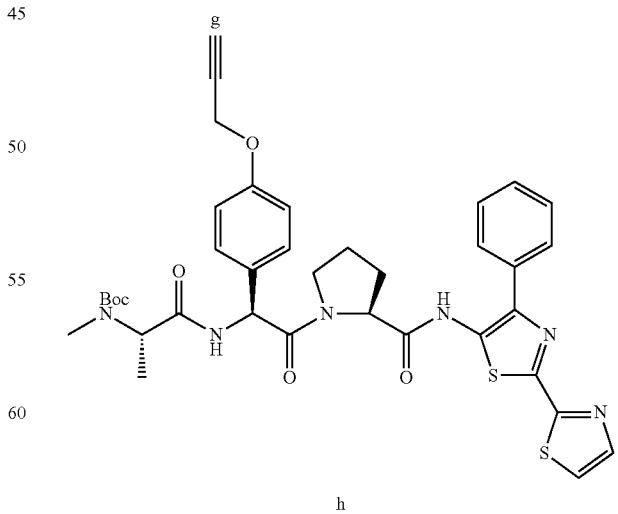

h

Compound g (282 mg, 0.44 mmol) was treated with 20 ml 4N HCl in dioxane for 30 min and the solvent removed.

Boc-MeAla (98 mg, 0.48 mmol), BOP (213 mg, 0.48 mmol) and DIPEA (168 ul, 0.66 mmol) were combined in 20 ml DMF and stirred for 3 hrs at room temp. Standard workup was done and purification by HPLC was done to obtain compound h. Yield 47 mg. Calculated mass 728.9. found mass 729.3.

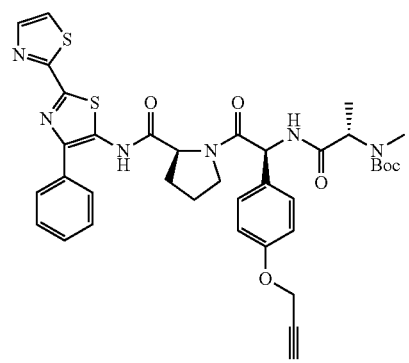

h

+

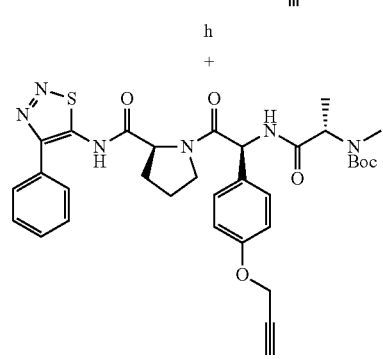

i

1. Pd(OAc)$_2$, CuI Acetonitrile, 24 h, R.T.
2. 4N HCl/Dioxane, 30 min

→

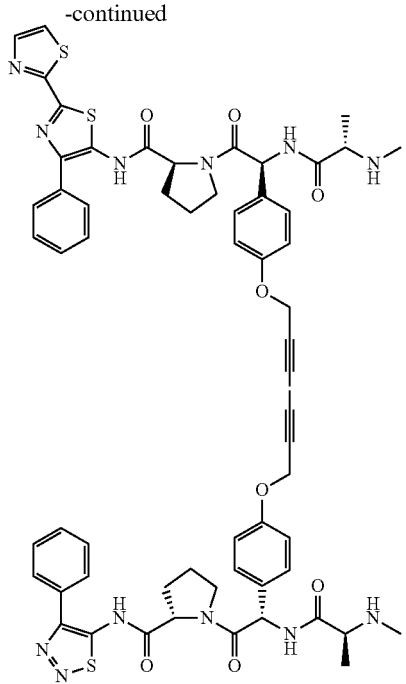

Compound g (94 mg, 0.128 mmol), compound i (84 mg, 0.128 mmol), Pd(OAc)$_2$ (1.1 mg, 0.0051 mmol), CuI (0.98 mg, 0.0051 mmol) and DABCO (86 mg, 0.77 mmol) were combined in 20 ml acetonitrile and stirred overnight at room temp. Ethyl acetate was added and the organic layer was washed twice with aqueous NaHCO$_3$, washed twice with brine, dried over MgSO$_4$ and concentrated. The residue was treated with 20 ml 4N HCl/dioxane for 30 minutes and concentrated. The crude residue was purified by HPLC to obtain 12 mg of compound 7. Calculated mass 1173.4. found 1173.8.

Example 38

Dimer Compound 8

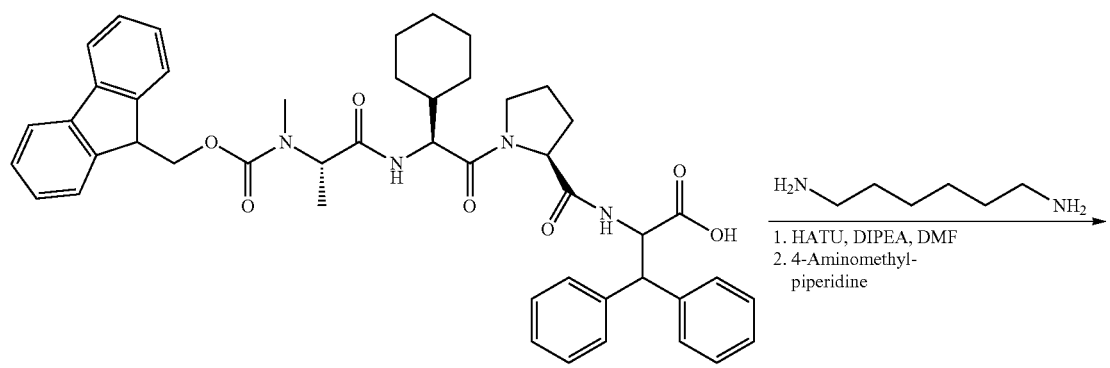

a

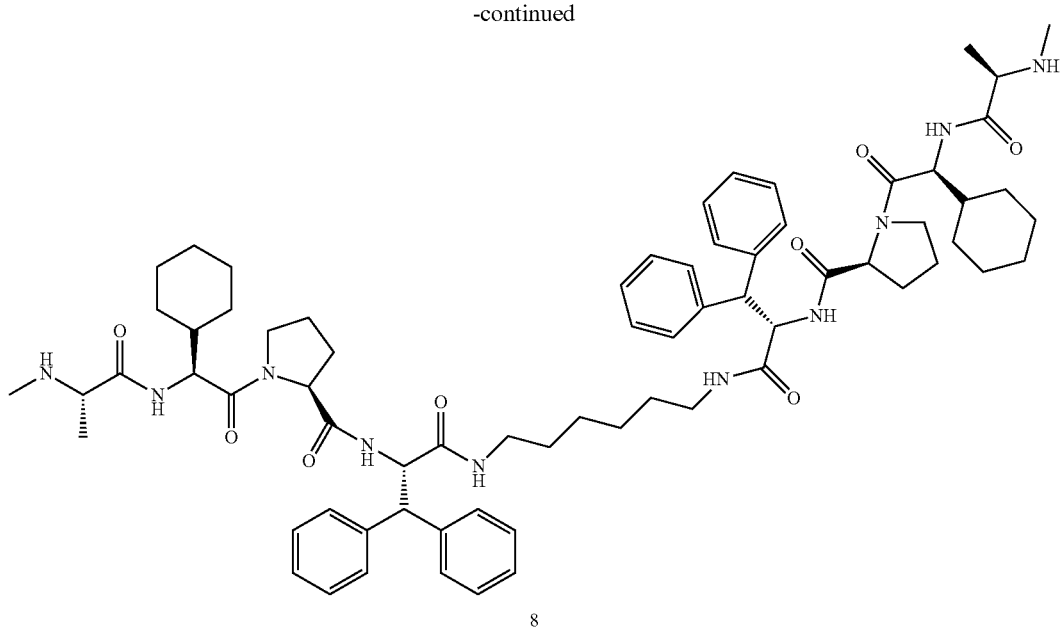

8

Compound a (160 mg, 0.2 mmol) was dissolved in 1 mL DMF and HATU (91 mg, 0.24 mmol) followed by addition of 1,6-diaminohexane (12 mg, 0.1 mmol) and diisoproplyethylamine (52 μL, 0.3 mmol). The reaction was stirred at room temperature for 14 hours. The reaction was diluted with EtOAc, washed 2× with saturated NaHCO$_3$ and washed with brine. Dried over MgSO$_4$ and concentrated. The residue was dissolved in 2 mL DMF followed by the addition of 4-aminomethylpiperidine (120 μL, 1.0 mmol) and stirred at room temperature for 3 hours. Preparative HPLC gave compound 8. MS=1205.2 (M+1).

Example 39

Dimer Compound 9

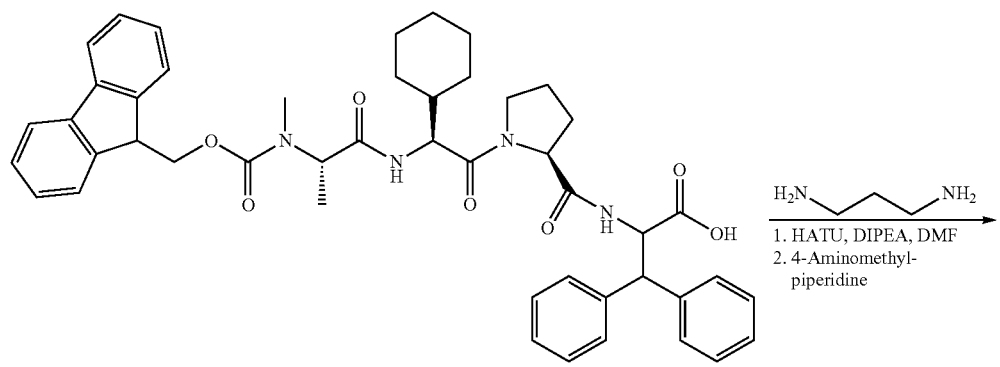

a

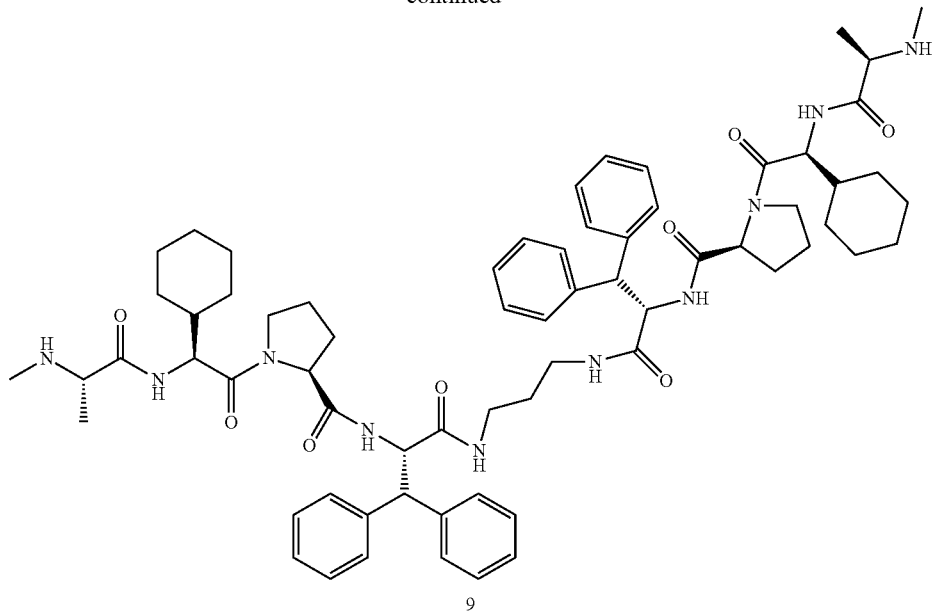

9

Compound a (135 mg, 0.17 mmol) was dissolved in 1 mL DMF, HATU (91 mg, 0.24 mmol) was added followed by 1,6-diaminopropane (8 µL, 0.09 mmol) and diisoproplyethylamine (44 µL, 0.26 mmol). The reaction was stirred at room temperature for 14 hours. The reaction was diluted with EtOAc, washed 2× with saturated NaHCO$_3$ and washed with brine. Dried over MgSO$_4$ and concentrated. The residue was dissolved in 2 mL DMF followed by the addition of 4-aminomethylpiperidine (104 µL, 0.85 mmol) and stirred at room temperature for 3 hours. Preparative HPLC gave compound 8. MS=1164.5 (M+1).

Example 40

Dimer Compound 9

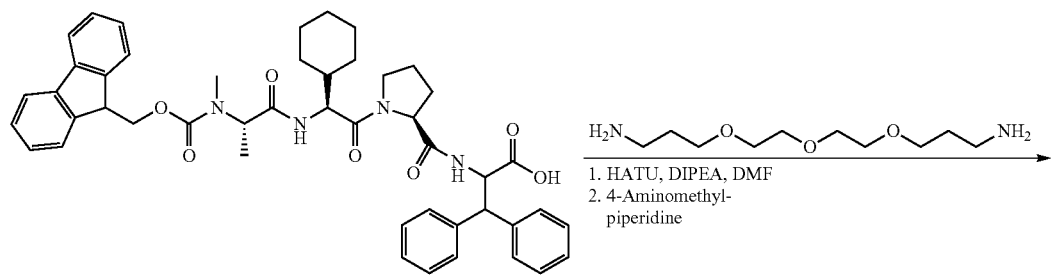

a

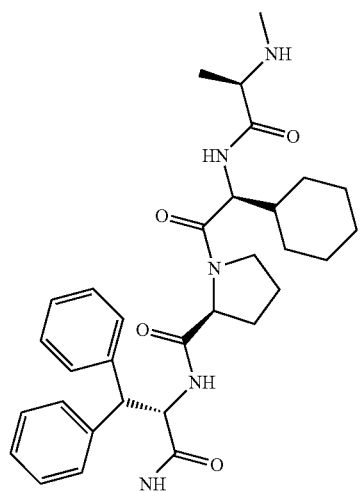
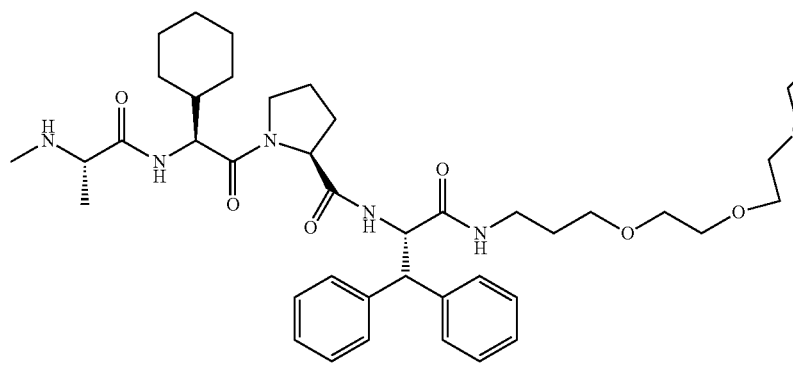
Compound 9 was prepared according of the procedures described for compound 8. MS=1310.7 (M+1).
Example 41
Dimer Compound 22
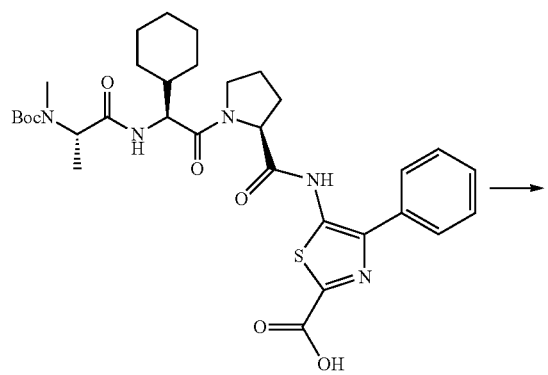
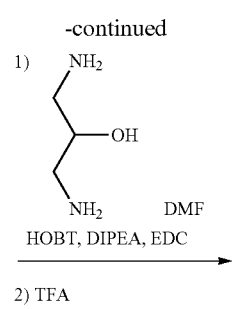
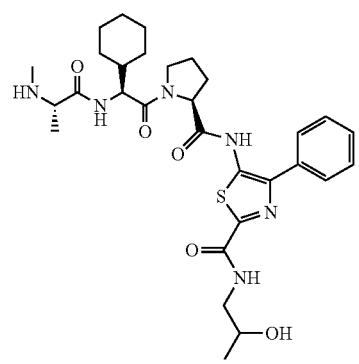

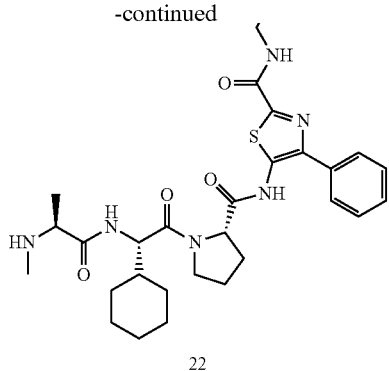

22

To compound a (665.0 mg, 1.036 mmol) in N,N-dimethylformamide (10.0 mL, 129 mmol) was added 1-hydroxybenzotriazole (0.154 g, 1.14 mmol), 1,3-diaminopropan-2-ol (0.0467 g, 0.518 mmol), and N,N-diisopropylethylamine (0.451 mL, 2.59 mmol). After the solids went into solution, N-(3-dimethylaminopropyl)-N'-ethylcarbodiimide hydrochloride (0.218 g, 1.14 mmol) was added and the solution was stirred at RT overnight.

The solution was heated to 50° C. and continued stirring overnight. The solution was diluted with EtOAc (150 ml) and washed with 1N HCl 2× (150 ml). The combined acidic aqueous phases were extracted with EtOAc 1× (100 ml) and the combined organics were washed with 1N NaOH 2× (150 ml). The combined basic layers were extracted with EtOAc 1× (100 ml). The combined organic phases were washed with brine 1× (150 ml), dried (Na$_2$SO$_4$), filtered and concentrated with a Genevac evaporator and then flashed (ISCO 80G solid load (0-80%) 10% MeOH/DCM, DCM) to give Boc-protected dimer The Boc-protected dimer was treated with 1:1 solution of DCM and TFA (5 ml) for 10 minutes and concentrated. The crude material was purified by HPLC to give 77.3 mg of final dimer compound 22.

Example 42

Dimer Compound 23

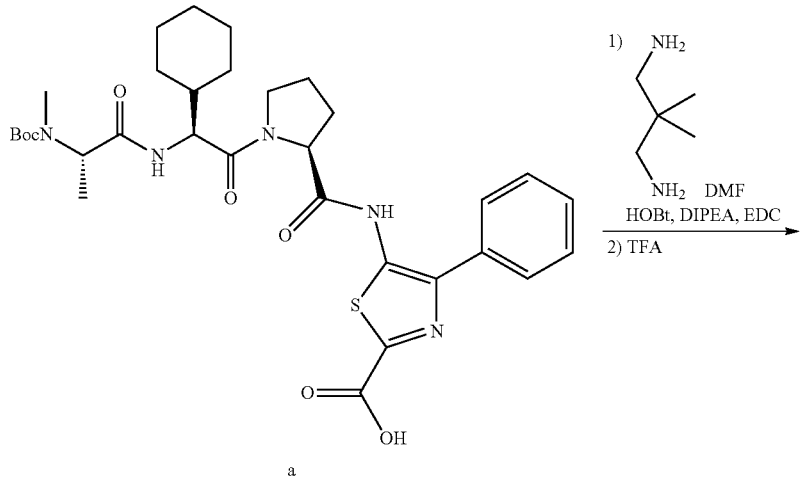

a

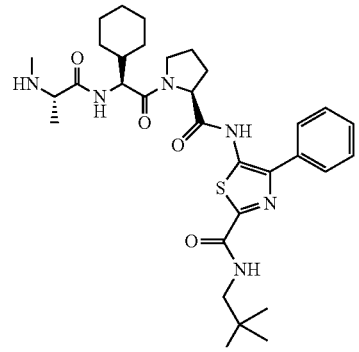

-continued

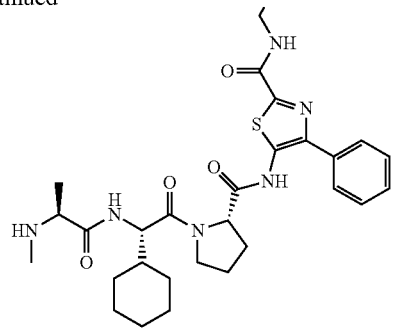

23

In vial of compound a (700.0 mg, 1.091 mmol) was added 1-hydroxybenzotriazole (0.162 g, 1.20 mmol), N,N-dimethylformamide (3.500 mL, 45.20 mmol), 2,2-dimethylpropane-1,3-diamine (0.0655 mL, 0.545 mmol), N,N-diisopropylethylamine (0.475 mL, 2.73 mmol), N-(3-dimethylaminopropyl)-N'-ethylcarbodiimide hydrochloride (0.230 g, 1.20 mmol) in order and stirred at 50° C. overnight. The solution was diluted with EtOAc (150 ml) and washed with 1N HCl 2× (150 ml). The combined acidic aqueous phases were extracted with EtOAc 1× (100 ml) and the combined organics were washed with sat bicarbonate 2× (150 ml). The combined basic phases were extracted with EtOAc 1× (100 ml) and the combined organic phases washed with brine 1× (150 ml), dried ($Na_2SO_4$), filtered, concentrated and then flashed (ISCO 80G solid load column 0-5% MeOH/DCM, 45 min) to give Boc-protected dimer To the residue was added TFA/DCM 1:1 solution of trifluoroacetic acid:methylene chloride (5.00 mL) which was stirred for 10 min at RT and then rotovaped followed by addition of DCM and then rotovaped again. This was concentrated by Genevac to give 163.7 mg of crude dimer which was purified by HPLC to give 86.3 mg of purified dimer compound 23.

Example 43

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

MLXBIR3SG Sequence:

(SEQ ID NO.: 1)
MGSSHHHHHHSSGLVPRGSHMLETEEEEEEGAGATLSRGPAFPGMGSE

ELRLASFYDWPLTAEVPPELLAAAGFFHTGHQDKVRCFFCYGGLQSWK

RGDDPWTEHAKWFPGCQFLLRSKGQEYINNIHLTHSL

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 µg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.). Indications of antagonist potency were determined from the IC50 values. Compounds of the invention that were tested in this assay exhibited IC50 values of less than 200 µM indicating IAP inhibitory activity.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S. (2000) in *Proceedings of SPIE: In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 µM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-$NH_2$ (AVP-diPhe-FAM) at 5 nM final concentration.

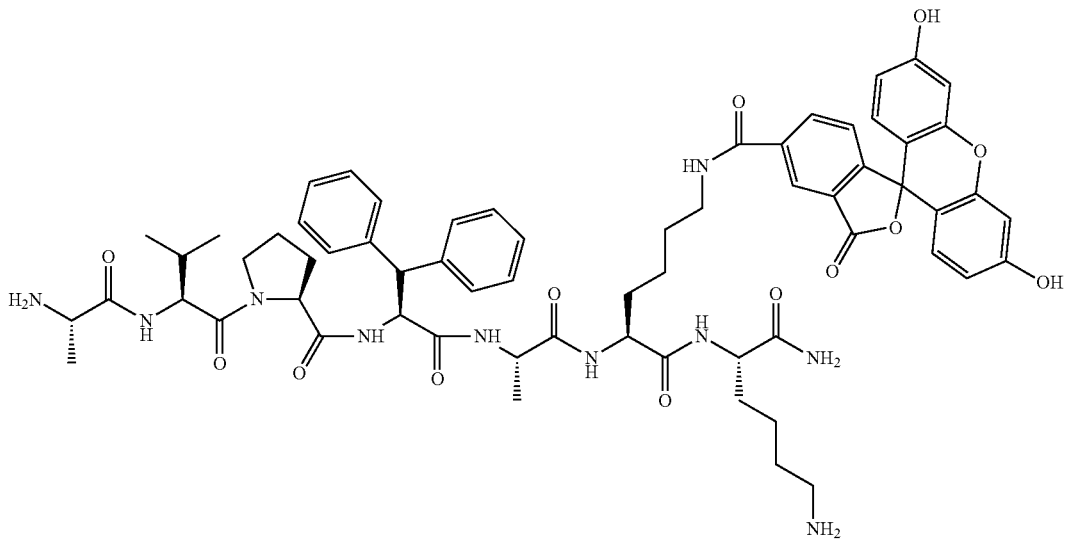

AVP-diPhe-FAM probe

The reactions were read after an incubation time of 10 minutes at room temperature with standard cut-off filters for the fluorescein fluorophore ($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 µM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.) Inhibition constants ($K_i$) for the antagonists were determined from the $IC_{50}$ values. Compounds of the invention that were tested in this assay exhibited an $IC_{50}$ of less than 10 µM. Compound 2 had an $IC_{50}$ of 0.2787 µM, compound 10 had an $IC_{50}$ of 1.324 µM, compound 1 had an $IC_{50}$ of 0.2309 µM, compound 4 had an $IC_{50}$ of 2.4054 µM, compound 11 had an $IC_{50}$ of 1.0261 µM, compound 12 had an $IC_{50}$ of 1.0965 µM, compound 13 had an $IC_{50}$ of 3.8188 µM, compound 14 had an $IC_{50}$ of 2.3450 µM, compound 15 had an $IC_{50}$ of 3.8334 µM, compound 16 had an $IC_{50}$ of 0.2341 µM, compound 24 had an $IC_{50}$ of 1.3802 µM, compound 17 had an $IC_{50}$ of 0.1677 µM, compound 23 had an $IC_{50}$ of 0.6793 µM and compound 22 had an $IC_{50}$ of 0.3780 µM.

---

We claim:

1. A compound of formula Va, VIa, VIIa, or XX,

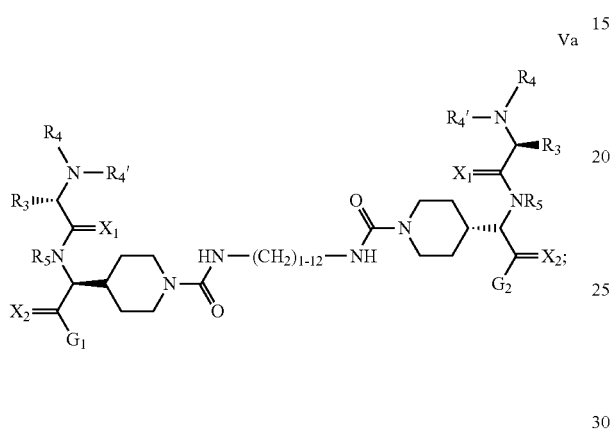

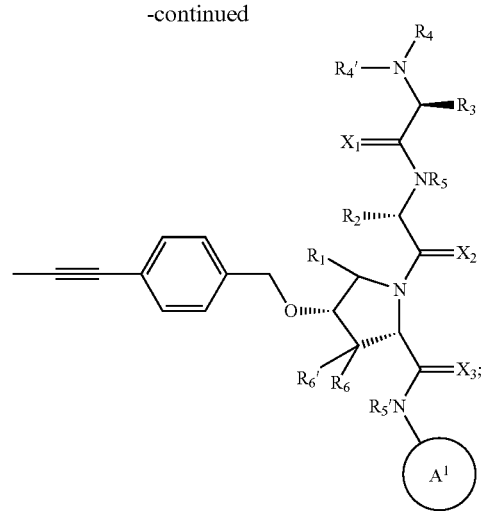

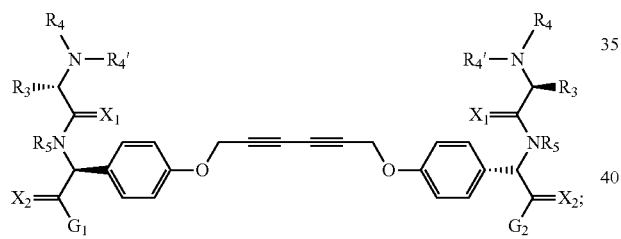

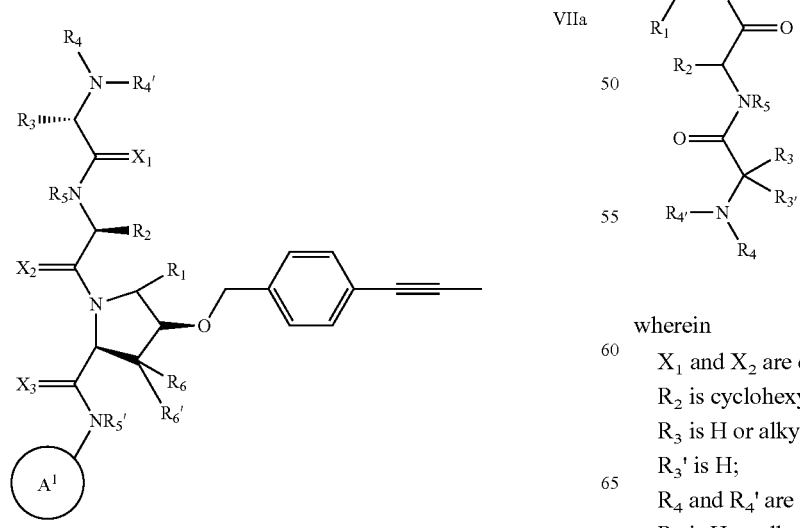

wherein $X_1$ and $X_2$ are each independently O or S;

$R_2$ is cyclohexyl, phenyl, or piperidinyl;

$R_3$ is H or alkyl;

$R_3'$ is H;

$R_4$ and $R_4'$ are independently H or alkyl;

$R_5$ is H or alkyl;

$G_1$ and $G_2$ are each independently IVb:

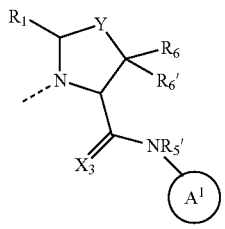

wherein
$R_1$ is H;
$R_5'$ is H or alkyl;
$R_6$ and $R_6'$ are each H;
$A^1$ is a thiazole or thiadiazole optionally substituted with acylamino, or a heterocycle; wherein each heterocycle substitution is optionally substituted with alkyl;
$X_3$ is O or S; and
Y is $CH_2$; and
M is —C(O)NH(CH$_2$)$_7$NHC(O)—, —C(O)NH(CH$_2$)$_{11}$NHC(O)—, —C(O)NH—(CH$_2$O)$_2$—(CH$_2$)$_2$—NHC(O)—, —C(O)NH—CH$_2$CH$_2$CH$_2$—NR$^y$—CH$_2$CH$_2$CH$_2$—NHC(O)—, —C(O)NH—CH$_2$—CH(OH)—CH$_2$—NHC(O)—, —C(O)NH—CH$_2$—C(CH$_3$)$_2$—CH$_2$—NHC(O)—, or —C(O)NHCH$_2$-phenyl-CH$_2$—NHC(O)—;
wherein $R^y$ is methyl, acetyl, or —C(O)—(CH$_2$)$_{1-6}$-(3-(2-amino-2-carboxyethyl)-2,5-dioxopyrrolidin-1-yl);
or a pharmaceutically acceptable salt thereof.

2. The compound of claim 1, wherein $R_3$ is methyl.
3. The compound of claim 1, wherein $R_4$ is H or methyl, and $R_4'$ is H.
4. The compound of claim 1, wherein $R_5$ is H or methyl.
5. The compound of claim 1, wherein $X_1$ and $X_2$ are both O.
6. The compound of claim 1, wherein $R_2$ is cyclohexyl or phenyl; $R_3$ is methyl; $R_4$ is methyl; $R_4'$ is H; $R_5$ is H; and $X_1$ and $X_2$ are both O.
7. A method of inducing apoptosis in a cell comprising introducing into said cell a compound of claim 1.
8. A method of sensitizing a cell to an apoptotic signal comprising introducing into said cell a compound of claim 1.
9. The method of claim 8, wherein said apoptotic signal is induced by contacting said cell with a compound selected from the group consisting of cytarabine, fludarabine, 5-fluoro-2'-deoxyuridine, gemcitabine, methotrexate, bleomycin, cisplatin, cyclophosphamide, adriamycin (doxorubicin), mitoxantrone, camptothecin, topotecan, colcemid, colchicine, paclitaxel, vinblastine, vincristine, tamoxifen, finasteride, taxotere and mitomycin C or radiation.
10. The method of claim 8, wherein said apoptotic signal is induced by contacting said cell with Apo2L/TRAIL.
11. A method for inhibiting the binding of an IAP protein to a caspase protein comprising contacting said IAP protein with a compound of claim 1.
12. A compound selected from the group consisting of:

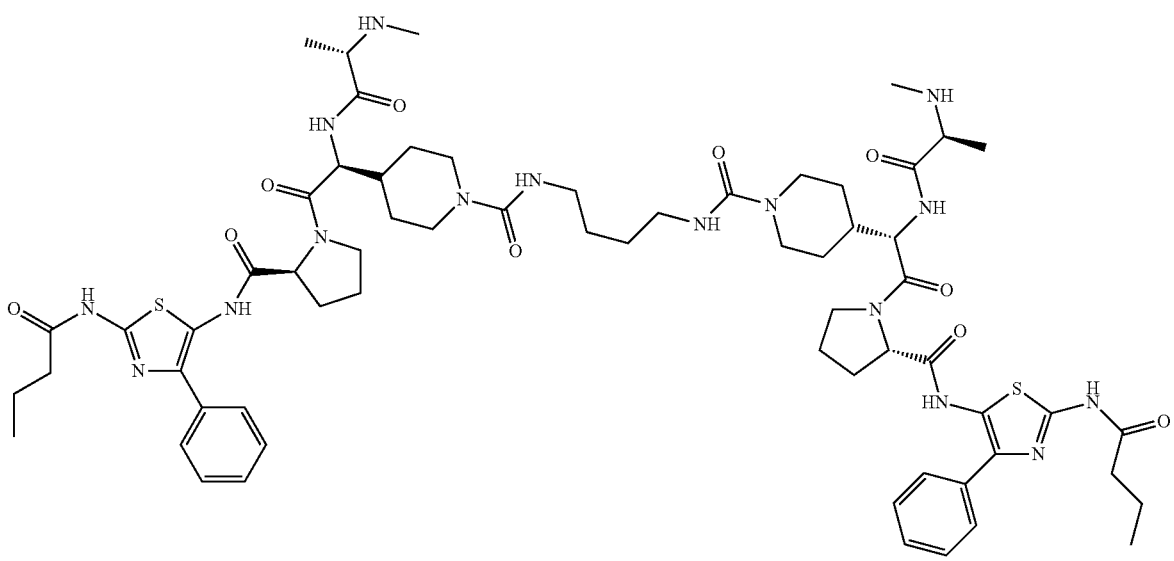

-continued
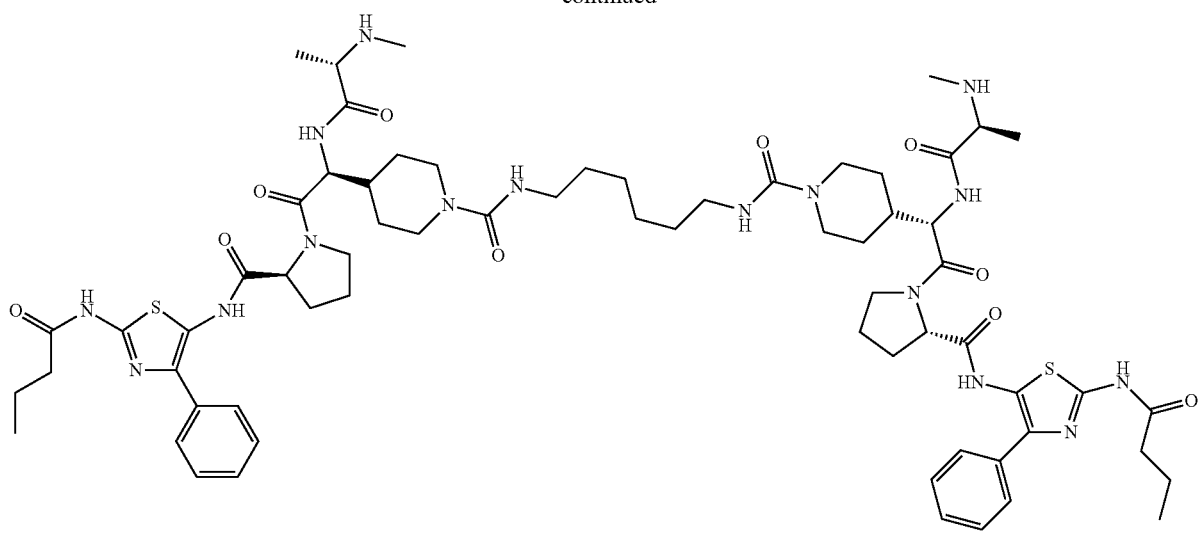
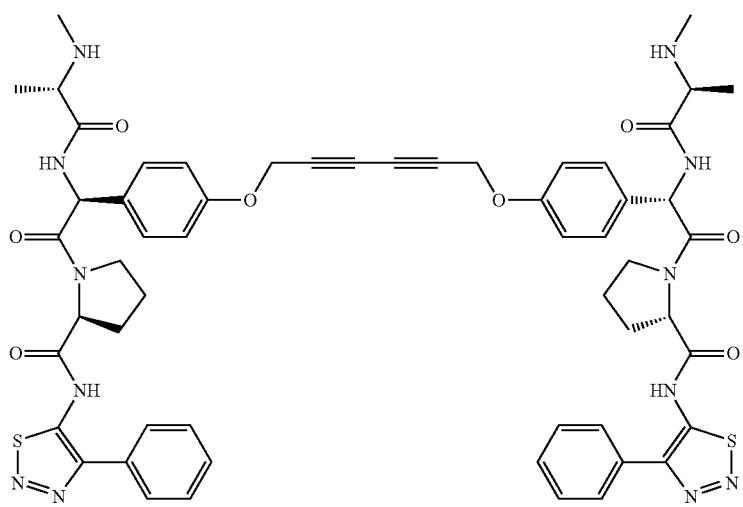
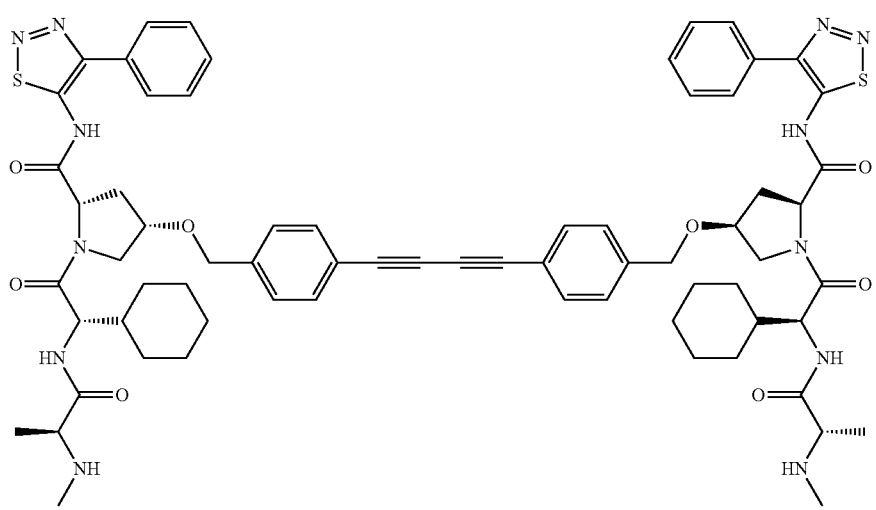 [SMILES: CN[C@@H](C)C(=O)N[C@H](C(=O)N1C[C@@H](OCc2ccc(C#CC#Cc3ccc(CO[C@H]4C[C@@H](C(=O)Nc5snnc5-c5ccccc5)N(C(=O)[C@@H](NC(=O)[C@H](C)NC)C5CCCCC5)C4)cc3)cc2)C[C@H]1C(=O)Nc1snnc1-c1ccccc1)C1CCCCC1]

-continued
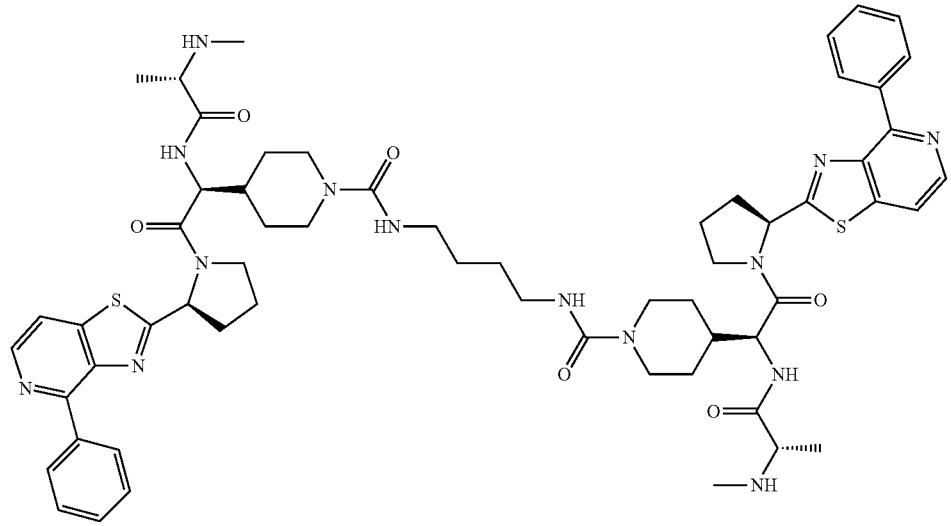
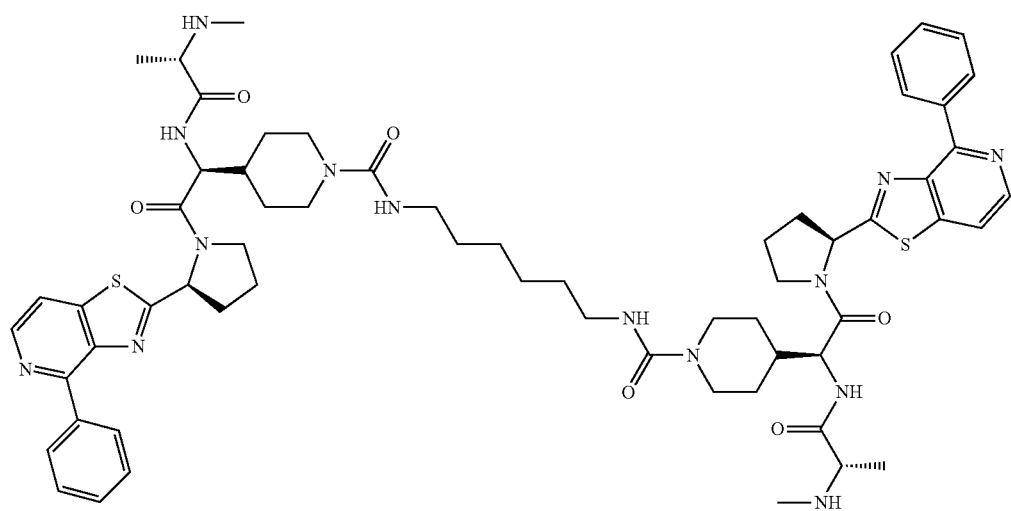
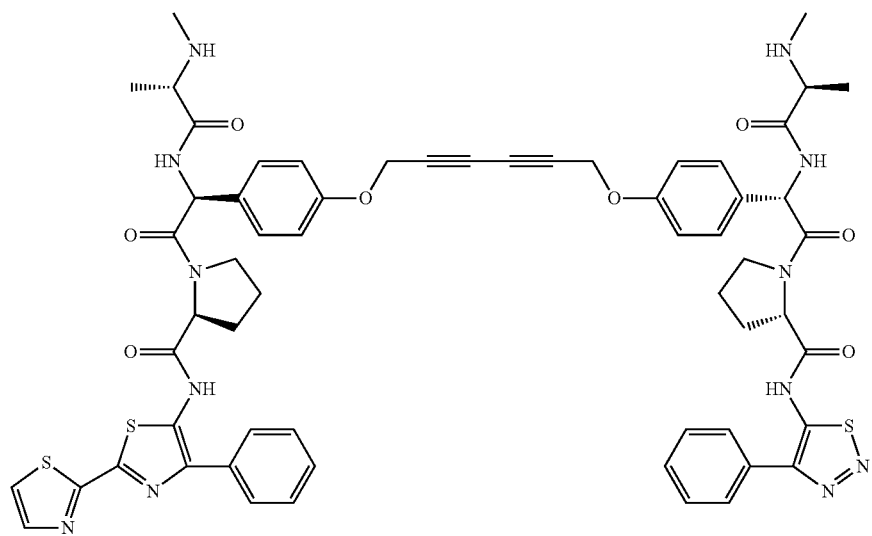

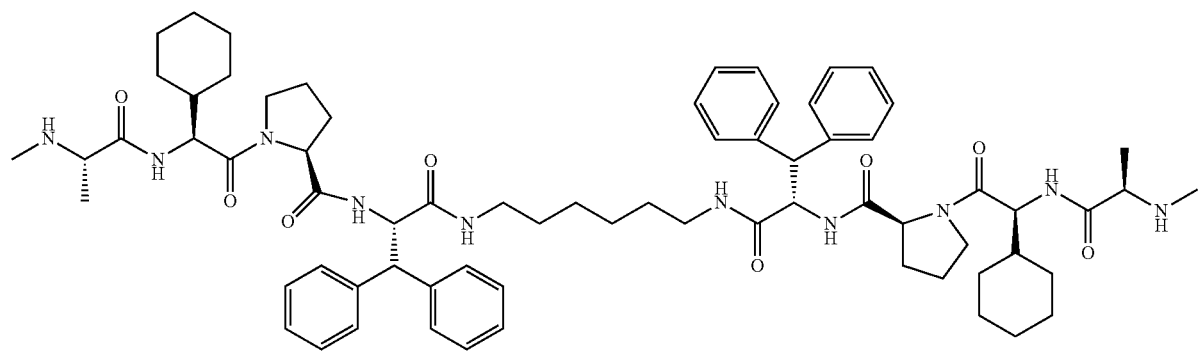
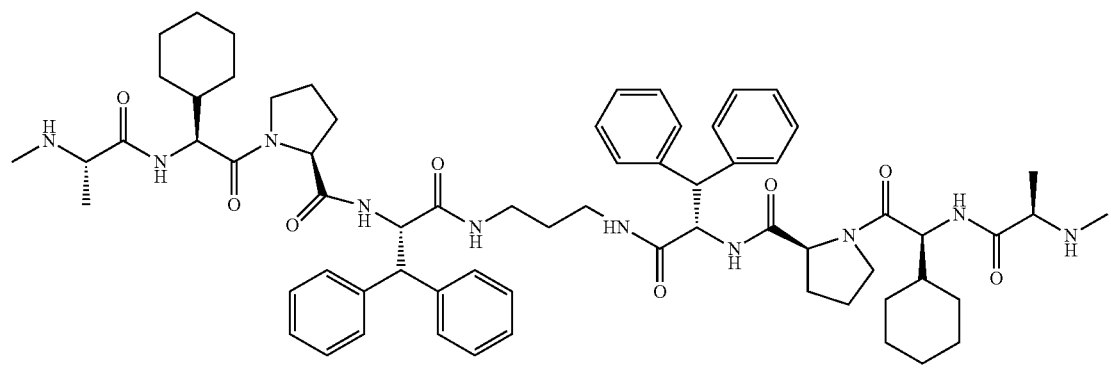
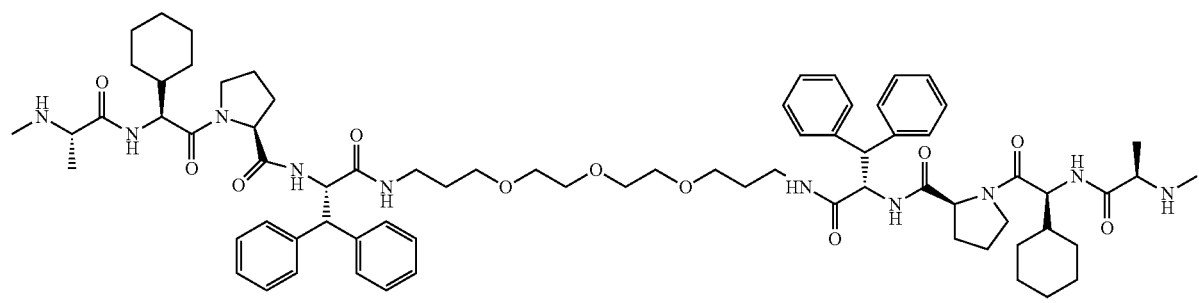
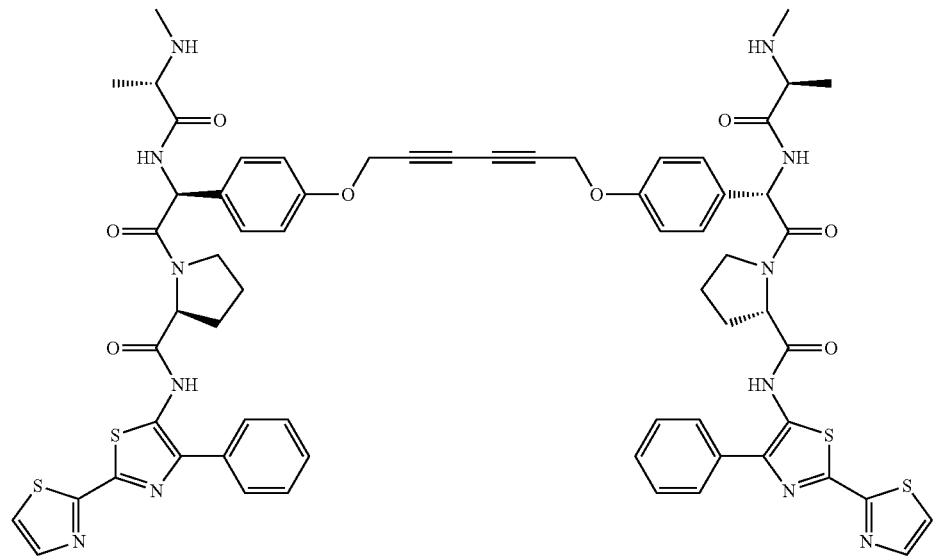

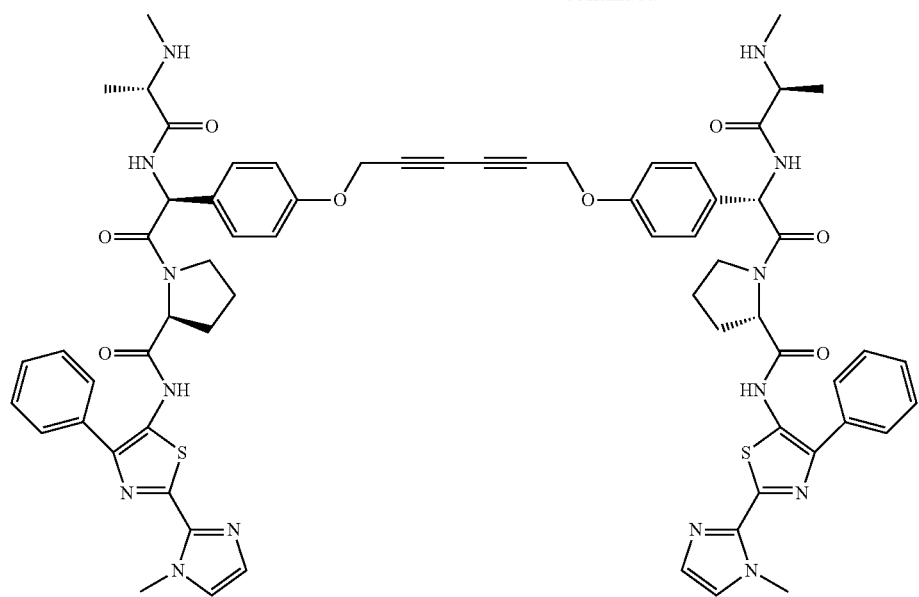
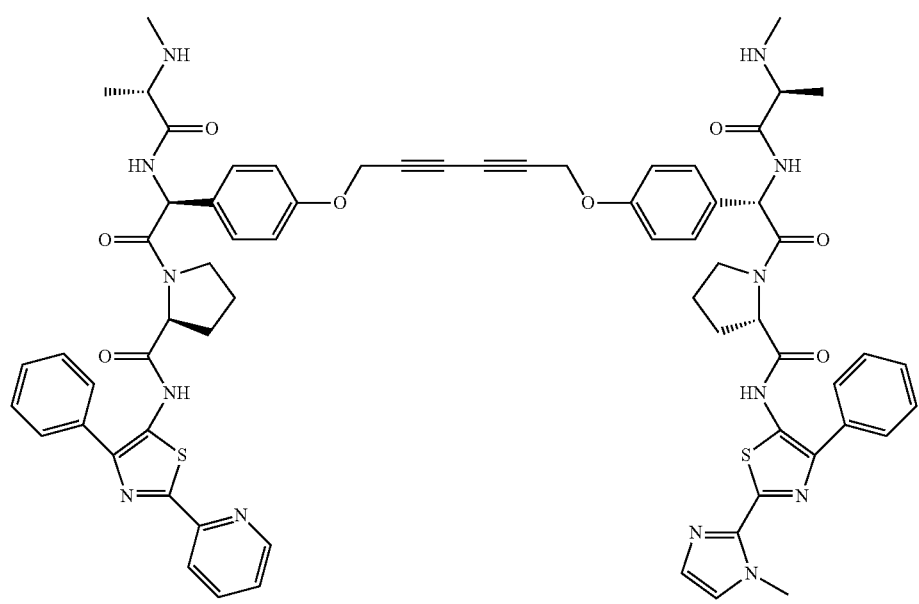

173 174
-continued
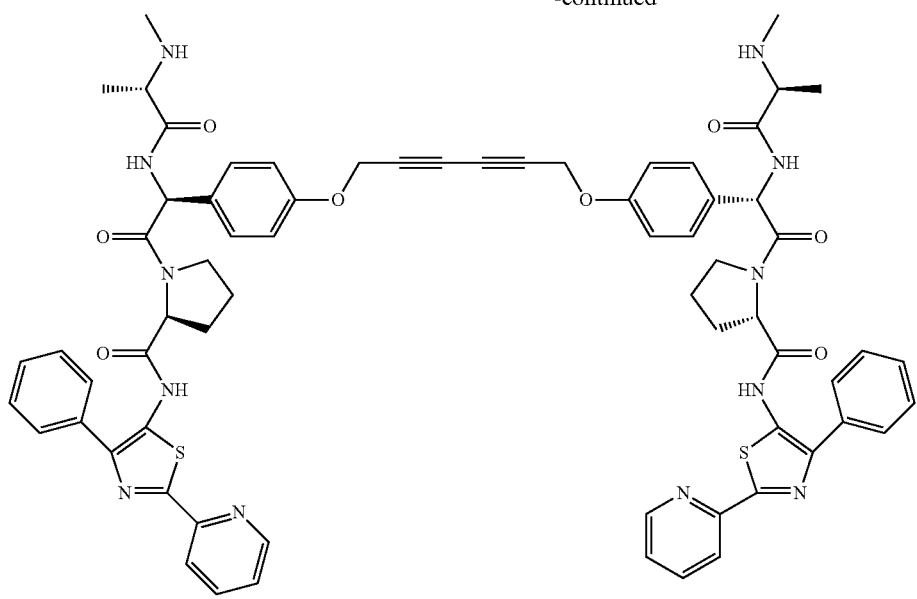
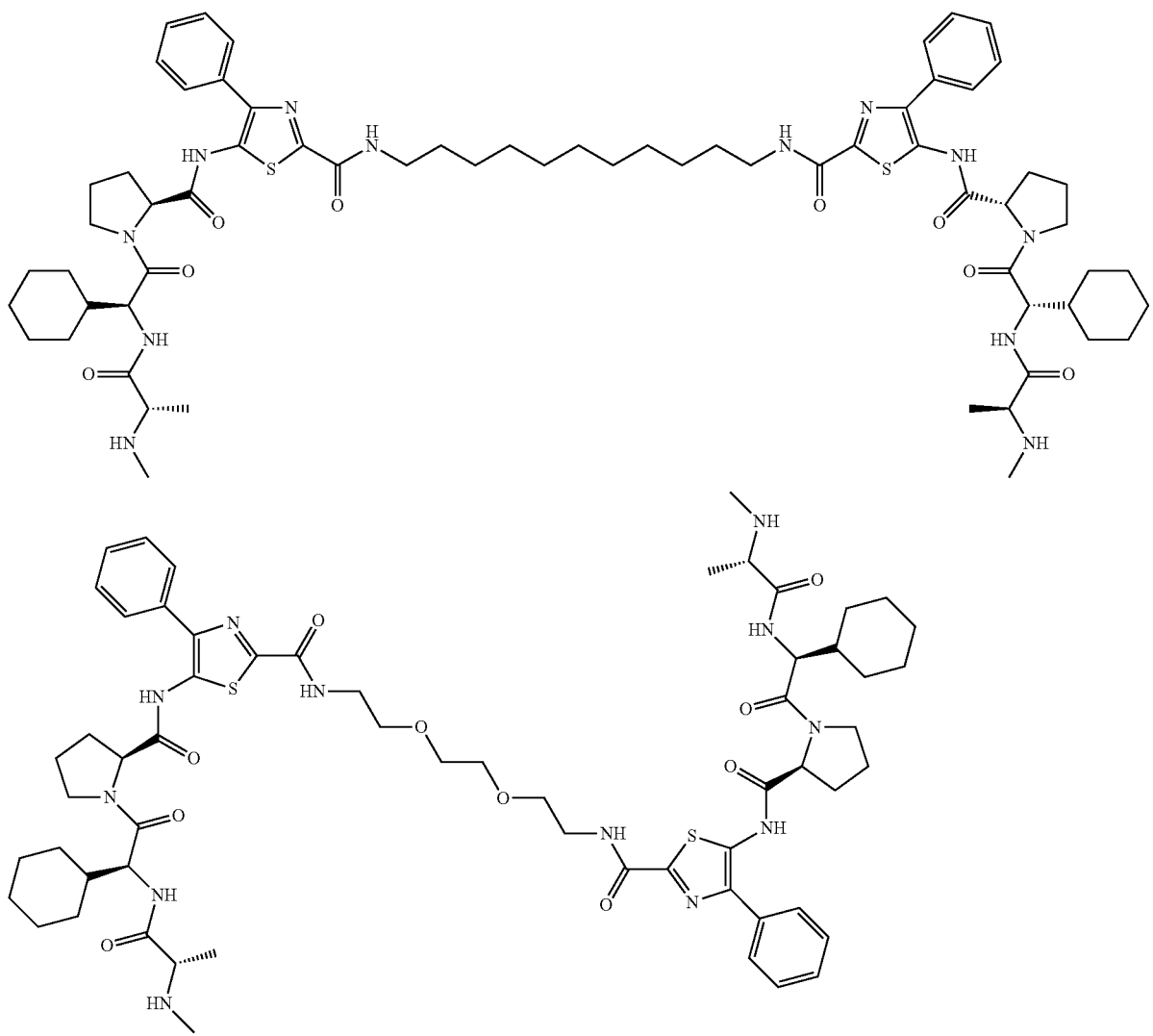

175 176
-continued
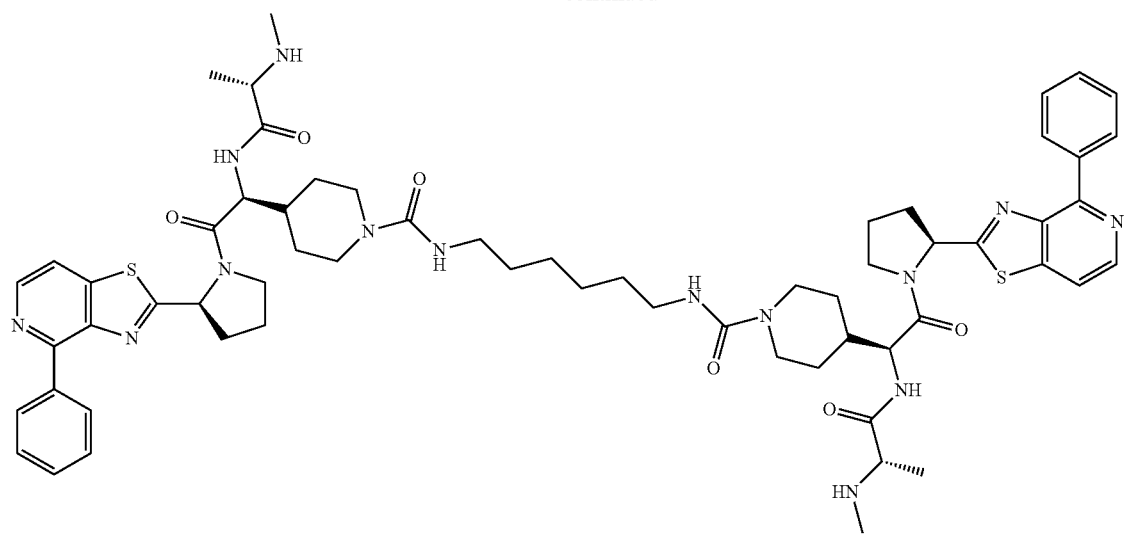
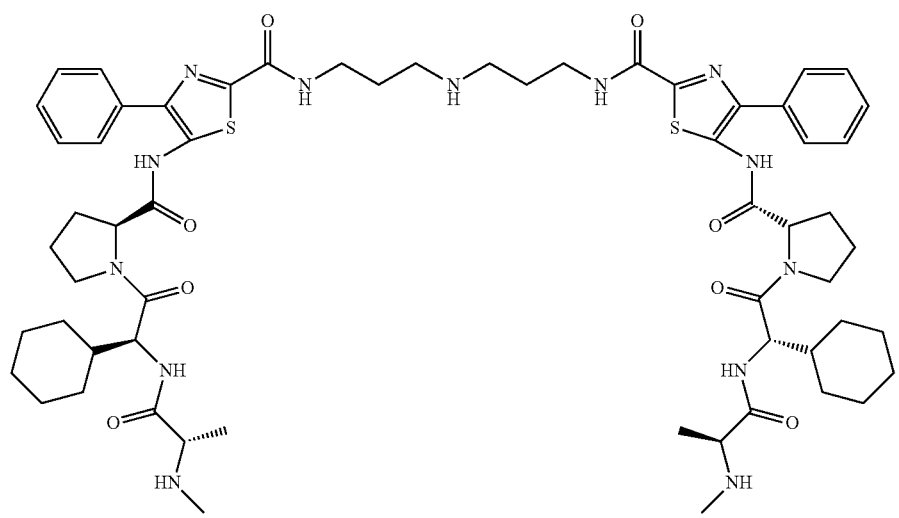
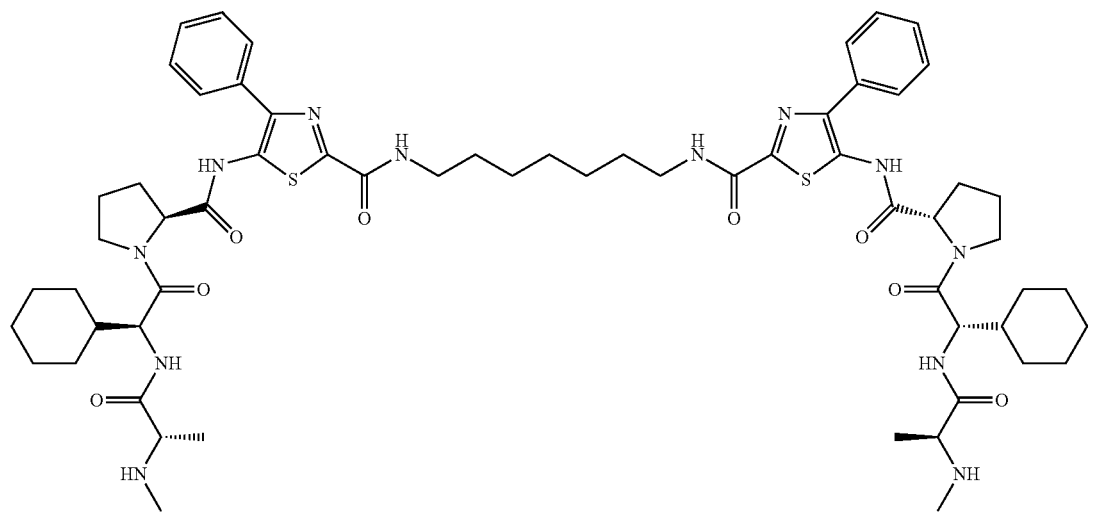

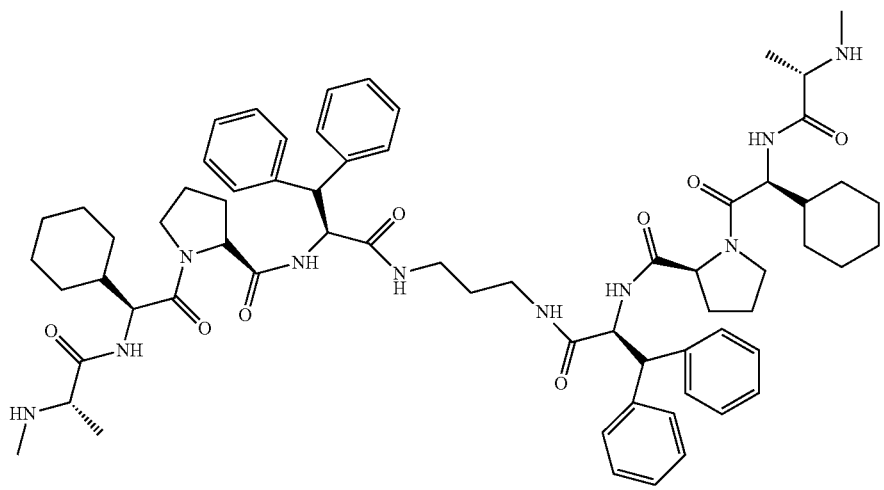
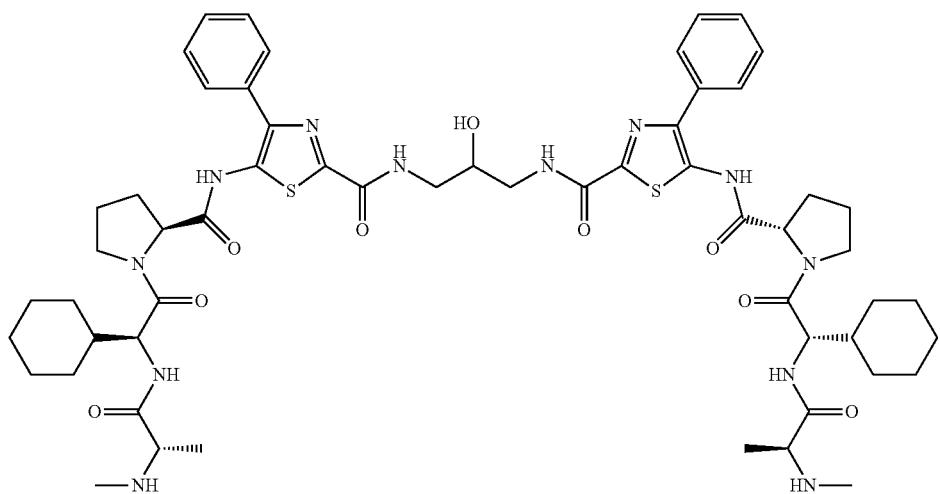
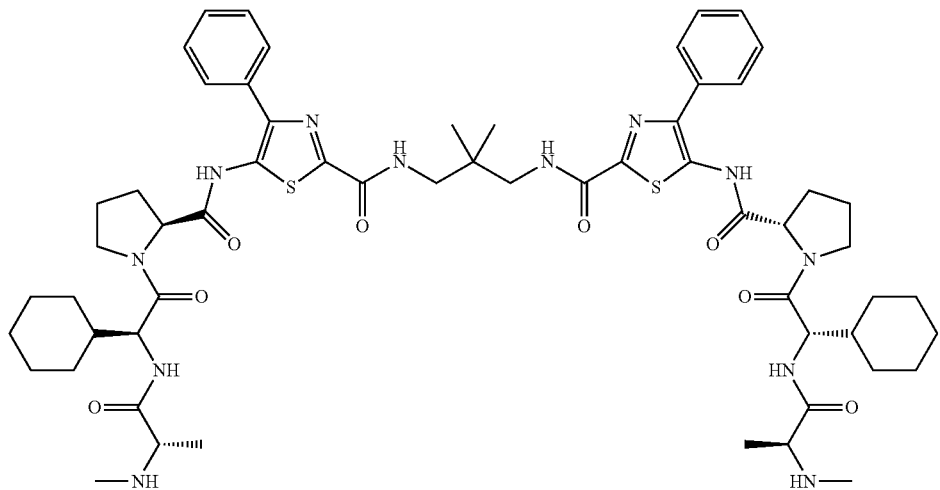

-continued
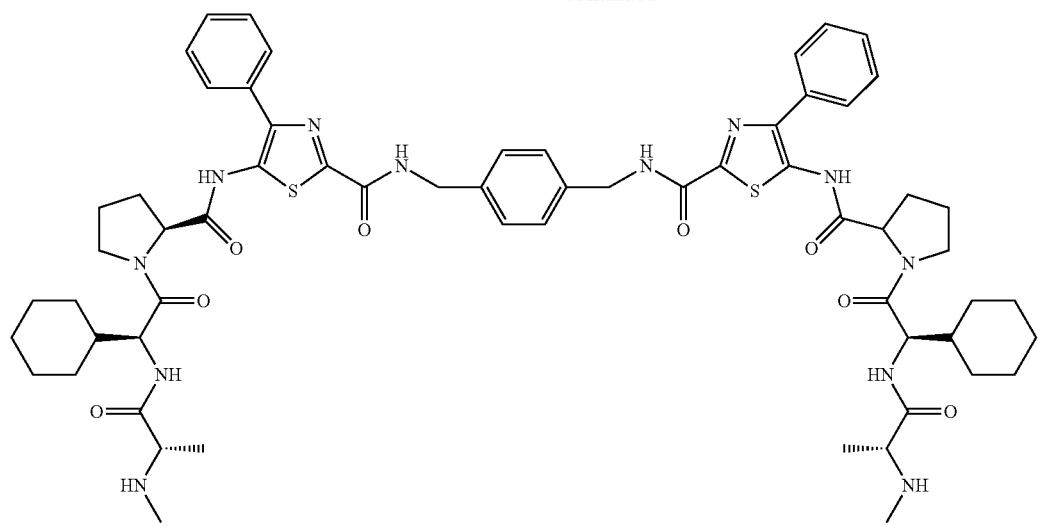
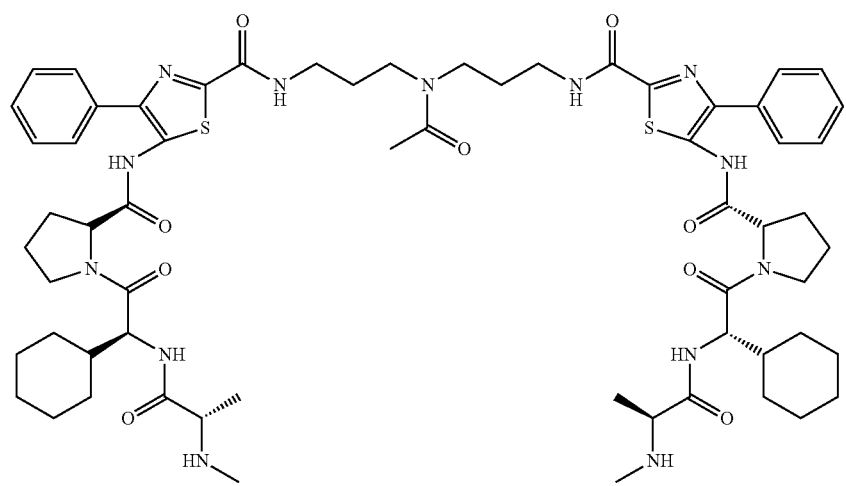
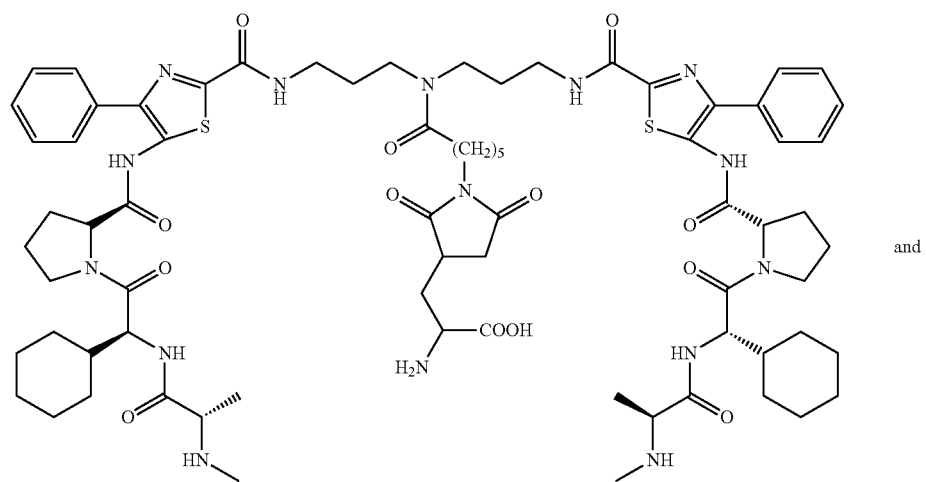
and

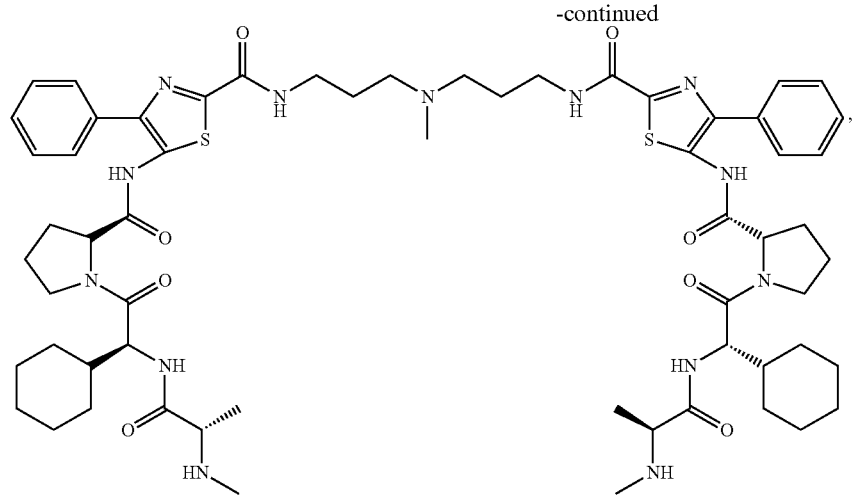
and pharmaceutically acceptable salts thereof.
* * * * *